US012703743B2

(12) United States Patent
Zhang et al.

(10) Patent No.: US 12,703,743 B2
(45) Date of Patent: Aug. 11, 2026

(54) ANTI-CD47 MONOCLONAL ANTIBODY AND USE THEREOF

(71) Applicant: Akeso Biopharma, Inc, Zhongshan (CN)

(72) Inventors: Peng Zhang, Zhongshan (CN); Baiyong Li, Zhongshan (CN); Yu Xia, Zhongshan (CN); Zhongmin Wang, Zhongshan (CN)

(73) Assignee: Akeso Biopharma, Inc., Zhongshan (CN)

( * ) Notice: Subject to any disclaimer, the term of this patent is extended or adjusted under 35 U.S.C. 154(b) by 1091 days.

(21) Appl. No.: 17/640,005

(22) PCT Filed: Sep. 3, 2020

(86) PCT No.: PCT/CN2020/113287
§ 371 (c)(1),
(2) Date: Mar. 3, 2022

(87) PCT Pub. No.: WO2021/043220
PCT Pub. Date: Mar. 11, 2021

(65) Prior Publication Data

US 2022/0324971 A1 Oct. 13, 2022

(30) Foreign Application Priority Data

Sep. 3, 2019 (CN) ......................... 201910835819.2
Sep. 3, 2019 (CN) ......................... 201910836601.9

(51) Int. Cl.

| | |
|---|---|
| ***C07K 16/28*** | (2006.01) |
| ***A61K 35/13*** | (2015.01) |
| ***A61K 39/00*** | (2006.01) |
| ***A61P 35/00*** | (2006.01) |

(52) U.S. Cl.
CPC .......... *C07K 16/2803* (2013.01); *A61K 35/13* (2013.01); *A61P 35/00* (2018.01); *A61K 2039/505* (2013.01); *C07K 2317/14* (2013.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
CPC ............ C07K 16/2803; C07K 2317/14; C07K 2317/24; C07K 2317/565; C07K 2317/567; C07K 2317/76; C07K 2317/92; C07K 2317/53; C07K 2319/21; C07K 16/28; C07K 19/00; C07K 2317/31; A61K 35/13; A61K 2039/505; A61K 39/395; A61K 47/68; A61P 35/00; C12N 15/85; C12N 5/10; G01N 2333/70596
See application file for complete search history.

(56) References Cited

U.S. PATENT DOCUMENTS

| | | | |
|---|---|---|---|
| 4,816,567 | A | 3/1989 | Cabilly |
| 4,946,778 | A | 8/1990 | Ladner |
| 5,260,203 | A | 11/1993 | Ladner |
| 2017/0081407 | A1 | 3/2017 | Grosveld |
| 2019/0023784 | A1 | 1/2019 | Chalons-Cottavoz |

FOREIGN PATENT DOCUMENTS

| | | |
|---|---|---|
| CN | 108290948 | 7/2018 |
| CN | 109265547 | 1/2019 |
| CN | 109438576 | 3/2019 |
| JP | 2022513964 | 2/2022 |
| WO | 8801649 | 3/1988 |
| WO | 2015191861 | 12/2015 |
| WO | 2017049251 | 3/2017 |
| WO | 2018089508 | 5/2018 |
| WO | 2018137705 | 8/2018 |
| WO | 2019027903 | 2/2019 |
| WO | 2019042285 | 3/2019 |
| WO | 2019086573 | 5/2019 |
| WO | 2019144895 | 8/2019 |

OTHER PUBLICATIONS

Dondelinger et al. Understanding the significance and implications of anitbody numbering and antigen-binding surface/ residue definition. Front Immunol, 2018, 9: 2278. (Year: 2018).*
Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Liu, X., Kwon, H., Li, Z et al. Is CD47 an innate immune checkpoint for tumor evasion?. J Hematol Oncol 10, 12 (2017). (Year: 2017).*
Gershoni et al. Epitope mapping: the first step in developing epitope-based vaccines. BioDrugs. 2007;21(3):145-56. (Year: 2007).*
Blythe et al. Benchmarking B cell epitope prediction: underperformance of existing methods. Protein Sci. Jan. 2005; 14(1):246-8. (Year: 2005).*
Schreiber et al. 3D-Epitope-Explorer (3DEX): localization of conformational epitopes within three-dimensional structures of proteins. J Comput Chem. Jul. 15, 2005;26(9):879-87. (Year: 2005).*
Ladner RC. Mapping the epitopes of antibodies. Biotechnol Genet Eng Rev. 2007;24:1-30. (Year: 2007).*
Liu J, Wang L, Zhao F, Tseng S, Narayanan C, Shura L, Willingham S, Howard M, Prohaska S, Volkmer J, Chao M, Weissman IL, Majeti R. Pre-Clinical Development of a Humanized Anti-CD47 Antibody with Anti-Cancer Therapeutic Potential. PLoS One. Sep. 21, 2015;10(9):e0137345. (Year: 2015).*
Pearson WR. Rapid and sensitive sequence comparison with FASTP and FASTA. Methods Enzymol. 1990; 183:63-98. (Year: 1990).*
Vidarsson, et al. "IgG subclasses and allotypes: from structure to effector functions", 5 (520): 1-17 (2014).

(Continued)

*Primary Examiner* — Julie Wu
*Assistant Examiner* — Amber K Faust
(74) *Attorney, Agent, or Firm* — PABST PATENT GROUP LLP

(57) ABSTRACT

Provided are an anti-CD47 monoclonal antibody and a use thereof, secreted by the hybridoma cell line with the deposit number CCTCC NO: C2018135.

23 Claims, 9 Drawing Sheets

Specification includes a Sequence Listing.

(56) References Cited

OTHER PUBLICATIONS

Yu, et al. "A novel fully human anti-CD47 antibody as a potential therapy for human neoplasms with good safety" 151(2018)54-66 (2018).
Winkler, et al. "Changing the Antigen Binding Specificity by Single Point Mutations of an Anti-p24 (HIV-1) Antibody" 165: 4505-4514 (2000).
European Search Report: PCT/CN2020/113287 dated Dec. 13, 2023.
Rudikoff, et al. "Single Amino Acid Substitution Altering Antigen-Binding Specificity" vol. 79, pp. 1979-1983, (2006).
Kunik, et al. "Structural Consensus among Antibodies Defines the Antigen Binding Site" 8(2) e1002388 (2012).
Bai, "Achievements and concerns of the CD47 targeted anti-cancer therapy", Chinese Clinical Oncology, 44(7):344-348 (2017).
Chao, et al., "Abstract PR13: The anti-CD47 antibody Hu5F9-G4 is a novel immune checkpoint inhibitor with synergistic efficacy in combination with clinically active cancer targeting antibodies", Cancer Immunology Research, 4(11_supplement) (2016).
Demignot, et al., Mouse IgG2b monoclonal antibody fragmentation. Preparation and purification of Fab, Fc and Fab/c fragments, Abstract 121(2):209-17(1989).
Matozaki, et al., Functions and molecular mechanisms of the CD47-SIRPα signalling pathway. Trends in cell biology, 19(2): 72-80 (2009).
Oldenborg, et al., "Role of CD47 as a marker of self on red blood cells", Science, 288(5473):2051-2054 (2000).
Reichmann, et al., "Reshaping human antibodies for therapy", Nature, 332:323-329 (1988).
Vonderheide, et al., "CD47 blockade as another immune checkpoint therapy for cancer", Nature Medicine, 21(10):1122 (2015).
Van Regenmortel, et al., "What is a B-Cell Epitope?", Methods in Molecular Biologu, Epitope Mapping Protocols, 524(1):3-483 (2009).
Eurasian Office Action in Application No. 202290747 mailed May 31, 2022.
Singaporean Office Action; Search Report and 1st Written Opinion; Application#: 11202202095Q; mailed Dec. 11, 2024.
Altschul et al., "Gapped BLAST and PSI-BLAST: a new generation of protein database search programs", Nucleic Acids Res., 25(17):3389-402 (1997).
Altschul, et al., "Basic Local Alignemnet Search Tool", Mol. Biol., 215:403-410 (1990).
Bird, et al., "Single-chain antigen-binding proteins", Science, 242(4877):423-426 (1988).
Clark, "Antibody humanisation:a case of the 'Emperor's new clothes'? ", Immunol. Today, 21:397-402 (2000).
Gonnet, et al., "Exhaustive Matching of the Entire Protein Sequence Database", Science, 256:1443-45 (1992).
Huston, et al., "Protein engineering of anitbody binding sites: Recovery of specific activity in an anti-digozin single-chain Fv analogue produced in *Excherichi coli*", PNAS, 85:5879-5883 (1988).
English Translation of International Search Report for PCT/CN2020/113287 dated Dec. 16, 2020.
Jaiswal, et al., "CD47 is Upregulated on Circulating Hematopoietic Stem Cells and Leukemia Cells to Avoid Phagocytosis", Cell, 138(3) 271-285 (2009).
Jiang, et al., "Integrin-associated Protein is a Ligand for the P84 Neural Adhesion Molecule", Journal of Biological Chemistry, 274:559-62 (1999).
Jones, et al., "Replacing the complemetarity-determining regions in a human antibody with those from a mouse", Nature, 321:522-525 (1986).
Kohler, et al., "Continuous cultures of fused cells secreting antibody of predefined specificity", Nature, 256(5517):495-497 (1975).
Kostelny, et al., "Formation of a bispecific antibody by the use of leucine zippers", J. Immunol., 148(5):1547-1553 (1992).
Kunic, et al., "Structural Consensus among Antibodies Defines the Antigen Binding Site", PloS Compuational Biology, 8(2);e1002388 (2012).
Liu, et al., "Pre-clinical Development of a Humanized Anti-CD47 Antibody with Anti-Cancer Therapeutic Potential", Plos One, 10(9):1-23 (2015).
Partial European (EP) Search Report for correspondin PCT/CN2020/113287 dated Aug. 7, 2023.
Pearson, "Flexible sequence similarity searching with the FASTA3 program package", Methods Mol. Biol., 132:185-219 (2000)).
Pearson, "Rapid and Sensitive Sequence Comparison with FASTP and FASTA", Methods Enzymol., 183:63-98 (1990).
Pearson, "Using the FASTA program to search protein and DNA sequence databases", Methods Mol. Biol., 243:307-31 (1994).
Presta, "Antibody Engineering", Curr. Op. Struct. Biol., 2(4):593-596 (1992).
Reinemer, et al., "Crystals of a 1:1 Complex Between Human Interleukin-4 and the Extracellular Domain of Its Receptor Alpha Chain", Eur. J. Biochem., 258(2):831-6 (1998).
Sikic, et al., "First in-Human, First-in-Class Phase I Trial of the Anti-CD47Antibody Hu5F9-G4 in Patients With Advanced Cancers", 37(12):946-953 (2019).
Songsivilai, et al., "Bispecific antibody: a tool for diagnosis and treatment of disease", Clin. Exp. Immunol., 79(3):315-321 (1990).
Ward, et al., "Binding activities of a repertoire of single immunoglobulin variable domains secreted from *Escherichia coli*", Nature, 341:544-546 (1989).
European Office Action Application 20 861 103.8-1111 Mailed Apr. 23, 2026.

* cited by examiner

Antibody concentration (nM)

| 6F7 H1L1 (hG4) | HuSF9-G4 |
| --- | --- |
| $R^2$ = 0.988 | $R^2$ = 0.997 |
| EC50 = 0.194 | EC50 = 0.205 |

Antibody concentration (nM)

A:Hu5F9-G4

B:6F7H1L1(G1M)

ANTI-CD47 MONOCLONAL ANTIBODY AND USE THEREOF

CROSS-REFERENCE TO RELATED APPLICATIONS

This application is a National Phase application under 35 U.S.C. 371 of PCT/CN2020/113287, filed Sep. 3, 2020, and claims the benefit of and priority to Chinese Application No. 201910835819.2, filed Sep. 3, 2019, and Chinese Application No. 201910836601.9, filed Sep. 3, 2019, the disclosures of which are hereby incorporated herein by reference in their entirety.

REFERENCE TO SEQUENCE LISTING

The Sequence Listing submitted on Mar. 3, 2022, as a text file named "ABIO_102_ST25.txt," created on Sep. 3, 2020, and having a size of 77,971 bytes is hereby incorporated by reference.

TECHNICAL FIELD

The present invention relates to the fields of the treatment of autoimmune diseases and molecular immunology, and particularly to an anti-CD47 antibody, a pharmaceutical composition comprising the same, and use thereof. More particularly, the present invention relates to an anti-CD47 monoclonal antibody.

BACKGROUND

CD47 is also referred to as integrin associated protein (IAP). CD47 is a five-span transmembrane protein with a molecular weight of about 50 kDa and belongs to the immunoglobulin superfamily. Its extracellular N-terminus is an IgV domain and is connected to $\alpha v\beta 3$(CD51/CD61) and $\alpha IIb\beta 3$(CD41/CD61) integrins. CD47 is involved in a variety of physiological functions, such as cell transfer, T cell and Dendritic cell (DC) activation, and axonal development.

CD47 is expressed on all types of cells including erythrocytes, and is highly expressed on tumor cells. CD47 has two ligands, namely signal regulatory protein-α (SIRPα) and thrombospondin-1, (TSP1). SIRPα, a receptor transmembrane glycoprotein containing an immunoglobulin domain, belongs to the SIRP family, and is mainly expressed on macrophages and nerve cells. In the CD47-SIRPα pathway, CD47 protein binds to SIRPα and phosphorylates its immunoreceptor tyrosine-based inhibitory motif (ITIM), then intracellularly recruits SHP-1 protein to produce a series of cascade reactions to inhibit macrophage phagocytosis (Matozaki T, Murata Y, Okazawa H, et al. Functions and molecular mechanisms of the CD47-SIRPα signalling pathway. *Trends in cell biology,* 2009, 19(2): 72-80.). However, normal red blood cells are not phagocytosed due to the inhibitory signal generated by the binding of CD47 on the surface of the cell membrane to SIPRα of macrophages. (Oldenborg P A, Zheleznyak A, Fang Y F, et al. Role of CD47 as a marker of self on red blood cells. *Science,* 2000, 288(5473): 2051-2054.). TSP1, a homotrimer composed of 3 peptide chains, is involved in cell proliferation, apoptosis, adhesion, migration, angiogenesis and other processes through interaction with other cell surface receptors, matrix components and growth factors (Jiang P, Lagenaur C F, Narayanan V. Integrin-associated Protein Is a Ligand for the P84 Neural Adhesion Molecule. *Journal of Biological Chemistry* 1999. 274:559-62). Macrophages are derived from monocytes, which in turn are derived from precursor cells in the bone marrow. Their main functions are to phagocytose cell debris and pathogens in the form of fixed cells or free cells and to activate lymphocytes or other immune cells to respond to the pathogens. At present, research suggests that tumor cells have a mechanism of escaping macrophage phagocytosis. During the growth of tumor cells, specific proteins such as calreticulin form on the surface, exposing the identity of the tumor cells, such that the tumor cells are phagocytosed by the attracted macrophages. However, tumor cells with highly expressed CD47 are mistakenly recognized as normal cells by macrophages with SIRPα and thus escape macrophage phagocytosis, since the CD47-SIRPα pathway activates the inhibition of the macrophage phagocytosis (CD47 is upregulated on circulating hematopoietic stein cells and leukemia cells to avoid phagocytosis. Jaiswal S, Jamieson C H M, Pang W W, et al. *Cell,* 2009, 138(3) 271-285).

At present, research suggests that anti-CD47 antibodies kill tumor cells primarily through two mechanisms. 1. Binding of anti-CD47 antibodies to CD47 blocks the CD47-SIRPα pathway, allowing macrophages to perform phagocytosis. 2. Anti-CD47 antibodies exert a tumor-killing effect through DC cells and CD8+ T cells. DC cells phagocytose tumor cells through a synergy between anti-CD47 antibodies and pro-phagocytic molecules such as calreticulin, and present tumor-associated antigens to CD8+ T cells, thereby exerting the specific killing effect of CD8+ T cells on tumors (CD47 blockade as another immune checkpoint therapy for cancer. Vonderheide R H. *Nature Medicine,* 2015, 21(10): 1122). With these two mechanisms, it suggests that anti-CD47 antibodies are very likely to have the ability to activate both non-specific immunity and specific immunity.

At present, anti-CD47 monoclonal antibody drugs have promising utility in a variety of applications and are effective in treating tumors. They can be used for treating various tumors. The anti-CD47 monoclonal antibody drug Hu5F9-G4 can effectively inhibit the growth and metastasis of hematological malignancies and solid tumors in pre-clinical experiments (Abstract PR13: The anti-CD47 antibody Hu5F9-G4 is a novel immune checkpoint inhibitor with synergistic efficacy in combination with clinically active cancer targeting antibodies[J] Chao M P, McKenna K M, Cha A, et al., 2016).

Therefore, the development of antibody medicaments with high affinity for CD47, higher efficacy and fewer toxic side effects for treating tumors is of great significance.

SUMMARY

The inventors used mammalian cell expression systems to express recombinant human CD47 as an antigen to immunize mice, and obtained hybridoma cells by fusion of mouse spleen cells and myeloma cells. The following hybridoma cell lines are obtained by screening a large number of the samples.

The inventors found that:

The hybridoma cell line LT012 can secrete a monoclonal antibody (named 6F7) capable of specifically binding to CD47, and the monoclonal antibody can compete with the receptor SIRPα ECD-hFc-Biotin for binding to CD47, effectively blocking the binding of SIRPα to CD47 and further promoting the phagocytosis of tumor cells by macrophages.

Furthermore, the inventors have prepared humanized monoclonal antibodies 6F7 (named 6F7H1L1, 6F7H2L2 and 6F7H3L3).

The present invention is detailed below.

One aspect of the present invention relates to an antibody or an antigen-binding fragment thereof, wherein the antibody comprises CDR sequences selected from the following CDR sequences contained in heavy chain variable regions and light chain variable regions:

(1) an HCDR1, an HCDR2 and an HCDR3 contained in a heavy chain variable region set forth in SEQ ID NO: 2, and an LCDR1, an LCDR2 and an LCDR3 contained in a light chain variable region set forth in SEQ ID NO: 4; or (2) an HCDR1, an HCDR2 and an HCDR3 contained in a heavy chain variable region set forth in SEQ ID NO: 12, and an LCDR1, an LCDR2 and an LCDR3 contained in a light chain variable region set forth in SEQ ID NO: 14; or (3) an HCDR1, an HCDR2 and an HCDR3 contained in a heavy chain variable region set forth in SEQ ID NO: 16, and an LCDR1, an LCDR2 and an LCDR3 contained in a light chain variable region set forth in SEQ ID NO: 18; or (4) an HCDR1, an HCDR2 and an HCDR3 contained in a heavy chain variable region set forth in SEQ ID NO: 20, and an LCDR1, an LCDR2 and an LCDR3 contained in a light chain variable region set forth in SEQ ID NO: 22;

preferably, the antibody comprises:

an HCDR1 comprising or consisting of a sequence set forth in SEQ ID NO: 5, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence;

an HCDR2 comprising or consisting of a sequence set forth in SEQ ID NO: 6, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence; and an HCDR3 comprising or consisting of a sequence set forth in SEQ ID NO: 7, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence. The antibody further comprises: an LCDR1 comprising or consisting of an amino acid sequence set forth in SEQ ID NO: 8, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence;

an LCDR2 comprising or consisting of an amino acid sequence set forth in SEQ ID NO: 9, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence; and an LCDR3 comprising or consisting of a sequence set forth in SEQ ID NO: 10, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2 or 3) conservative amino acid mutations (preferably substitutions, insertions or deletions) compared to the sequence.

In one embodiment of the present invention, the antibody comprises:

(1) a heavy chain variable region comprising or consisting of:

an amino acid sequence set forth in SEQ ID NO: 2, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 2, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 2, and a light chain variable region comprising or consisting of:

an amino acid sequence set forth in SEQ ID NO: 4, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 4, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 4;

(2) a heavy chain variable region comprising or consisting of:

an amino acid sequence set forth in SEQ ID NO: 12, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 12, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 12; and a light chain variable region comprising or consisting of:

an amino acid sequence set forth in SEQ ID NO: 14, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 14, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 14;

(3) a heavy chain variable region comprising or consisting of:

an amino acid sequence set forth in SEQ ID NO: 16, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 16, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 16; and a light chain variable region comprising or consisting of:

an amino acid sequence set forth in SEQ ID NO: 18, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 18, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 18; and (4) a heavy chain variable region comprising or consisting of:

an amino acid sequence set forth in SEQ ID NO: 20, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 20, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 20; and a light chain variable region comprising or consisting of:

an amino acid sequence set forth in SEQ ID NO: 22, or a sequence having at least 85%, preferably 86%, 87%, 88%, 89%, 90%, 91%, 92%, 93%, 94%, 95%, 96%, 97%, 98% or 99% or more sequence identity to the sequence set forth in SEQ ID NO: 22, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the amino acid sequence set forth in SEQ ID NO: 22.

The amino acid sequences of the CDR regions of the antibodies in (1) to (12) above are analyzed by technical means well known to those skilled in the art, for example, through a VBASE2 database.

The antibodies 6F7, 6F7 H1L1, 6F7 H2L2 and 6F7 H3L3 disclosed herein share the same HCDR1-3 and LCDR1-3.

The amino acid sequences of the 3 CDR regions of the heavy chain variable region are as follows:

```
HCDR1:
                    (SEQ ID NO: 5)
GYTFTSYW,

HCDR2:
                    (SEQ ID NO: 6)
IDPSDSET,
```

-continued

```
and

HCDR3:
                    (SEQ ID NO: 7)
ARLYRWYFDV;
```

the amino acid sequences of the 3 CDR regions of the light chain variable region are as follows:

```
LCDR1:
                    (SEQ ID NO: 8)
EIVGTY,

LCDR2:
                    (SEQ ID NO: 9)
GAS,
and

LCDR3:
                    (SEQ ID NO: 10)
GQSYNFPYT
```

In some embodiments, the antibodies disclosed herein are selected from the group consisting of:

an amino acid sequence of the 6F7 H1L1 (G1M) heavy chain (SEQ ID NO: 59)

an amino acid sequence of the 6F7 H1L1 (G1M) light chain (SEQ ID NO: 60)

an amino acid sequence of the 6F7 H2L2 (G1M) heavy chain (SEQ ID NO: 61)

an amino acid sequence of the 6F7 H2L2 (G1M) light chain (SEQ ID NO: 62)

an amino acid sequence of the 6F7 H3L3 (G1M) heavy chain (SEQ ID NO: 63)

an amino acid sequence of the 6F7 H3L3 (G1M) light chain (SEQ ID NO: 64)

an amino acid sequence of the 6F7 H1L1 (hG4) heavy chain (SEQ ID NO: 65)

an amino acid sequence of the 6F7 H1L1 (hG4) light chain (SEQ ID NO: 66)

an amino acid sequence of the 6F7 H2L2 (hG4) heavy chain (SEQ ID NO: 67)

an amino acid sequence of the 6F7 H2L2 (hG4) light chain (SEQ ID NO: 68)

an amino acid sequence of the 6F7 H3L3 (hG4) heavy chain (SEQ ID NO: 69)

an amino acid sequence of the 6F7 H3L3 (hG4) light chain (SEQ ID NO: 70)

In one embodiment of the present invention, the antibody (preferably 6F7 antibody) further comprises FRs in the heavy chain variable region, preferably the FRs including FR-H1, FR-H2, FR-H3 and FR-H4, wherein the FR-H1 comprises or consists of an amino acid sequence set forth in SEQ ID NO: 23, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 23, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 23; the FR-H2 comprises or consists of an amino acid sequence set forth in SEQ ID NO: 24, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 24, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 24; the FR-H3 comprises or consists of an amino acid sequence set forth in SEQ ID NO: 25, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 25, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 25; and the FR-H4 comprises or consists of an amino acid sequence set forth in SEQ ID NO: 26, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 26, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 26.

In one embodiment of the present invention, the antibody (preferably 6F7 antibody) further comprises FRs in the light chain variable region, preferably the FRs including FR-L1, FR-L2, FR-L3 and FR-L4, wherein the FR-L1 comprises or consists of an amino acid sequence set forth in SEQ ID NO: 27, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 27, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 27; the FR-L2 comprises or consists of an amino acid sequence set forth in SEQ ID NO: 28, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 28, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 28; the FR-L3 comprises or consists of an amino acid sequence set forth in SEQ ID NO: 29, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 29, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 29; and the FR-L4 comprises or consists of an amino acid sequence set forth in SEQ ID NO: 30, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 30, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 30.

In one embodiment of the present invention, the antibody (preferably 6F7 H1L1 antibody) further comprises FRs in the heavy chain variable region, preferably the FRs including FR-H1, FR-H2, FR-H3 and FR-H4, wherein the FR-H1 comprises or consists of an amino acid sequence set forth in SEQ ID NO: 31, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 31, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 31; the FR-H2 comprises or consists of an amino acid sequence set forth in SEQ ID NO: 32, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 32, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 32; the FR-H3 comprises or consists of an amino acid sequence set forth in SEQ ID NO: 33, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 33, or an amino acid sequence having one or more conservative amino acid mutations (preferably substitutions, insertions or deletions) compared to the amino acid sequence set forth in SEQ ID NO: 33; and the FR-H4 comprises or consists of an amino acid sequence set forth in SEQ ID NO: 34, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 34, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 34.

In one embodiment of the present invention, the antibody (preferably 6F7 H1L1 antibody) further comprises FRs in the light chain variable region, preferably the FRs including FR-L1, FR-L2, FR-L3 and FR-L4, wherein the FR-L1 comprises or consists of an amino acid sequence set forth in SEQ ID NO: 35, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 35, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 35; the FR-L2 comprises or consists of an amino acid sequence set forth in SEQ ID NO: 36, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 36, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 36; the FR-L3 comprises or consists of an amino acid sequence set forth in SEQ ID NO: 37, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 37, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 37; and the FR-L4 comprises or consists of an amino acid sequence set forth in SEQ ID NO: 38, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 38, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 38.

In one embodiment of the present invention, the antibody (preferably 6F7 H2L2 antibody) further comprises FRs in the heavy chain variable region, preferably the FRs including FR-H1, FR-H2, FR-H3 and FR-H4, wherein the FR-H1 comprises or consists of an amino acid sequence set forth in SEQ ID NO: 39, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 39, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 39; the FR-H2 comprises or consists of an amino acid sequence set forth in SEQ ID NO: 40, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 40, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 40; the FR-H3 comprises or consists of an amino acid sequence set forth in SEQ ID NO: 41, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 41, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 41; and the FR-H4 comprises or consists of an amino acid sequence set forth in SEQ ID NO: 42, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 42, or an amino acid sequence having one or more conservative amino acid mutations (preferably substitutions, insertions or deletions) compared to the amino acid sequence set forth in SEQ ID NO: 42.

In one embodiment of the present invention, the antibody (preferably 6F7 H2L2 antibody) further comprises FRs in the light chain variable region, preferably the FRs including FR-L1, FR-L2, FR-L3 and FR-L4, wherein the FR-L1 comprises or consists of an amino acid sequence set forth in SEQ ID NO: 43, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 43, or an amino acid sequence having one or more conservative amino acid mutations (preferably substitutions, insertions or deletions) compared to the amino acid sequence set forth in SEQ ID NO: 43; the FR-L2 comprises or consists of an amino acid sequence set forth in SEQ ID NO: 44, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 44, or an amino acid sequence having one or more conservative amino acid mutations (preferably substitutions, insertions or deletions) compared to the amino acid sequence set forth in SEQ ID NO: 44; the FR-L3 comprises or consists of an amino acid sequence set forth in SEQ ID NO: 45, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 45, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 45; and the FR-L4 comprises or consists of an amino acid sequence set forth in SEQ ID NO: 46, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 46, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 46.

In one embodiment of the present invention, the antibody (preferably 6F7 H3L3 antibody) further comprises FRs in the heavy chain variable region, preferably the FRs including FR-H1, FR-H2, FR-H3 and FR-H4, wherein the FR-H1 comprises or consists of an amino acid sequence set forth in SEQ ID NO: 47, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 47, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 47; the FR-H2 comprises or consists of an amino acid sequence set forth in SEQ ID NO: 48, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 48, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 48; the FR-H3 comprises or consists of an amino acid sequence set forth in SEQ ID NO: 49, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 49, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 49; and the FR-H4 comprises or consists of an amino acid sequence set forth in SEQ ID NO: 50, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 50, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 50.

In one embodiment of the present invention, the antibody (preferably 6F7 H3L3 antibody) further comprises FRs in the light chain variable region, preferably the FRs including FR-L1, FR-L2, FR-L3 and FR-L4, wherein the FR-L1 comprises or consists of an amino acid sequence set forth in SEQ ID NO: 51, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 51, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 51; the FR-L2 comprises or consists of an amino acid sequence set forth in SEQ ID NO: 52, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 52, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 52; the FR-L3 comprises or consists of an amino acid sequence set forth in SEQ ID NO: 53, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 53, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 53; and the FR-L4 comprises or consists of an amino acid sequence set forth in SEQ ID NO: 54, a sequence having at least 80%, preferably 81%, 82%, 83%, 84%, 85%, 86%, 87%, 88%, 89%, 90%, 91%, 92%, 93%, 94%, 95%, 96%, 97%, 98% or 99% or more sequence identity to the sequence set forth in SEQ ID NO: 54, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 54.

One aspect of the present invention relates to an isolated polypeptide comprising sequences set forth in SEQ ID NOs: 5, 6 and 7, wherein the polypeptide, as part of an anti-human CD47 antibody, specifically binds to human CD47, the antibody further comprising sequences set forth in SEQ ID NOs: 8, 9 and 10.

One aspect of the present invention relates to an isolated polypeptide comprising sequences set forth in SEQ ID NOs: 8, 9 and 10, wherein the polypeptide, as part of an anti-human CD47 antibody, specifically binds to human CD47, the antibody further comprising sequences set forth in SEQ ID NOs: 5, 6 and 7.

One aspect of the present invention relates to an isolated polypeptide comprising a sequence selected from sequences set forth in SEQ ID NOs: 2, 12, 16 and 20, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence, wherein the polypeptide, as part of an anti-human CD47 antibody, specifically binds to human CD47, the antibody further comprising a sequence selected from sequences set forth in SEQ ID NOs: 4, 14, 18 and 22, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence; or one aspect of the present invention relates to an isolated polypeptide comprising a sequence selected from sequences set forth in SEQ ID NOs: 4, 14, 18 and 22, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence, wherein the polypeptide, as part of an anti-human CD47 antibody, specifically binds to human CD47, the monoclonal antibody further comprising a sequence selected from sequences set forth in SEQ ID NOs: 2, 12, 16 and 20, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence.

In one embodiment of the present invention, the antigen-binding fragment is selected from Fab, Fab', $F(ab')_2$, Fd, Fv, dAb, Fab/c, complementarity determining region (CDR) fragment, single chain antibody (e.g., scFv), bivalent antibody and domain antibody.

In an embodiment of the present invention, the antibody is a humanized antibody, a chimeric antibody or a multi-specific antibody (e.g., a bispecific antibody).

In one embodiment of the present invention, the antibody binds to human CD47 protein with a KD less than about $10^{-5}$ M, e.g., less than about $10^{-6}$ M, $10^{-7}$ M, $10^{-8}$ M, $10^{-9}$ M or $10^{-10}$ M or less. Preferably, the KD is measured by a Fortebio molecular interaction analyzer.

In one embodiment of the present invention, the antibody binds to human CD47 protein with an EC50 less than about 100 nM, e.g., less than about 10 nM, 1 nM, 0.9 nM, 0.8 nM, 0.7 nM, 0.6 nM, 0.5 nM, 0.4 nM, 0.3 nM, 0.2 nM or 0.1 nM or less. Specifically, the EC50 is measured by indirect ELISA.

In one embodiment of the present invention, the antibody comprises constant regions, and the constant regions are derived from species other than murine, e.g., from a human antibody, preferably from a human IgG, more preferably from IgG1 or IgG4.

In one embodiment of the present invention, the constant region of the antibody is humanized, e.g., the heavy chain constant regions are Ig gamma-1 chain C regions, more preferably the Ig gamma-1 chain C region under GenBank ACCESSION No. P01857 (SEQ ID NO: 58), or are Ig gamma-4 chain C regions, more preferably the Ig gamma-4 chain C region under GenBank ACCESSION No. P01861.1 (SEQ ID NO: 56); the light chain constant regions are Ig kappa chain C regions, more preferably the Ig kappa chain C region under GenBank ACCESSION No. P01834 (SEQ ID NO: 57). The antibodies disclosed herein use the following constant regions on the basis of the variable regions of 6F7 H1L1, 6F7 H2L2 and 6F7 H3L3: the heavy chain constant region is Ig gamma-1 chain C region under the ACCESSION No. P01857 (SEQ ID NO: 58) or the heavy chain constant region Ig gamma-4 chain C region under the ACCESSION No. P01861.1 (SEQ ID NO: 56); the light chain constant region is Ig kappa chain C region under the ACCESSION No. P01834 (SEQ ID NO: 57). Another aspect of the present invention relates to an isolated polynucleotide encoding a polypeptide comprising sequences set forth in SEQ ID NOs: 5, 6 and 7, wherein the polypeptide, as part of an anti-human CD47 antibody, specifically binds to human CD47, the antibody further comprising sequences set forth in SEQ ID NOs: 8, 9 and 10.

One aspect of the present invention relates to an isolated polynucleotide encoding a polypeptide comprising sequences set forth in SEQ ID NOs: 8, 9 and 10, wherein the polypeptide, as part of an anti-human CD47 antibody, specifically binds to human CD47, the antibody further comprising sequences set forth in SEQ ID NOs: 5, 6 and 7.

One aspect of the present invention relates to an isolated polynucleotide encoding a polypeptide comprising a sequence selected from sequences set forth in SEQ ID NOs: 2, 12, 16 and 20, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence, wherein the polypeptide, as part of an anti-human CD47 antibody, specifically binds to human CD47, the antibody further comprising a sequence selected from sequences set forth in SEQ ID NOs: 4, 14, 18 and 22, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence; or one aspect of the present invention relates to an isolated polynucleotide encoding a polypeptide comprising a sequence selected from sequences set forth in SEQ ID NOs: 4, 14, 18 and 22, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence, wherein the polypeptide, as part of an anti-human CD47 antibody, specifically binds to human CD47, the antibody further comprising a sequence selected from sequences set forth in SEQ ID NOs: 2, 12, 16 and 20, a sequence having at least 85%, preferably 86%, 87%, 88%, 89%, 90%, 91%, 92%, 93%, 94%, 95%, 96%, 97%, 98% or 99% or more sequence identity to the sequence, or an amino acid sequence having one or more (preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) conservative amino acid mutations (preferably substitutions, insertions or deletions) compared to the sequence.

Specifically, the polynucleotide molecule comprises or consists of a nucleotide sequence set forth in SEQ ID NO: 1, SEQ ID NO: 11, SEQ ID NO: 15 or SEQ ID NO: 19, or a sequence having at least 85%, preferably 86%, 87%, 88%, 89%, 90%, 91%, 92%, 93%, 94%, 95%, 96%, 97%, 98% or 99% or more sequence identity to the sequence.

Specifically, the polynucleotide molecule comprises or consists of a nucleotide sequence set forth in SEQ ID NO: 3, SEQ ID NO: 13, SEQ ID NO: 17 or SEQ ID NO: 21, or a sequence having at least 85%, preferably 86%, 87%, 88%, 89%, 90%, 91%, 92%, 93%, 94%, 95%, 96%, 97%, 98% or 99% or more sequence identity to the sequence.

Yet another aspect of the present invention relates to a vector comprising any one of the polynucleotide molecules disclosed herein as described above.

Yet another aspect of the present invention relates to a host cell comprising any one of the polynucleotide molecules disclosed herein, or the vector disclosed herein as described above.

Yet another aspect of the present invention relates to a method for preparing any one of the antibodies or the antigen-binding fragments thereof disclosed herein as described above, comprising culturing the host cell disclosed herein in a suitable condition, and isolating the antibody or the antigen-binding fragment thereof from the cell cultures.

One aspect of the present invention further provides an antibody conjugate comprising the anti-human CD47 antibody or the antigen-binding fragment thereof, and a conjugated moiety coupled thereto, wherein the conjugated moiety is a purification tag (e.g., a His tag), a cytotoxic agent or a detectable label. Preferably, the conjugated moiety is a radioisotope, a luminescent substance, a colored substance, an enzyme or polyethylene glycol.

One aspect of the present invention further provides a multispecific antibody, preferably a bispecific antibody, comprising the anti-human CD47 antibody or the antigen-binding fragment thereof, and an antibody or an antigen-binding fragment against another antigen and/or another antigenic epitope.

One aspect of the present invention further provides a fusion protein comprising any one of the anti-human CD47 antibodies or the antigen-binding fragments thereof disclosed herein as described above.

One aspect of the present invention further provides a kit comprising any one of the antibodies or the antigen-binding fragments thereof disclosed herein, or comprising the antibody conjugate, the multispecific antibody, or the fusion protein disclosed herein as described above.

Preferably, the kit further comprises a second antibody that specifically identifies the antibody or the antigen-binding fragment thereof; optionally, the second antibody further comprises a detectable label, such as a radioisotope, a luminescent substance, a colored substance, an enzyme or polyethylene glycol.

One aspect of the present invention further provides a hybridoma cell line selected from the hybridoma cell line LT012 under CCTCC NO. 2018135, and a monoclonal antibody produced by the hybridoma cell line.

Yet another aspect of the present invention relates to use of any one of the antibodies or the antigen-binding fragments thereof or the antibody conjugate, the multispecific antibody or the fusion protein disclosed herein as described above in detecting the presence or level of human CD47 in a sample, or in preparing a kit for detecting the presence or level of human CD47 in a sample.

Yet another aspect of the present invention relates to a pharmaceutical composition comprising any one of the antibodies or the antigen-binding fragments thereof disclosed herein as described above or the antibody conjugate, the multispecific antibody or the fusion protein disclosed herein, and optionally, a pharmaceutically acceptable carrier and/or excipient.

Yet another aspect of the present invention relates to use of any one of the antibodies or the antigen-binding fragments thereof disclosed herein as described above or the antibody conjugate, the multispecific antibody or the fusion protein disclosed herein in preparing:

- a medicament for blocking the binding of human CD47 to human SIRPα,
- a medicament for blocking the activity of human CD47 or down-regulating the level of human CD47, or
- a medicament for blocking cellular response mediated by the binding of human SIRPα to CD47.

One aspect of the present invention relates to use of any one of the antibodies or the antigen-binding fragments thereof as described above or the antibody conjugate, the multispecific antibody or the fusion protein disclosed herein in the treatment of a tumor or in the preparation of a medicament for the treatment of a tumor.

Yet another aspect of the present invention relates to an in vivo or in vitro method comprising administering a cell comprising the antibody or the antigen-binding fragment thereof disclosed herein, the antibody conjugate, the multispecific antibody or the fusion protein disclosed herein, or administering to a subject in need an effective amount of any one of the antibodies or the antigen-binding fragments thereof as described above or the antibody conjugate, the multispecific antibody or the fusion protein disclosed herein. The method is selected from:

- a method for blocking the binding of CD47 to human SIRPα,
- a method for blocking the activity of human CD47 or down-regulating the level of human CD47, and
- a method for blocking cellular response mediated by the binding of human SIRPα to CD47.

In one embodiment of the present invention, the in vitro method is for non-therapeutic and/or non-diagnostic purposes.

Yet another aspect of the present invention relates to use of any one of the antibodies or the antigen-binding fragments thereof disclosed herein or the antibody conjugate, the multispecific antibody or the fusion protein disclosed herein as described above in the prevention and/or treatment and/or adjuvant treatment and/or diagnosis of a relevant tumor or in the preparation of a medicament for the prevention and/or treatment and/or adjuvant treatment and/or diagnosis of a relevant tumor.

In one aspect of the present invention, the tumor is preferably a tumor expressing CD47, preferably cancer, e.g., a hematological malignancy or a solid tumor, more preferably lymphoma, colon cancer or breast cancer, more preferably non-Hodgkin lymphoma, and even more preferably B cell lymphoma cells.

In one embodiment of the present invention, the medicament is in a form suitable for injection, preferably in a form suitable for administration by subcutaneous injection, intradermal injection, intravenous injection, intramuscular injection or intralesional injection.

In the present invention, unless otherwise defined, the scientific and technical terms used herein have the meanings generally understood by those skilled in the art. In addition, the laboratory operations of cell culture, molecular genetics, nucleic acid chemistry and immunology used in the present invention are the routine operations widely used in the corresponding fields. Meanwhile, in order to better understand the present invention, the definitions and explanations of the relevant terms are provided below.

As used herein, the term "antigen-binding region" means a protein or a portion of a protein that specifically binds to a given antigen. For example, a portion of an antibody comprising amino acid residues that interact with an antigen and confer the antibody the specificity and affinity for the antigen is referred to as an "antigen-binding region". The antigen-binding region generally comprises one or more "complementarity-determining regions" (CDRs). Certain antigen-binding regions further comprise one or more "framework" regions (FRs). CDRs are amino acid sequences that contribute to antigen binding specificity and affinity.

As used herein, the term "antibody" refers to an intact immunoglobulin of any isotype or an antigen-binding fragment thereof that can compete with an intact antibody for specifically binding to a target antigen, and includes, for example, chimeric, humanized, fully humanized, and bispecific antibodies or antigen-binding fragments thereof. Such "antibodies" are antigen-binding proteins. An intact antibody generally comprises at least two full-length heavy chains and two full-length light chains, but, in some cases, may comprise fewer chains, such as an antibody naturally occurring in camelids that may comprise only a heavy chain. An antibody or an antigen-binding fragment thereof may be derived from a single source only, or may be "chimeric", i.e., different portions of an antibody may be derived from two different sources as further described below. An antibody or an antigen-binding fragment thereof may be produced in hybridomas by recombinant DNA technology, or by enzymatic or chemical cleavage of intact antibodies. Unless otherwise indicated, the term "antibody", in addition to antibodies comprising two full-length heavy chains and two full-length light chains, also includes derivatives, variants and fragments thereof.

As used herein, the term "antigen-binding fragment" (or abbreviated as "fragment") of an "antibody" or an "immunoglobulin chain" (heavy or light chain) comprises part of an antibody (whether obtained or synthesized) that lacks at least some of the amino acids present in the full length of the antibody but is capable of specifically binding to the antigen. Such fragments are biologically active as they specifically bind to a target antigen and can compete with other antibodies or antigen-binding fragments thereof for specifically binding to a given epitope. In one aspect, such fragments will retain at least one CDR present in the full-length light or heavy chain of the antibody, and in some embodiments, will comprise a single heavy and/or light chain or a portion thereof. Such biologically active fragments can be produced by recombinant DNA technology, or, for example, by enzymatic or chemical cleavage of intact antibodies. Immunologically functional immunoglobulin fragments include, but are not limited to, Fab, Fab', $F(ab')_2$, Fab/c, dAb, Fv, domain antibodies, and single-chain antibodies, and can be derived from any mammalian source, including, but not limited to, human, mouse, rat, camelid, and rabbit. It is further contemplated that a functional portion of an antibody disclosed herein, such as one or more CDRs, can be covalently bound to a second protein or a small molecule to generate a therapeutic agent directed to a particular target in the body, thereby having bifunctional therapeutic properties or having an extended serum half-life, such as a fusion protein.

As used herein, the terms "antibody full-length chain", "full-length antibody", "intact antibody" and "whole antibody" are used interchangeably herein to refer to an antibody having a substantially similar structure to a natural antibody structure or having a heavy chain in Fc region as defined herein.

The term "light chain" includes full-length light chains and fragments thereof with sufficient variable region sequences to confer the binding specificity. The full-length light chain comprises a variable region domain $V_L$ and a constant region domain $C_L$. The variable region domain of the light chain is at the amino terminus of the polypeptide. Light chains include kappa (κ) and lambda (λ) chains.

The term "heavy chain" includes full-length heavy chains and fragments thereof with sufficient variable region sequences to confer the binding specificity. The full-length heavy chain includes a variable region domain $V_H$ and 3 constant region domains $C_{H1}$, $C_{H2}$ and $C_{H3}$. The $V_H$ domain is at the amino terminus of the polypeptide, and the $C_H$ domains are at the carboxyl terminus, the $C_{H3}$ being closest to the carboxyl terminus of the polypeptide. The heavy chain may be of any isotype, including IgG (including IgG1, IgG2, IgG3 and IgG4 subtypes), IgA (including IgA1 and IgA2 subtypes), IgM and IgE.

As used herein, the term "Fab fragment" consists of one light chain, $C_{H1}$ and the variable region of one heavy chain. The heavy chain of a Fab molecule cannot form disulfide bonds with another heavy chain molecule.

As used herein, the term "Fc" region comprises two heavy chain fragments comprising the $C_{H1}$ and $C_{H2}$ domains of an antibody. The two heavy chain fragments are held together by two or more disulfide bonds and by the hydrophobic interaction of the $C_{H3}$ domains.

As used herein, the term "Fab' fragment" comprises one light chain and part of one heavy chain (containing the $V_H$ domain, the $C_{H1}$ domain, and part of the region between the $C_{H1}$ and $C_{H2}$ domains), such that interchain disulfide bonds can be formed between the two heavy chains of two Fab' fragments to form a $F(ab')_2$ molecule.

As used herein, the term "$F(ab')_2$ fragment" comprises two light chains and two heavy chains containing part of the constant region between the $C_{H1}$ and $C_{H2}$ domains, such that interchain disulfide bonds are formed between the two heavy chains. Thus, the $F(ab')_2$ fragment consists of two Fab' fragments held together by disulfide bonds between the two heavy chains.

As used herein, the term "Fv region" comprises the variable regions from the heavy and light chains, but lacks the constant regions.

As used herein, the term "Fd" fragment refers to an antibody fragment consisting of $V_H$ and $C_{H1}$ domains (Ward et al., *Nature,* 341:544-546 (1989)).

As used herein, the term "dAb" fragment consists of $V_H$ domains (Ward et al., *Nature* 341:544-546 (1989)).

As used herein, the term "Fab'-SH" is the designation herein for Fab', wherein one or more cysteine residues of the constant domain carry a free thiol group.

As used herein, the term "Fab/c" fragment is an intermediate formed by pepsin digestion of an immunoglobulin, and combines the advantages of Fab and Fc regions, i.e., strong diffusibility and low metabolic clearance in vivo, while retaining high affinity (Liu Jianjun, *Chinese Journal of Cellular and Molecular Immunology,* 1989(4):29-29).

As used herein, the term "single-chain antibody" is an Fv molecule in which the heavy and light chain variable regions are connected by a flexible linker to form a single polypeptide chain (which forms an antigen binding region) (see, e.g., Bird et al., *Science,* 242:423-426 (1988), and Huston et al., *Proc. Natl. Acad. Sci*., USA, 90:5879-5883 (1988)). Single-chain antibodies are described in detail in International Patent Publication No. WO 88/01649 and U.S. Pat. Nos. 4,946,778 and 5,260,203, the disclosures of which are incorporated herein by reference.

As used herein, the term "domain antibody" is an immunofunctional immunoglobulin fragment that comprises only the variable region of the heavy chain or the light chain, including multivalent domain antibodies or bivalent domain antibodies. In some cases, two or more $V_H$ regions are covalently linked by a peptide linker to generate a multivalent domain antibody (particularly a bivalent domain antibody). The two $V_H$ regions of the bivalent domain antibody may target the same or different antigens.

As used herein, the term "bivalent antigen-binding protein" or "bivalent antibody" comprises two antigen-binding sites. In some cases, the two binding sites have the same antigen specificity. The bivalent antibody may be bispecific.

As used herein, the term "multispecific antigen-binding protein" or "multispecific antibody" is an antigen-binding protein or antibody that targets more than one antigen or epitope.

As used herein, the term "bispecific", "dual-specificity" or "bifunctional" antigen-binding protein or antibody is a hybrid antigen-binding protein or antibody having two different antigen-binding sites, respectively. A bispecific antibody is a multispecific antigen-binding protein or a multispecific antibody, and can be produced by a variety of methods, including but not limited to, fusion of hybridomas or linkage of Fab' fragments. See, e.g., Songsivilai and Lachmann, 1990*, Clin. Exp. Immunol.,* 79:315-321; Kostelny et al., 1992*, J. Immunol.,* 148:1547-1553. The two binding sites of a bispecific antigen-binding protein or antibody will bind to two different epitopes present in the same or different protein targets.

As used herein, the terms "mAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody is highly specific for a single epitope on an antigen. The polyclonal antibody, relative to the monoclonal antibody, generally comprises at least two or more different antibodies which generally recognize different epitopes on an antigen. Monoclonal antibodies can generally be obtained using hybridoma technique first reported by Kohler et al. (*Nature,* 256:495, 1975), but can also be obtained using recombinant DNA technology (see, e.g., U.S. Pat. No. 4,816,567).

As used herein, the term "humanized antibody" refers to an antibody or an antibody fragment obtained when all or part of the CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, for example, Jones et al., *Nature,* 321:522-525 (1986); Reichmann et al., *Nature,* 332:323-329 (1988); Presta, *Curr. Op. Struct. Biol.,* 2:593-596 (1992); and *Clark, Immunol. Today,* 21:397-402 (2000).

As used herein, the term "epitope" refers to a site on an antigen to which an immunoglobulin or an antibody specifically binds. "Epitope" is also referred to in the field as an "antigenic determinant". The epitope or antigenic determinant generally consists of chemically active surface groups of molecules such as amino acids, carbohydrates or sugar side chains, and usually has specific three-dimensional structural characteristics and specific charge characteristics. For example, the epitope generally comprises at least 3, 4, 5, 6, 7, 8, 9, 10, 11, 12, 13, 14, or 15 consecutive or non-consecutive amino acids in a unique spatial conformation, which can be "linear" or "conformational". See, e.g., Epitope Mapping Protocols in Methods in Molecular Biology, Vol. 66, G. E. Morris, Ed. (1996). In a linear epitope, all interaction sites between a protein and an interaction molecule (e.g., an antibody) are located linearly along the primary amino acid sequence of the protein. In a conformational epitope, the interaction sites are located across amino acid residues of a protein that are separated from each other.

The terms "polypeptide" or "protein" are used interchangeably herein to refer to a polymer of amino acid residues. The term is also used to refer to an amino acid polymer in which one or more amino acid residues are analogs or mimetics of naturally occurring amino acids, and for naturally occurring amino acid polymers. The term may also include, for example, amino acid polymers that have been modified by addition of saccharide residues to form glycoproteins, or have been phosphorylated. Polypeptides and proteins can be produced by naturally existing cells and non-recombinant cells, or they may be produced by genetically engineered or recombinant cells, and comprise a molecule having the amino acid sequence of a native protein or a molecule having deletions, insertions and/or substitutions in one or more amino acids of the native sequence.

In some embodiments, the terms "polypeptide" and "protein" particularly include antibodies, such as anti-human CD47 antibodies (also referred to as CD47 antibodies), CD47-binding proteins, or variants thereof, e.g., antibodies or sequences having deletions, insertions, and/or substitutions of one or more amino acids.

The term "polypeptide fragment" refers to a polypeptide having an amino-terminal deletion, a carboxyl-terminal deletion, and/or an internal deletion as compared to a full-length protein. Such fragments may also comprise modified amino acids as compared to the full-length protein. In certain embodiments, such fragments are about 5 to 500 amino acids in length. For example, a fragment can be at least 5, 6, 8, 10, 14, 20, 50, 70, 100, 110, 150, 200, 250, 300, 350, 400 or 450 amino acids in length. Useful polypeptide fragments include immunologically functional fragments of antibodies, including binding domains. In the case of human CD47 antibodies, useful fragments include but are not limited to CDR regions, variable domains of heavy or light chains, parts of antibody chains, variable domains exactly comprising 2 CDRs, or the like.

A "derivative" of a polypeptide is a polypeptide (e.g., an antigen-binding protein or an antibody) that is chemically modified in other manners than insertion, deletion or substitution, e.g., by conjugation with another chemical moiety, e.g., a PEG-conjugated polypeptide.

As used herein, the term "isolated" refers to being obtained by artificial means from a natural state. If a certain "isolated" substance or component appears in nature, it may be the case that change occurs in its natural environment, or that it is isolated from the natural environment, or both. For example, a certain non-isolated polynucleotide or polypeptide naturally occurs in a certain living animal, and the same polynucleotide or polypeptide with high purity isolated in such a natural state is referred to as an isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows for the expression of the protein encoded by the inserted polynucleotide, the vector is referred to as an expression vector. The vector can be introduced into a host cell by transformation, transduction, or transfection so that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages; and animal viruses. Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may comprise a variety of elements that control expression, including, but not limited to promoter sequences, transcription initiation sequences, enhancer sequences, selection elements, and reporter genes. In addition, the vector may further comprise a replication initiation site.

As used herein, the term "host cell" refers to cells to which vectors can be introduced, including, but not limited to, prokaryotic cells such as *E. coli* or *B. subtilis*, fungal cells such as yeast cells or *aspergillus*, insect cells such as S2 drosophila cells or Sf9, or animal cells such as fibroblasts, CHO cells, COS cells, NSO cells, HeLa cells, BHK cells, HEK 293 cells, or human cells.

As used herein, the term "specifically bind" refers to a non-random binding reaction between two molecules, such as a reaction between an antibody and an antigen it targets. In some embodiments, an antibody that specifically binds to an antigen (or an antibody that is specific for an antigen) refers to that the antibody binds to the antigen with an affinity ($K_D$) of less than about $10^{-5}$ M, such as less than about $10^{-6}$ M, $10^{-7}$ M, $10^{-8}$ M, $10^{-9}$ M or $10^{-10}$ M or less.

As used herein, the term "$K_D$" refers to a dissociation equilibrium constant for a specific antibody-antigen interaction, which is used to describe the binding affinity between the antibody and the antigen. Among several parameters measured by molecular binding kinetics, the $K_D$ value is the dissociation equilibrium constant. In antibody medicament research, it is the parameter characterizing the level of the affinity between an antibody of interest and the target antigen molecule, and is calculated as $KD=k_{dis}/k_{on}$. A smaller equilibrium dissociation constant indicates a tighter antibody-antigen binding and a higher affinity between the antibody and the antigen. $k_{on}$ (association rate constant) is the rate of antigen-antibody complex formation, and a smaller $k_{on}$ suggests a faster binding of an antibody to an antigen. $k_{dis}$ (dissociation rate constant) is the rate at which an antibody dissociates from an antigen-antibody complex, and a smaller $k_{dis}$ suggests a slower rate for the antibody dissociating from the antigen and a firmer binding between the antibody and the antigen. Generally, an antibody binds to an antigen (e.g., L1 protein) with a dissociation equilibrium constant ($K_D$) of less than about $10^{-5}$ M, such as less than about $10^{-6}$ M, $10^{-7}$ M, $10^{-8}$ M, $10^{-9}$ M or $10^{-10}$ M or less, for example, as determined on a BIACORE surface plasmon resonance (SPR) instrument or a Fortebio molecular interaction instrument.

As used herein, the terms "monoclonal antibody" and "McAb" have the same meaning and can be used interchangeably; the terms "polyclonal antibody" and "PcAb" have the same meaning and can be used interchangeably; the terms "polypeptide" and "protein" have the same meaning and can be used interchangeably. Besides, herein, amino acids are generally represented by single-letter and three-letter abbreviations known in the art. For example, alanine can be represented by A or Ala.

As used herein, the terms "hybridoma" and "hybridoma cell line" can be used interchangeably, and when referring to the terms "hybridoma" and "hybridoma cell line", subclones and progeny cells of the hybridoma are also included.

As used herein, the terms "percent sequence identity" and "percent sequence homology" are used interchangeably.

As used herein, the terms "similarity", "sequence similarity" and "identity" refer to the correlation between the sequences of two or more protein or polypeptide molecules, as determined by aligning and comparing the sequences. "Percent identity" refers to the percentage of identical amino acid residues in the molecules compared, and can be calculated based on the size of the smallest molecule to be compared. For such calculations, gaps in the alignment (if any) must be addressed by a particular mathematical model or computer program (i.e., an "algorithm"). The term "substantial identity", when used for polypeptides, means that two peptide sequences, when optimally aligned, for example using the programs GAP or BESTFIT, using default gap weights provided by the programs, have at least 70%, 75% or 80% sequence identity, at least 90% or 95% sequence identity, or at least 97%, 98% or 99% sequence identity. In some cases, residue positions that are not identical differ in conservative amino acid substitutions. "Conservative amino acid substitution" is one in which the amino acid residue is substituted with another amino acid residue having a side chain R group that possesses similar chemical properties (e.g., charge or hydrophilicity). Generally, conservative amino acid substitutions will substantially retain the functions and properties of the protein. In cases where two or more amino acid sequences differ from each other by conservative substitutions, the percent sequence identity may be elevated to correct for the conservative nature of the substitution. Methods for making this adjustment are well known to those skilled in the art. See, e.g., Pearson, *Methods Mol. Biol.,* 243:307-31 (1994). Examples of groups of amino acids having side chains with similar chemical properties include: 1) aliphatic hydroxyl side chain: glycine, alanine, valine, leucine and isoleucine, 2) aliphatic hydroxyl side chain: serine and threonine, 3) amide-containing side chain: asparagine and glutamine, 4) aromatic side chain: phenylalanine, tyrosine and tryptophan, 5) basic side chain: lysine, arginine and histidine, 6) acidic side chain: aspartic acid and glutamic acid, and 7) sulfur-containing side chain: cysteine and methionine. For example, the conservative amino acid substitution groups are valine-leucine-isoleucine-glycine-alanine, phenylalanine-tyrosine, threonine-serine, lysine-arginine, glutamic acid-aspartic acid and asparagine-glutamine.

Optionally, conservative substitution is any change with a positive value in the PAM250 log-likelihood matrix disclosed in Gonnet et al., *Science,* 256:1443-45 (1992), which is incorporated herein by reference. A "moderately conservative" substitution is any change with a non-negative value in the PAM250 log-likelihood matrix.

Sequence identity of polypeptides is usually measured by sequence analysis software. Protein analysis software matches sequences using a measure of similarity assigned to different substitutions, deletions and other modifications (including conservative amino acid substitutions). For example, GCG, including programs such as "Gap" and "Bestfit" which (using default parameters specified by the program) can be used to determine sequence homology or sequence identity between closely related polypeptides (e.g., homologous polypeptides from different biological species) or between a wild-type protein and its mutant protein. See, e.g., GCG Version 6.1 (University of Wisconsin, WI). Polypeptide sequences can also be compared using FASTA with default or recommended parameters. See GCG Version 6.10 FASTA (e.g., FASTA2 and FASTA3) which provides alignments for regions of optimal overlap between the challenge and query sequences and percent sequence identities (Pearson, Methods Enzymol. 183:63-98 (1990); Pearson, Methods Mol. Biol., 132:185-219 (2000)). Another preferred algorithm when comparing sequences with a database containing massive sequences from different organisms is the computer program BLAST, in particular, blastp or tblastn (using default parameters provided by the program). See, e.g., Altschul et al., *Mol. Biol.,* 215:403-410 (1990); Al tschul et al., *Nucleic Acids Res.,* 25:3389-402 (1997). Compared with the prior art, the present invention has the following advantages:

The anti-CD47 monoclonal antibody involved herein can effectively block the binding of SIRPα to CD47 by specifically binding to CD47, thereby promoting the phagocytosis of tumor cells by macrophages. The affinity of the antibody (such as 6F7 H1L1) disclosed herein for CD47 of tumor cells is comparable to that of a control antibody Hu5F9-G4, while the affinity for normal human RBCs is lower than that of the control antibody Hu5F9-G4. Therefore, the antibody disclosed herein has better potential for treating tumors on the basis of avoiding affecting normal human red blood cells as much as possible.

NOTES ON THE DEPOSIT OF BIOLOGICAL MATERIALS

Figure 1:
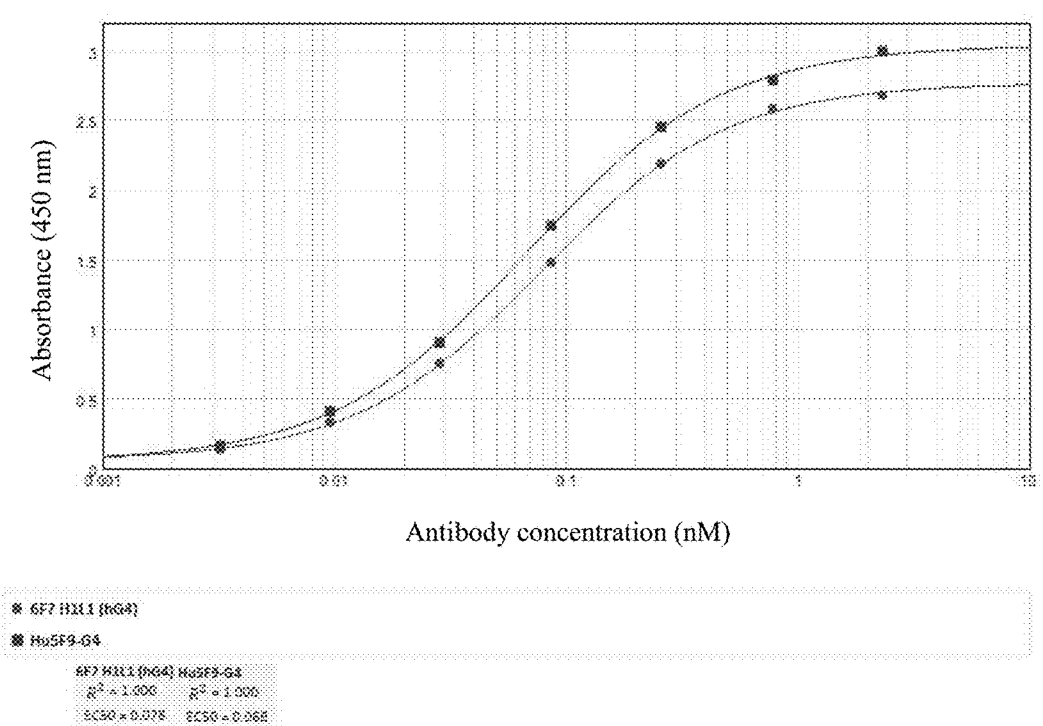
FIG. 1 shows the results of an assay for the binding activity of 6F7 H1L1(hG4) to human CD47 IgV TEV-His.

Hybridoma cell line LT012 was deposited at China Center for Type Culture Collection (CCTCC) on Jun. 21, 2018 under CCTCC NO. C2018135, the depository address being Wuhan University, Wuhan, China, postal code: 430072.

DETAILED DESCRIPTION

The embodiments of the present invention will be described in detail below with reference to the examples. Those skilled in the art will understand that the following examples are only for illustrating the present invention, and should not be construed as limitations on the scope of the present invention. In the cases where the techniques or conditions are not specified, the examples were implemented according to the techniques or conditions described in the literature in the art (e.g., see, *Molecular Cloning: A Laboratory Manual*, authored by J. Sambrook et al., and translated by Huang Peitang et al., Third Edition, Science Press) or according to the product manual. Reagents or instruments used are commercially available conventional products if the manufacturers thereof are not specified.

In the following examples of the present invention, BALB/C mice were purchased from Guangdong Medical Laboratory Animal Center.

The control antibody medicament used was Hu5F9-G4 (synthesized by Zhongshan Akeso Biopharma Ltd., using the sequence of the CD47 antibody Hu5F9-G4 from Forty Seven, Inc., i.e., using SEQ ID NO:37 of US20150183874 as the heavy chain variable region, SEQ ID NO:42 as the light chain variable region, and Ig gamma-4 chain constant region (GenbankID: P01861.1)).

Example 1: Preparation of Anti-Human CD47 Antibody 6F7

1. Preparation of Hybridoma Cell Line 6F7

The antigens used for preparing the anti-CD47 antibody of the hybridoma cell line 6F7 was CD47 IgV TEV-His (including human CD47 mature peptide of positions 19-141 of GenbankID: NP 942088.1 and TEV (amino acid sequence: ENLYFQG, SEQ ID NO: 74)-his tag fusion protein, synthesized by Zhongshan Akeso Biopharma Ltd.) and 3T3-CD47 cells (NIH/3T3, manufacturer: ATCC, Cat. No: CRL-1658; the human CD47 mature peptide was transfected into the cells on the basis of NIH/3T3 to construct a 3T3-CD47 stable expression line). Spleen cells of immunized mice were fused with myeloma cells of the mice to prepare hybridoma cells. With CD47 IgV TEV-His and 3T3-CD47 cells separately taken as antigens, the hybridoma cells were screened by indirect ELISA to obtain hybridoma cells capable of secreting antibodies capable of specifically binding to CD47. The hybridoma cells obtained by ELISA screening were screened by competitive ELISA to obtain a hybridoma cell line capable of secreting a monoclonal antibody capable of competing for binding to CD47 IgV TEV-His with the receptor human SIRPαECD-hFc-Biotin (SIRPαECD refers to an extracellular region of SIRPα, positions 31-373 of protein GenBank Accession No. NP_542970.1; hFc refers to a human IgG Fc purification label, specifically to Ig gamma-1 chain C region, positions 114-330 of GenbankID: P01857), which was then subjected to limiting dilution to obtain a stable hybridoma cell line. The hybridoma cell line was designated hybridoma cell line LT012, and the monoclonal antibody secreted by it was designated 6F7.

Hybridoma cell line LT012 (CD47-6F7) was deposited at China Center for Type Culture Collection (CCTCC) on Jun. 21, 2018 under CCTCC NO. C2018135, the depository address being Wuhan University, Wuhan, China, postal code: 430072.

2. Preparation of Anti-CD47 Antibody 6F7

The cell lines LT011, LT012 and LT015 prepared above were separately cultured with a chemical defined medium (CD medium; containing 1% streptomycin) in a 5% $CO_2$, 37° C. incubator. After 7 days, the supernatants were collected and purified by high-speed centrifugation and vacuum filtration through a microfiltration membrane, and through a HiTrap protein A HP column to obtain antibody 6F7.

Example 2: Sequence Analysis of Anti-CD47 Antibody 6F7 mRNA was extracted from the cell line LT012 cultured in Example 1 according to the method described in the manual of RNAprep pure Cell/Bacteria Kit (Tiangen, Cat. No. DP430).

cDNA was synthesized according to the manual of Invitrogen SuperScript® III First-Strand Synthesis System for RT-PCR and amplified by PCR.

The PCR-amplified products were directly subjected to TA cloning according to the manual of the pEASY-T1 Cloning Kit (Transgen CT101).

The TA-cloned products were directly sequenced, and the sequencing results are as follows:

The nucleic acid sequence of the heavy chain variable region is set forth in SEQ ID NO: 1 with a length of 351 bp.

The encoded amino acid sequence is set forth in SEQ ID NO: 2 with a length of 117 amino acids, and the sequences of heavy chain CDR1, CDR2 and CDR3 are set forth in SEQ ID NOs: 5, 6 and 7, respectively.

The nucleic acid sequence of the light chain variable region is set forth in SEQ ID NO: 3 with a length of 321 bp.

The encoded amino acid sequence is set forth in SEQ ID NO: 4 with a length of 107 amino acids, and the sequences of light chain CDR1, CDR2 and CDR3 are set forth in SEQ ID NOs: 8, 9 and 10, respectively.

Example 3: Design and Preparation of Light and Heavy Chains of Humanized Anti-Human CD47 Antibodies 6F7 H1L1(hG4), 6F7 H2L2(hG4) and 6F7 H3L3(hG4)

1. Design of Light and Heavy Chains of Humanized Anti-Human CD47 Antibodies 6F7 H1L1(hG4), 6F7 H2L2(hG4) and 6F7 H3L3(hG4)

Based on the three-dimensional crystal structure of human CD47 protein (Hage T, Reinemer P, Sebald W., Crystals of a 1:1 Complex Between Human Interleukin-4 and the Extracellular Domain of Its Receptor Alpha Chain, *Eur. J. Biochem.,* 1998; 258(2):831-6.) and the sequence of antibody 6F7 obtained in Example 2, the variable region sequences of antibodies 6F7H1L1, 6F7 H2L2 and 6F7 H3L3 were obtained by computer modeling and mutation design (antibody constant region sequences from NCBI database: the heavy chain constant region is Ig gamma-4 chain C region, ACCESSION No. P01861.1; the light chain constant region is Ig kappa chain C region, ACCESSION No. P01834).

The designed variable region sequences are as follows:

(1) Heavy and Light Chain Variable Region Sequences of Humanized Monoclonal Antibody 6F7 H1L1

The nucleic acid sequence of the heavy chain variable region is set forth in SEQ ID NO: 11 with a length of 351 bp.

The encoded amino acid sequence is set forth in SEQ ID NO: 12 with a length of 117 amino acids, and the sequences of heavy chain CDR1, CDR2 and CDR3 are set forth in SEQ ID NOs: 5, 6 and 7, respectively.

The nucleic acid sequence of the light chain variable region is set forth in SEQ ID NO: 13 with a length of 321 bp.

The encoded amino acid sequence is set forth in SEQ ID NO: 14 with a length of 107 amino acids, and the sequences of light chain CDR1, CDR2 and CDR3 are set forth in SEQ ID NOs: 8, 9 and 10, respectively.

(2) Heavy and Light Chain Variable Region Sequences of Humanized Monoclonal Antibody 6F7 H2L2

The nucleic acid sequence of the heavy chain variable region is set forth in SEQ ID NO: 15 with a length of 351 bp.

The encoded amino acid sequence is set forth in SEQ ID NO: 16 with a length of 117 amino acids, and the sequences of heavy chain CDR1, CDR2 and CDR3 are set forth in SEQ ID NOs: 5, 6 and 7, respectively.

The nucleic acid sequence of the light chain variable region is set forth in SEQ ID NO: 17 with a length of 321 bp.

The encoded amino acid sequence is set forth in SEQ ID NO: 18 with a length of 107 amino acids, and the sequences of light chain CDR1, CDR2 and CDR3 are set forth in SEQ ID NOs: 8, 9 and 10, respectively.

(3) Heavy and Light Chain Variable Region Sequences of Humanized Monoclonal Antibody 6F7 H3L3

The nucleic acid sequence of the heavy chain variable region is set forth in SEQ ID NO: 19 with a length of 351 bp.

The encoded amino acid sequence is set forth in SEQ ID NO: 20 with a length of 117 amino acids, and the sequences of heavy chain CDR1, CDR2 and CDR3 are set forth in SEQ ID NOs: 5, 6 and 7, respectively.

The nucleic acid sequence of the light chain variable region is set forth in SEQ ID NO: 21 with a length of 321 bp.

The encoded amino acid sequence is set forth in SEQ ID NO: 22 with a length of 107 amino acids, and the sequences of light chain CDR1, CDR2 and CDR3 are set forth in SEQ ID NOs: 8, 9 and 10, respectively.

2. Preparation of Humanized Antibodies 6F7 H1L1(hG4), 6F7 H2L2(hG4) and 6F7 H3L3(hG4)

The heavy chain constant regions are Ig gamma-4 chain C region, ACCESSION: P01861.1; the light chain constant regions are Ig kappa chain C region, ACCESSION: P01834.

Heavy chain cDNA and light chain cDNA of 6F7 H1L1 (hG4), heavy chain cDNA and light chain cDNA of 6F7 H2L2(hG4), and heavy chain cDNA and light chain cDNA of 6F7 H3L3(hG4) were separately cloned into pUC57simple (provided by Genscript) vectors to obtain pUC57simple-6F7H1, pUC57simple-6F7L1; pUC57simple-6F7H2, pUC57simple-6F7L2; and pUC57simple-6F7H3, pUC57simple-6F7L3, respectively. With reference to the standard techniques described in *Molecular Cloning: A Laboratory Manual* (Second Edition), the heavy and light chain full-length genes synthesized by EcoRI&HindIII digestion of genes were subcloned into expression vector pcDNA3.1 by restricting EcoRI&HindIII digestion to obtain expression plasmids pcDNA3.1-6F7H1, pcDNA3.1-6F7L1, pcDNA3.1-6F7H2, pcDNA3.1-6F7L2, pcDNA3.1-6F7H3 and pcDNA3.1-6F7L3, and the heavy and light chain genes of the recombinant expression plasmids were further sequenced. Then the designed gene combinations comprising corresponding light and heavy chain recombinant plasmids (pcDNA3.1-6F7H1/pcDNA3.1-6F7L1, pcDNA3.1-6F7H2/pcDNA3.1-6F7L2, and pcDNA3.1-6F7H3/pcDNA3.1-6F7L3) were separately co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column (MabSelect SURE (GE)) to obtain humanized antibodies.

Example 4: Design and Preparation of Light and Heavy Chains of Humanized Anti-Human CD47 Antibodies 6F7 H1L1(G1M), 6F7 H2L2(G1M) and 6F7 H3L3(G1M)

1. Design of Light and Heavy Chains of Humanized Anti-Human CD47 Antibodies 6F7 H1L1(G1), 6F7 H2L2(G1) and 6F7 H3L3(G1)

Based on the three-dimensional crystal structure of human CD47 protein (Hage T, Reinemer P, Sebald W., Crystals of a 1:1 Complex Between Human Interleukin-4 and the Extracellular Domain of Its Receptor Alpha Chain, *Eur. J. Biochem.,* 1998; 258(2):831-6.) and the sequence of antibody 6F7 obtained in Example 2, the variable region sequences of antibodies 6F7H1L1, 6F7 H2L2 and 6F7 H3L3 were obtained by computer modeling and mutation design (antibody constant region sequences from NCBI database: the heavy chain constant region is Ig gamma-1 chain C region, ACCESSION No. P01857; the light chain constant region is Ig kappa chain C region, ACCESSION No. P01834). In order to be distinguished from the humanized antibodies in Example 3, the humanized antibodies above were designated 6F7 H1L1(G1), 6F7 H2L2(G1) and 6F7 H3L3(G1).

The variable region sequences of the humanized antibodies 6F7 H1L1(G1), 6F7 H2L2(G1) and 6F7 H3L3(G1) designed in this example were identical to those of 6F7 H1L1(hG4), 6F7 H2L2(hG4) and 6F7 H3L3(hG4) in Example 3.

2. Preparation of Humanized Antibodies 6F7 H1L1(G1), 6F7 H2L2(G1) and 6F7 H3L3(G1)

The heavy chain constant regions were all Ig gamma-1 chain C region, ACCESSION: P01857; the light chain constant regions were all Ig kappa chain C region, ACCESSION: P01834.

Heavy chain cDNA and light chain cDNA of 6F7 H1L1, heavy chain cDNA and light chain cDNA of 6F7 H2L2, and heavy chain cDNA and light chain cDNA of 6F7 H3L3 were separately cloned into pUC57simple (provided by Genscript) vectors to obtain pUC57simple-6F7H1, pUC57simple-6F7L1; pUC57 simple-6F7H2, pUC57simple-6F7L2; and pUC57simple-6F7H3, pUC57simple-6F7L3, respectively. With reference to the standard techniques described in *Molecular Cloning: A Laboratory Manual* (Second Edition), the heavy and light chain full-length genes synthesized by EcoRI&HindIII digestion of genes were subcloned into expression vector pcDNA3.1 by restricting EcoRI&HindIII digestion to obtain expression plasmids pcDNA3.1-6F7H1, pcDNA3.1-6F7L1, pcDNA3.1-6F7H2, pcDNA3.1-6F7L2, pcDNA3.1-6F7H3 and pcDNA3.1-6F7L3, and the heavy and light chain genes of the recombinant expression plasmids were further sequenced. Then the designed gene combinations comprising corresponding light and heavy chain recombinant plasmids (pcDNA3.1-6F7H1/pcDNA3.1-6F7L1, pcDNA3.1-6F7H2/pcDNA3.1-6F7L2, and pcDNA3.1-6F7H3/pcDNA3.1-6F7L3) were separately co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column (MabSelect SURE (GE)) to obtain humanized antibodies.

3. Design of Non-Variable Region Amino Acid Mutations on the Basis of Humanized Antibodies 6F7 H1L1(G1), 6F7 H2L2(G1) and 6F7 H3L3(G1)

On the basis of 6F7 H1L1(G1), 6F7 H2L2(G1) and 6F7 H3L3(G1), new humanized antibodies were obtained by introducing a leucine-to-alanine point mutation at position 234 (L234A) and a leucine-to-alanine point mutation at position 235 (L235A) in the constant region of the heavy chain, and were designated 6F7 H1L1(G1M), 6F7 H2L2 (G1M) and 6F7 H3L3(G1M), respectively.

Example 5: Assay for Binding Activity of Antibodies to Antigens by ELISA

1. Assay for Binding Activity of Antibody 6F7 H1L1(hG4) to Antigen Human CD47 IgV TEV-His by ELISA Experimental procedures: A microplate was coated with 2 μg/mL human CD47 IgV TEV-His and incubated at 4° C. for 12 h. The antigen-coated microplate was rinsed 3 times with PBS, and then blocked with 1% BSA in PBS for 2 h. The microplate was rinsed 3 times with PBS. The antibody serially diluted with PBST solution was added into the wells of the microplate, the dilution gradients for the antibody detailed in Table 2. The microplate containing the test antibody was incubated at 37° C. for 30 min, and then washed 3 times with PBST. HRP-labeled goat anti-human IgG (H+L) (purchased from Jackson ImmunoResearch Inc., Cat. No.: 109-035-088) secondary antibody working solution diluted in a ratio of 1:5000 was added, and the microplate was incubated at 37° C. for 30 min. The microplate was washed 3 times with PBST. TMB (Neogen, 308177) was added for color developing for 5 min in the dark, and then the color development was terminated by adding stop solution. Then the microplate was put into a microplate reader immediately, and the OD value of each well in the microplate was read at 450 nm. The data were analyzed by SoftMax Pro 6.2.1.

The results of detecting the binding of antibody 6F7 H1L1(hG4) to the antigen human CD47 IgV TEV-His are shown in FIG. 1. The OD values for all the dosages are shown in Table 1. The binding $EC_{50}$ of the antibody was calculated by curve fitting using antibody concentration as the abscissa and absorbance value as the ordinate, and the results are shown in Table 1 below.

The results show that the binding EC50 of 6F7 H1L1 (hG4) to human CD47 IgV TEV-His is 0.078 nM, which is comparable to that of Hu5F9-G4.

TABLE 1

The results of the assay for the binding activity of 6F7 H1L1(hG4) to human CD47 IgV TEV-His

| Antibody dilution | Antigen coating: human CD47 IgV TEV-His (2 μg/mL) | | | |
|---|---|---|---|---|
| (μg/mL) | 6F7 H1L1(hG4) | | Hu5F9-G4 | |
| 0.333 | 2.639 | 2.723 | 2.929 | 3.056 |
| 1:3 | 2.566 | 2.608 | 2.623 | 2.955 |
| 1:9 | 2.159 | 2.217 | 2.394 | 2.513 |
| 1:27 | 1.425 | 1.522 | 1.652 | 1.838 |
| 1:81 | 0.749 | 0.765 | 0.866 | 0.938 |
| 1:243 | 0.329 | 0.333 | 0.396 | 0.431 |
| 1:729 | 0.133 | 0.143 | 0.160 | 0.173 |
| 0 | 0.052 | 0.050 | 0.049 | 0.047 |
| Second antibody | Goat anti-human IgG Fc, HRP | | | |
| EC50 (nM) | 0.078 | | 0.068 | |

2. Assay for Binding Activity of Antibody 6F7 H1L1(G1M) to Antigen Human CD47 IgV TEV-His by ELISA Experimental procedures: A microplate was coated with 2 μg/mL human CD47 IgV TEV-His and incubated at 4° C. for 12 h. The antigen-coated microplate was rinsed 3 times with PBS, and then blocked with 1% BSA in PBS for 2 h. The microplate was rinsed 3 times with PBS. The antibody serially diluted with PBST solution was added into the wells of the microplate, the dilution gradients for the antibody detailed in Table 2. The microplate containing the test antibody was incubated at 37° C. for 30 min, and then washed 3 times with PBST. HRP-labeled goat anti-human IgG (H+L) (purchased from Jackson ImmunoResearch Inc., Cat. No.: 109-035-088) secondary antibody working solution diluted in a ratio of 1:5000 was added, and the microplate was incubated at 37° C. for 30 min. The microplate was washed 3 times with PBST. TMB (Neogen, 308177) was added for color developing for 5 min in the dark, and then the color development was terminated by adding stop solution. Then the microplate was put into a microplate reader immediately, and the OD value of each well in the microplate was read at 450 nm. The data were analyzed by SoftMax Pro 6.2.1.

Figure 2:
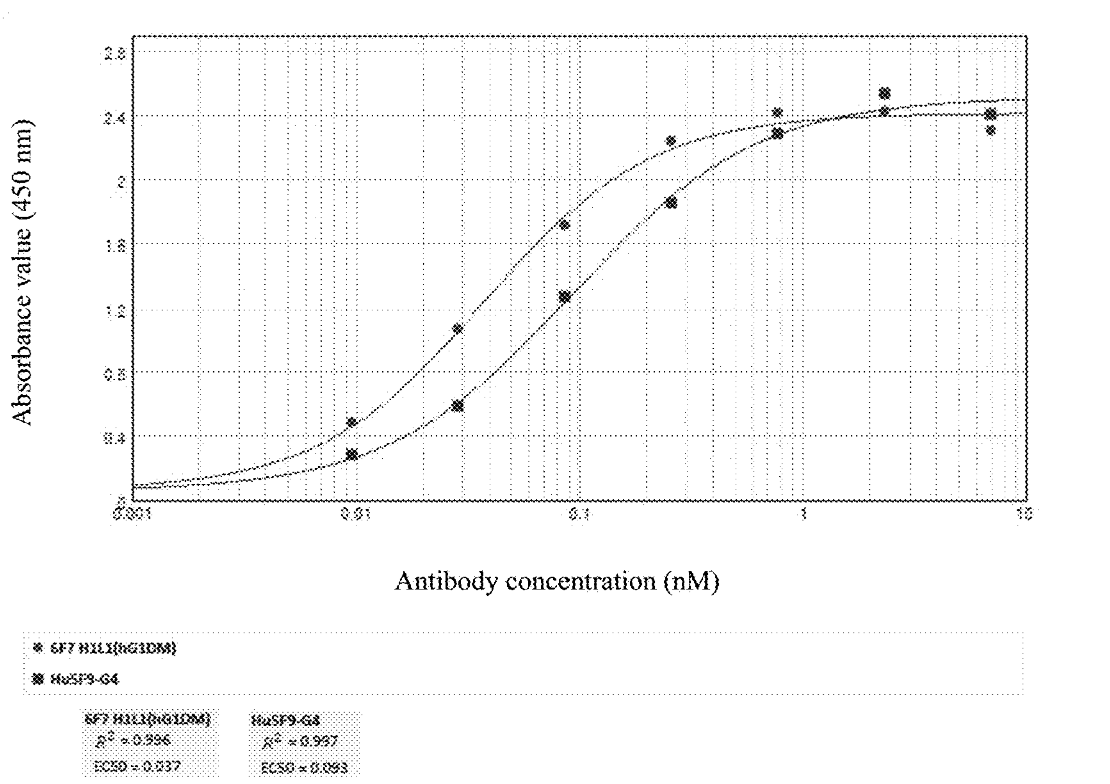
FIG. 2 shows the results of an assay for the binding activity of 6F7 H1L1(G1M) to human CD47 IgV TEV-His, where 6F7 H1L1(hG1DM) is 6F7 H1L1(G1M).

The results of detecting the binding of antibody 6F7 H1L1(G1M) to the antigen human CD47 IgV TEV-His are shown in FIG. 2. The OD values for all the dosages are shown in Table 2. The binding $EC_{50}$ of the antibody was calculated by curve fitting using antibody concentration as the abscissa and absorbance value as the ordinate, and the results are shown in Table 2 below.

TABLE 2

The results of the assay for the binding activity of 6F7 H1L1(G1M) to human CD47 IgV TEV-His

| Antibody dilution (μg/mL) | Antigen coating: human CD47 IgV TEV-His (2 μg/mL) | | | |
|---|---|---|---|---|
| | 6F7 H1L1(G1M) | | Hu5F9-G4 | |
| 1.000 | 2.298 | 2.307 | 2.390 | 2.428 |
| 0.333 | 2.410 | 2.438 | 2.505 | 2.566 |
| 0.111 | 2.482 | 2.352 | 2.275 | 2.305 |
| 0.037 | 2.301 | 2.182 | 1.847 | 1.854 |
| 0.012 | 1.697 | 1.737 | 1.270 | 1.264 |
| 0.004 | 1.141 | 0.987 | 0.599 | 0.580 |
| 0.001 | 0.476 | 0.492 | 0.282 | 0.275 |
| 0 | 0.047 | 0.046 | 0.047 | 0.046 |
| Second antibody | Goat anti-human IgG (H + L), HRP | | | |
| EC50 (nM) | 0.037 | | 0.093 | |

The results show that the binding EC50 of 6F7 H1L1 (G1M) to human CD47 IgV TEV-His is 0.037 nM, which is slightly higher than that of Hu5F9-G4.

3. Assay for Competitive Binding Activity of Antibody 6F7 H1L1(hG4) Against Human SIRPα ECD-hFc-Biotin for Human CD47 IgV TEV-His by Competitive ELISA Experimental procedures: A microplate was coated with 2 μg/mL human CD47 IgV TEV-His at 50 μL per well and incubated at 4° C. for 16 h. The microplate was washed once and tapped dry, blocked with 1% BSA (in PBS) at 300 μL per well, incubated at 37° C. for 2 h, and washed three times and tapped dry. The antibody was diluted to 3 μg/mL (final concentration: 1.5 μg/mL) as the initial concentration, and a 1:3 serial dilution was performed to give a total of 7 concentrations, in addition to a blank control. Two duplicate wells were set for the above concentrations, with a final volume of 50 μL per well, and the plate was incubated for 10 min. 0.2 μg/mL (final concentration: 0.1 μg/mL) human SIRPα ECD-hFc-Biotin (synthesized by Zhongshan Akeso Biopharma Ltd.) was added to the microplate at 50 μL per well and gently mixed with the antibody at a volume ratio of 1:1, and the microplate was incubated at 37° C. for 30 min. The microplate was washed three times and tapped dry. 50 μL of SA-HRP (KPL, 14-30-00) working solution was added to each well, and the microplate was incubated at 37° C. for 30 min. The microplate was washed four times and tapped dry. 50 μL of TMB chromogenic solution was added to each well for color developing for 5 min at room temperature in the dark, and then the color development was terminated by adding 50 μL of stop solution to each well. Then the microplate was put into a microplate reader immediately, and the OD value of each well in the microplate was read at 450 nm. The data were analyzed and processed by SoftMax Pro 6.2.1.

Figure 3:
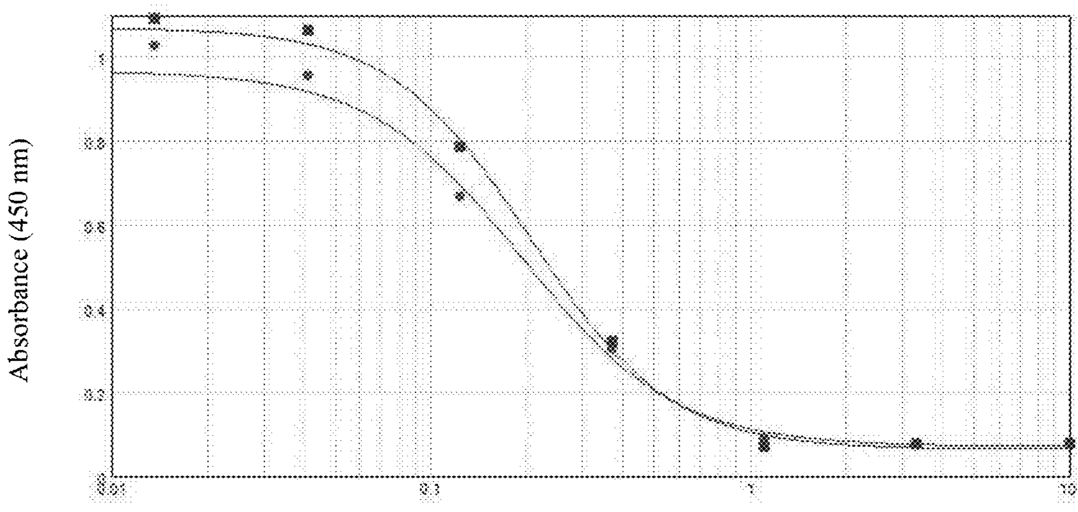
FIG. 3 shows the results of an assay for the competitive binding activity of 6F7 H1L1(hG4) against human SIRPα ECD-hFc-Biotin for human CD47 IgV TEV-His.
Figure 3:

The results are shown in FIG. 3. The OD values for all the dosages are shown in Table 3. By quantitative analysis of the absorbance intensity of the bound antibody, the curve simulation was performed to give the binding efficiency EC50 of the antibody (Table 3).

The results show that 6F7 H1L1(hG4) can effectively block the binding of the antigen human CD47 IgV TEV-His to its receptor human SIRPα ECD-hFc-Biotin, the blocking efficiency presenting a dose-dependent relationship; the blocking EC50 of 6F7 H1L1(hG4) is 0.194 nM, which is the same as that of Hu5F9-G4.

TABLE 3

The results of the assay for the competitive binding activity of 6F7 H1L1(hG4) against human SIRPα ECD-hFc-Biotin for human CD47 IgV TEV-His

| Antibody dilution (μg/mL) | Antigen coating: human CD47 IgV TEV-His (2 μg/mL) | | | |
|---|---|---|---|---|
| | 6F7 H1L1(hG4) | | Hu5F9-G4 | |
| 1.5 | 0.077 | 0.080 | 0.072 | 0.081 |
| 1:3 | 0.073 | 0.071 | 0.069 | 0.082 |
| 1:9 | 0.092 | 0.088 | 0.062 | 0.074 |
| 1:27 | 0.320 | 0.289 | 0.290 | 0.349 |
| 1:81 | 0.654 | 0.679 | 0.793 | 0.776 |
| 1:243 | 0.970 | 0.944 | 1.102 | 1.030 |
| 1:729 | 1.035 | 1.016 | 1.142 | 1.038 |
| 0 | 0.859 | 0.904 | 1.124 | 0.928 |
| | Human SIRPα ECD-hFc-Biotin, 0.1 μg/mL | | | |
| Second antibody | SA-HRP | | | |
| EC50 (nM) | 0.194 | | 0.205 | |

4. Assay for Competitive Binding Activity of Antibody 6F7 H1L1(G1M) Against Human SIRPα ECD-hFc-Biotin for Human CD47 IgV TEV-His by Competitive ELISA Experimental procedures: A microplate was coated with 2 μg/mL human CD47 IgV TEV-His at 50 μL per well and incubated at 4° C. for 16 h. The microplate was washed once and tapped dry, blocked with 1% BSA (in PBS) at 300 μL per well, incubated at 37° C. for 2 h, and washed three times and tapped dry. The antibody was diluted to 3 μg/mL (final concentration: 0.5 μg/mL) as the initial concentration, and a 1:3 serial dilution was performed to give a total of 7 concentrations, in addition to a blank control. Two duplicate wells were set for the above concentrations, with a final volume of 50 μL per well, and the plate was incubated for 10 min. 0.2 μg/mL (final concentration: 0.1 μg/mL) human SIRPα ECD-hFc-Biotin was added to the microplate at 50 μL per well and gently mixed with the antibody at a volume ratio of 1:1, and the microplate was incubated at 37° C. for 30 min. The microplate was washed three times and tapped dry. 50 μL of SA-HRP (KPL, 14-30-00) working solution was added to each well, and the microplate was incubated at 37° C. for 30 min. The microplate was washed four times and tapped dry. 50 μL of TMB chromogenic solution was added to each well for color developing for 5 min at room temperature in the dark, and then the color development was terminated by adding 50 μL of stop solution to each well. Then the microplate was put into a microplate reader immediately, and the OD value of each well in the microplate was read at 450 nm. The data were analyzed and processed by SoftMax Pro 6.2.1.

Figure 4:
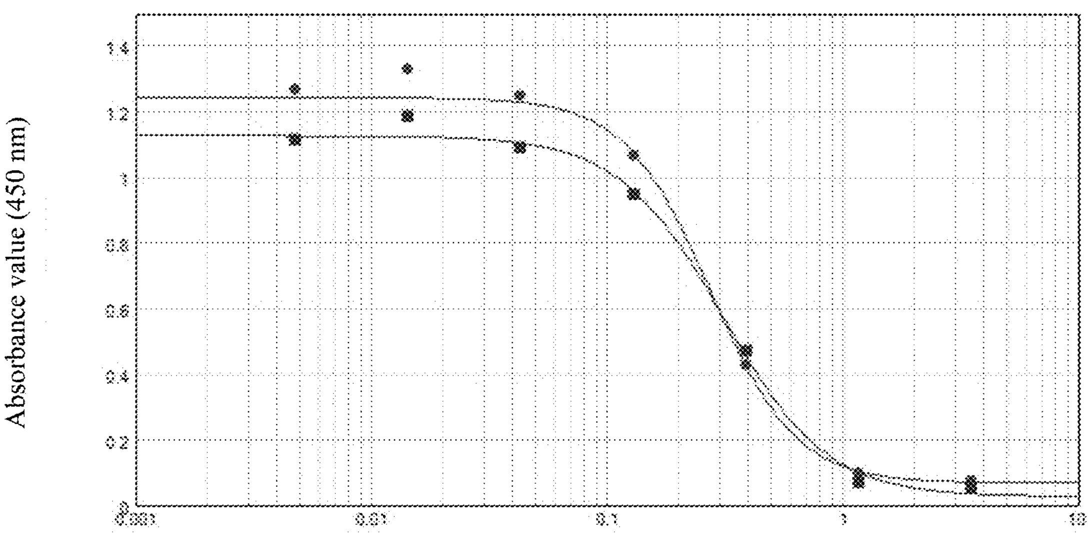
FIG. 4 shows the results of an assay for the competitive binding activity of 6F7 H1L1(G1M) against human SIRPα ECD-hFc-Biotin for human CD47 IgV TEV-His, where 6F7 H1L1(hG1DM) is 6F7 H1L1(G1M).
Figure 4:

The results are shown in FIG. 4. The OD values for all the dosages are shown in Table 4. By quantitative analysis of the absorbance intensity of the bound antibody, the curve simulation was performed to give the binding efficiency EC50 of the antibody (Table 4).

TABLE 4

The results of the assay for the competitive binding activity of 6F7 H1L1(G1M) against human SIRPα ECD-hFc-Biotin for human CD47 IgV TEV-His

| Antibody dilution | Antigen coating: human CD47 IgV TEV-His (2 μg/mL) | | | |
|---|---|---|---|---|
| (μg/mL) | 6F7 H1L1(G1M) | | Hu5F9-G4 | |
| 0.5 | 0.076 | 0.070 | 0.056 | 0.057 |
| 1:3 | 0.104 | 0.096 | 0.075 | 0.066 |
| 1:9 | 0.420 | 0.435 | 0.530 | 0.408 |
| 1:27 | 1.017 | 1.119 | 0.932 | 0.968 |
| 1:81 | 1.196 | 1.304 | 1.075 | 1.104 |
| 1:243 | 1.265 | 1.394 | 1.221 | 1.151 |
| 1:729 | 1.225 | 1.312 | 1.173 | 1.056 |
| 0 | 1.045 | 1.191 | 1.070 | 1.132 |
| | Human SIRPα ECD-hFc-Biotin, 0.1 μg/mL | | | |
| Second antibody | SA-HRP (1:4000) | | | |
| EC50 (nM) | 0.274 | | 0.310 | |

The results show that 6F7 H1L1(G1M) can effectively block the binding of the antigen human CD47 IgV TEV-His to its receptor human SIRPα ECD-hFc-Biotin, the blocking efficiency presenting a dose-dependent relationship; the blocking EC50 of 6F7 H1L1(G1M) is 0.274 nM, which is comparable to that of Hu5F9-G4.

Example 6: Determination of Affinity Constant of Murine Antibody 6F7 for Human CD47

Kinetic parameters of the binding of murine antibody 6F7 to the antigen human CD47 IgV TEV-His were determined using a Fortebio system (Forteio, model: QKe).

An AR2G sensor (Forteio, Cat. No: 18-5092) was activated using EDC/NHS, and the antibody was immobilized by amine coupling to the activated AR2G sensor. The sensor was equilibrated in PBST for 300 s. The antigen immobilized on the sensor was allowed to bind to the antibody for 420 s, with the antigen at a concentration of 3.125-100 nM (serial two-fold dilution). The antigen and the antibody were subjected to dissociation in PBST for 600 s.

Figure 5:
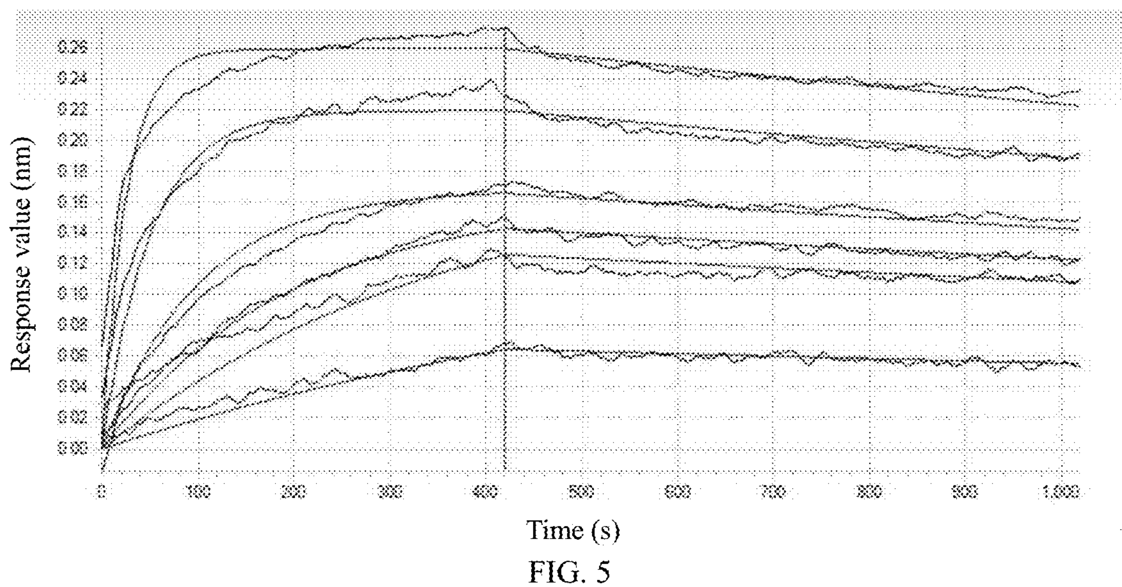
FIG. 5 shows the results of determining the affinity constant of murine antibody 6F7 for human CD47.

The results of determining the affinity constants of the murine antibody 6F7 and Hu5F9-G4 (as a control antibody) for human CD47 IgV TEV-His are shown in Table 5 and FIG. 5.

TABLE 5

The results of determining the affinity constant of murine antibody 6F7 for human CD47

| Antibody | KD (M) | kon(1/Ms) | kon Error | kdis(1/s) | kdis Error | Rmax Range(nm) |
|---|---|---|---|---|---|---|
| 6F7 | 6.52E−10 | 3.93E+05 | 7.41E+03 | 2.56E−04 | 9.48E−06 | 0.1684-0.2614 |
| Hu5F9-G4 | 6.38E−10 | 5.26E+05 | 9.79E+03 | 3.36E−04 | 9.38E−06 | 0.1400-0.3609 |

KD refers to affinity constant; KD = kdis/kon.

The results show that: as shown in Table 5 and FIG. 5, the affinity constants of murine antibody 6F7 and Hu5F9-G4 for human CD47 IgV TEV-His were comparably 6.52E-10 M and 6.38E-10 M, respectively. It suggests that the CDR regions of 6F7 have comparable great ability to bind to CD47 to those of Hu5F9-G4.

Example 7: Determination of Affinity Constant of Antibody 6F7 H1L1(hG4) for Human CD47

Figure 6:
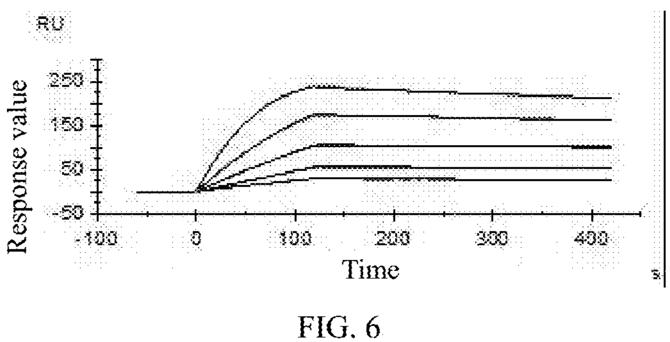
FIG. 6 shows the results of determining the affinity constant of 6F7 H1L1(hG4) for human CD47.
Figure 7:
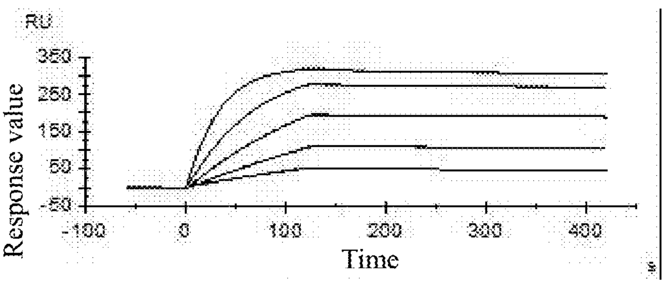
FIG. 7 shows the results of determining the affinity constant of Hu5F9-G4 for human CD47.

The affinity constant of antibody 6F7 H1L1(hG4) for human CD47 IgV TEV-His was determined using a Biacore system (Forteio, model: QKe) according to the manual. The buffer solution was PBST. Human CD47 IgV-TEV-His was immobilized on the surface of a CMS chip by amine coupling, with an immobilization signal value of 171.6 RU. The antibody was allowed to bind to human CD47 for 120 s at a flow rate of 30 μL/min, with the antibody at a concentration of 0.78-12.5 nM (two-fold dilution). The antibody and human CD47 were subjected to dissociation for 300 s. The chip was regenerated with 3 M $MgCl_2$ for 30 s at a flow rate of 30 μL/min. The data were analyzed by 1:1 model fitting to obtain affinity constants. Data were acquired using Biacore Control 2.0 software and analyzed using Biacore T200 Evaluation 2.0 software. The results of determining the affinity constants of 6F7 H1L1(hG4) and Hu5F9-G4 (as a control antibody) for human CD47 IgV TEV-His are shown in Table 6, and FIGS. 6 and 7. The results show that: as shown in the figures, the affinity constants of 6F7 H1L1(hG4) and Hu5F9-G4 for human CD47 IgV TEV-His are 1.52E-10 M and 4.42E-11 M, respectively, suggesting greater ability of 6F7 H1L1(hG4) to bind to human CD47.

TABLE 6

The results of determining the affinity constant of 6F7 H1L1(hG4) for human CD47 IgV TEV-His

| Name of antibody | KD (M) | ka(1/Ms) | SE(ka) | kd(1/s) | SE(kd) | Rmax (RU) |
|---|---|---|---|---|---|---|
| 6F7H1L1 (hG4) | 1.52E−10 | 2.54E+06 | 1.48E+04 | 3.88E−04 | 1.14E−06 | 253.21-272.60 |
| Hu5F9-G4 | 4.42E−11 | 3.00E+06 | 8.49E+03 | 1.32E−04 | 5.69E−07 | 238.81-327.23 |

KD refers to affinity constant; KD = kdis/kon.

Example 8: Study on Cell Bioactivity of 6F7 H1L1(G1M)

1. Detection of Binding of 6F7 H1L1(G1M) to Normal Human RBCs by FACS

Normal human red blood cells were isolated in a biosafety cabinet: blood buffers A and B were well mixed in a ratio of 1:9 to obtain a blood buffer; 20 mL of fresh blood was well mixed with 60 mL of the blood buffer; 15 mL of Ficoll Paque reagent was added to 50 mL centrifuge tubes, and then the diluted fresh blood was slowly added to the surface of the reagent in a ratio of 3:4, i.e., 20 mL of the diluted blood was added to each tube; centrifugation was performed at 1550 rpm for 30 min; RBCs at the bottom of the centrifuge tubes were slowly pipetted and washed 3 times with PBS and centrifuged; the cell pellets were resuspended in 500 μL of 1% PBSA and counted; the concentration of RBCs was adjusted, and the cells were transferred to 1.5 mL centrifuge tubes at 0.3 million cells per tube; centrifugation was performed at 5600 rpm for 5 min, and the supernatant was discarded; 100 μL of the antibody with a corresponding concentration (final concentrations: 100, 10, 1, 0.1, 0.01, 0.001 nM) was added according to the experimental design to each tube, and a Blank group (PBSA+cells) and an isotype control (hIgG) group were designed, followed by incubation on ice for 1 h; 500 μL of 1% PBSA was added, followed by centrifugation at 5600 rpm for 5 min, and the supernatant was discarded; 100 μL of FITC goat anti-human IgG (1:500) was added to each tube, and the resulting mixtures were well mixed and incubated on ice for 30 min in the dark; 500 μL of 1% PBSA was added, followed by centrifugation at 5600 rpm for 5 min, and the supernatant was discarded; 200 μL of 1% washing buffer was added to each tube to resuspend the cells, and fluorescence signals were detected with FITC channel on a flow cytometer.

The results were analyzed using Flowing software, and curve fittings were performed separately using MFI and sample concentration on GraphPad prism 5 to calculate EC50.

Figure 8:
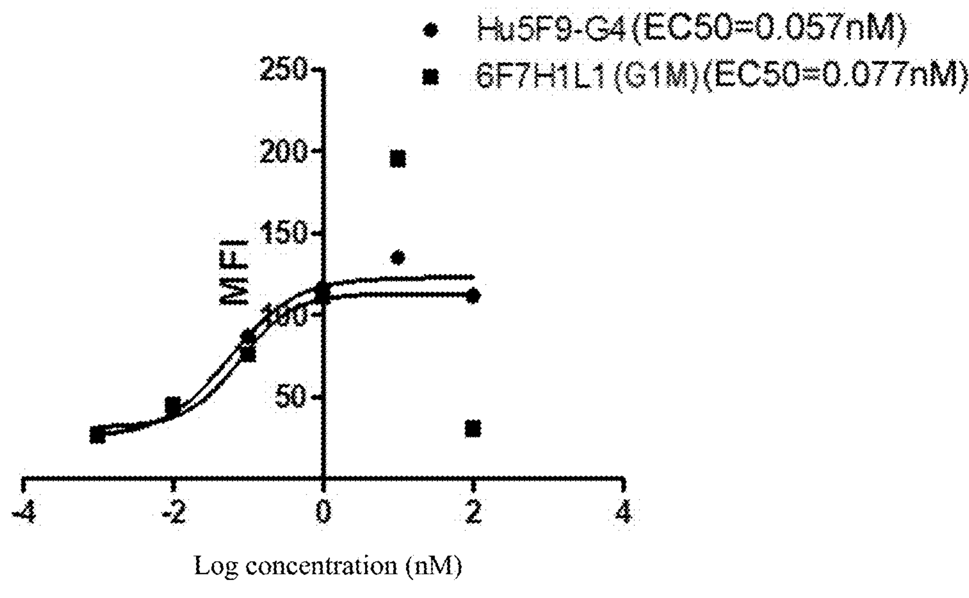
FIG. 8 shows a binding curve of 6F7 H1L1(G1M) to human RBCs (FACS).

The results of the binding of 6F7 H1L1(G1M) to CD47 on the cell membrane surface of normal human RBCs are shown in FIG. 8. The results show that both 6F7 H1L1 (G1M) and the marketed medicament Hu5F9-G4 for the same target can specifically bind to CD47 on the cell membrane surface of normal human RBCs, with the comparable binding EC50 being 0.077 nM and 0.057 nM, respectively.

2. Assay for Binding Activity of 6F7 H1L1(G1M) to Raji by FACS

Raji cells in the log phase were collected, centrifuged, and washed. The cell pellets were resuspended in 1% PBSA and counted, and the viability was determined. The cells were transferred to 1.5 mL tubes according to $3.0\times10^5$ cells/500 μL/tube, and centrifuged at 5600 rpm for 5 min, and the supernatant was discarded. 100 μL of the corresponding antibody serially diluted was added to each tube according to the experimental design, and a blank group (PBSA+cells) and an isotype control (hIgG) group were designed, followed by incubation on ice for 1 h. Then 1% PBSA was added, followed by centrifugation at 5600 rpm for 5 min, and the supernatant was discarded. 100 μL of FITC goat anti-human IgG (1:500) was added to each tube, and the mixtures were well mixed and incubated on ice for 30 min in the dark. 500 μL of 1% PBSA was added, followed by centrifugation at 5600 rpm for 5 min, and the supernatant was discarded. 1% PBSA was added to each tube to resuspend the cells, and fluorescence signals were detected with FITC channel on a flow cytometer. Curve fittings were performed separately using MFI and sample concentration to calculate EC50.

Figure 9:
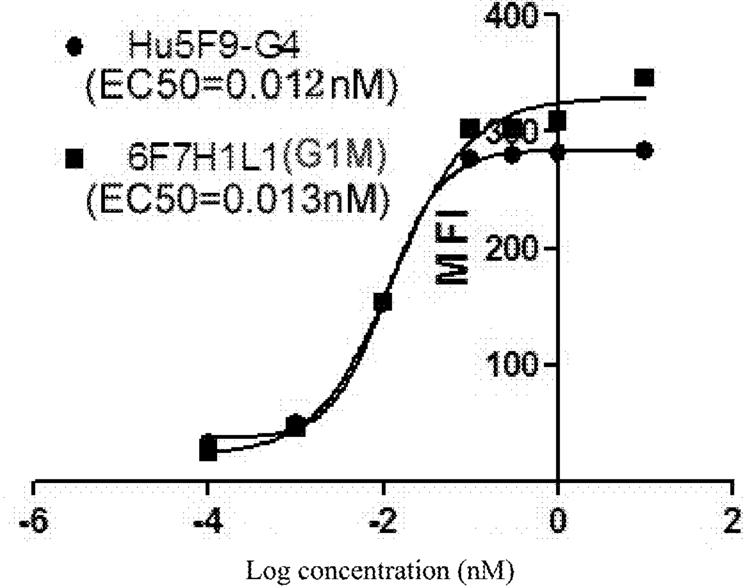
FIG. 9 shows the binding activity of 6F7 H1L1(G1M) to tumor cells Raji (FACS).

The results of the binding activity of 6F7 H1L1(G1M) to Raji are shown in FIG. 9. As shown in the figure, the results show that both 6F7 H1L1(G1M) and Hu5F9-G4 can specifically bind to CD47 on the cell membrane surface of Raji cells, with the comparable binding EC50 being 0.013 nM and 0.012 nM, respectively.

3. Assay for Competitive Binding Bioactivity of 6F7 H1L1 (G1M) Against SIRP for LOVO by FACS LOVO cells in the log phase (Chinese Academy of Sciences Cell Bank, Accession No. bio-73085) were routinely collected, centrifuged and washed. The cell pellets were resuspended in 1% PBSA and counted, and the viability was determined. The cell concentration was adjusted with 1% PBSA into a suitable range, and the cells were transferred in groups into 1.5 mL tubes at 500 μL per tube, for a total of 0.3 million cells. The cells were centrifuged at 5600 rpm for 5 min, and the supernatant was discarded. The antibody serially diluted was added (final concentrations in descending order: 300, 100, 10, 1, 0.3, 0.1, 0.01, 0.001, 0.0001 nM), and a blank control (100 μL of 1% PBSA+cells) and an isotype control (human hIgG) were set up, followed by incubation on ice for 30 min. 100 μL SIRPα-mFc was added into each tube, and the mixtures were well mixed at a final concentration of 20 nM, and incubated on ice for 1 h. 1% PBSA was added, followed by centrifugation at 5600 rpm for 5 min, and the supernatant was discarded. 100 μL of FITC goat anti-mouse IgG (1:500 dilution) was added to each tube, followed by incubation on ice for 40 min in the dark. 1% PBSA was added, followed by centrifugation at 5600 rpm for 5 min, and the supernatant was discarded. 200 μL of 1% PBSA was added to resuspend the cell pellets, and the suspensions were transferred to flow cytometry tubes. Fluorescence signals were detected with FITC channel on a flow cytometer. Curve fittings were performed separately using MFI and sample concentration to calculate EC50.

Figure 10:
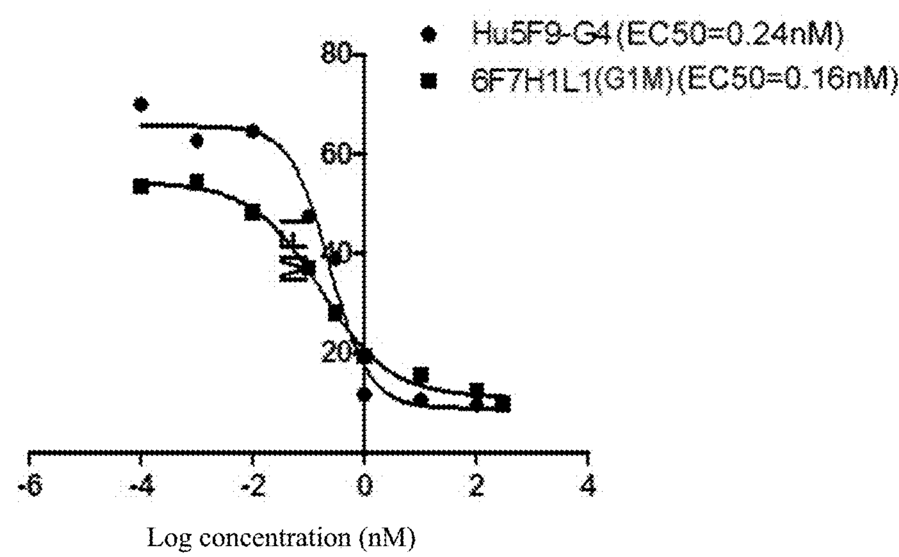
FIG. 10 shows an assay for the competitive binding activity of 6F7 H1L1(G1M) against SIRP for LOVO (FACS).

The competitive binding activity of 6F7 H1L1(G1M) against SIRP for LOVO was assayed. The results are shown in FIG. 10. As shown in the figure, both 6F7 H1L1(G1M) and Hu5F9-G4 can compete with SIRP for binding to CD47 on the membrane surface of LOVO, thereby blocking the binding of SIRP to CD47, with their comparable competitive binding EC50 being 0.16 nM and 0.24 nM, respectively.

4. Effect of 6F7 H1L1(G1M) on Agglutination of Normal Human RBCs

Preparation of normal human RBCs: human blood PBMCs were isolated according to the manual of Ficoll-Paque Plus reagent, and the red blood cells precipitated to the bottom were used for this experiment. The red blood cells were diluted with PBS to a concentration of $1\times10^7$/mL to obtain a red blood cell suspension, which was then added into a round-bottom 96-well plate. The positive antibody with a corresponding concentration was added, 0.1 g/mL Dextran T500 was added into a control, and corresponding hIgG or PBS was added into a negative control, followed by culture at 37° C. for 4 h. The agglutination of the red blood cells was examined and photographed.

Figure 11:
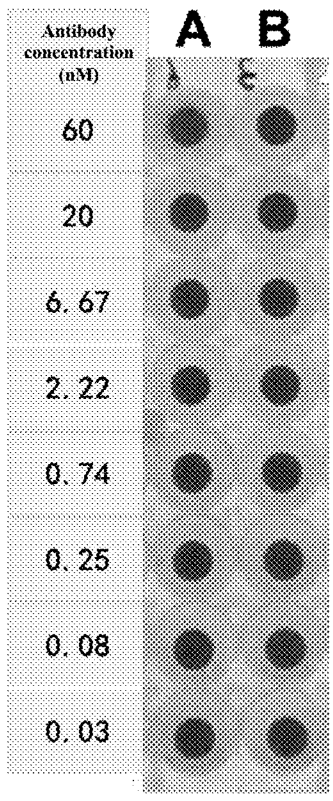
FIG. 11 shows the agglutination of human red blood cells by 6F7 H1L1(G1M) antibody.
Figure 11:
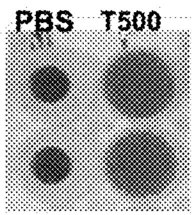

The effect of 6F7 H1L1(G1M) on the agglutination of normal human red blood cells is shown in FIG. 11. As shown in the figure, 6F7 H1L1(G1M) and the control antibody Hu5F9-G4 have no effect on the agglutination of red blood cells when the antibody concentration is lower than 20 μg/mL; however, when the antibody concentration is higher than 20 μg/mL, noticeable facilitated agglutination of red blood cells by Hu5F9-G4 can be observed, while 6F7 H1L1(G1M) still has no effect on the agglutination of red blood cells.

Example 9: Study on Cell Bioactivity of 6F7 H1L1(hG4)

1. Detection of Binding of 6F7 H1L1(hG4) to Normal Human RBCs by FACS

Experimental procedures: Blood buffers A (D-(+)-glucose: 1 g; $CaCl_2$: 0.0056 g; $MgCl_2 \cdot 6H_2O$: 0.1992 g; KCl: 0.4026 g; Tris: 17.5650 g; dissolved in 1 L of ultrapure water) and B (NaCl: 8.19 g, dissolved in 1 L of ultrapure water) were mixed in a ratio of 1:9 to obtain a blood buffer. Fresh blood was mixed well with blood buffer (blood dilution ratio of 1:3 after concentration). 15 mL of Ficoll Paque plus reagent (GE, Cat. No. 17-1440-02) was added to 50 mL centrifuge tubes, and diluted fresh blood was slowly added to the surface of the reagent in a volume ratio of 3:4, i.e., 20 mL of diluted blood was added to each tube. The tubes were each centrifuged at 1550 rpm for 30 min after balancing. The PBMCs in the middle buffy coat layer were pipetted. The blood buffer was added in a volume ratio of cells to blood buffer of 1:4. The resulting mixture was well mixed and centrifuged at 950 rpm for 15 min, and the supernatant was discarded. 20 mL of the blood buffer was added to resuspend PBMCs. The resulting suspension was centrifuged, and the supernatant was discarded. Centrifugation was performed, followed by two washings. The cells were washed once with 10 mL of RPMI-1640 (FBS-free). Centrifugation was performed and the supernatant was discarded. The cells were resuspended in 5 mL of RPMI-1640 (containing 10% FBS), and counted, with $3\times10^5$ cells per sample. 500 μL of 1% PBSA was added to each tube, followed by centrifugation at 5600 rpm for 5 min. The supernatant was discarded. 100 μL of the antibody with a corresponding concentration was added (final concentrations: 300, 100, 10, 1, 0.1, 0.01, 0.001 nM) to each tube, and a Blank (PBSA+cells) and an isotype control were designed, followed by incubation on ice for 1 h. 1% PBSA was added, followed by centrifugation at 5600 rpm for 5 min, and the supernatant was discarded. 100 μL of FITC goat anti-human IgG (Jacson, Cat. No. 109-095-098, 1:500 dilution) or FITC goat anti-mouse IgG (BD bioscience, Cat. No. 555988) (1:500) was added, and the resulting mixtures were well mixed and incubated on ice for 30 min in the dark. 1% PBSA was added, followed by centrifugation at 5600 rpm for 5 min, and the supernatant was discarded. 200 μL of 1% washing buffer was added to each tube to resuspend the cells, and fluorescence signals were detected with FITC channel on a flow cytometer. The results were analyzed using Flowing software, and curve fittings were performed separately using MFI and sample concentration on GraphPad prism 5 to calculate EC50.

Figure 12:
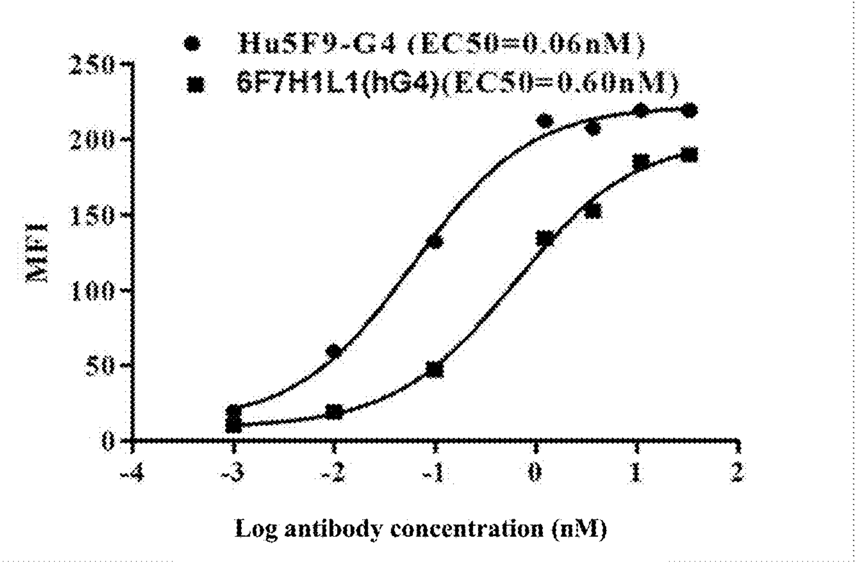
FIG. 12 shows a binding curve of 6F7 H1L1(hG4) to human RBCs (FACS).

The results of the binding of 6F7 H1L1(hG4) to CD47 on the cell membrane surface of normal human RBCs are shown in FIG. 12 and Table 7. The results show that both 6F7 H1L1(hG4) and the marketed drug Hu5F9-G4 for the same target can specifically bind to CD47 on the cell membrane surface of normal human RBCs, with the binding EC50 being 0.60 nM and 0.06 nM, respectively, and the affinity of Hu5F9-G4 for RBCs is 10 times higher than that of 6F7 H1L1(hG4).

TABLE 7

The results of detecting the binding of anti-CD47 antibody to human RBCs by FACS

| Concentration (nM)/MFI | 0.00123 | 0.0123 | 0.123 | 1.23 | 3.7 | 11.1 | 33.3 | EC50 |
|---|---|---|---|---|---|---|---|---|
| Hu5F9-G4 | 19.48 | 59.35 | 132.68 | 212.25 | 207.52 | 219.34 | 219.02 | 0.06 |
| 6F7 H1L1(hG4) | 10.25 | 19.55 | 47.29 | 134.58 | 152.50 | 185.31 | 190.18 | 0.60 |

2. Assay for Binding Activity of 6F7 H1L1(hG4) to Raji by FACS

The binding bioactivity of the CD47 antibody to tumor cell Raji (Chinese Academy of Sciences, Shanghai Institutes for Biological Sciences Cell Center, Cat. No. TCHu 44) was assayed by flow cytometry.

Raji cells were counted, and the viability was determined, with $3\times10^5$ cells per sample. 500 μL of 1% PBSA was added to each tube, followed by centrifugation at 5600 rpm for 5 min, and the supernatant was discarded. The antibody serially diluted was added according to the experimental design, and a blank (PBSA+cells) group and an isotype control group (human IgG) were designed, followed by incubation on ice for 1 h. 1% PBSA was added, followed by centrifugation at 5600 rpm for 5 min, and the supernatant was discarded. 100 μL of FITC goat anti-human IgG (1:500) or FITC goat anti-mouse IgG (1:500) was added, and the resulting mixtures were well mixed and incubated on ice for 30 min in the dark. 500 μL of 1% PBSA was added, followed by centrifugation at 5600 rpm for 5 min, and the supernatant was discarded. 200 μL of washing buffer was added to each tube to resuspend the cells, and fluorescence signals were detected with FITC channel on a flow cytometer.

Figure 13:
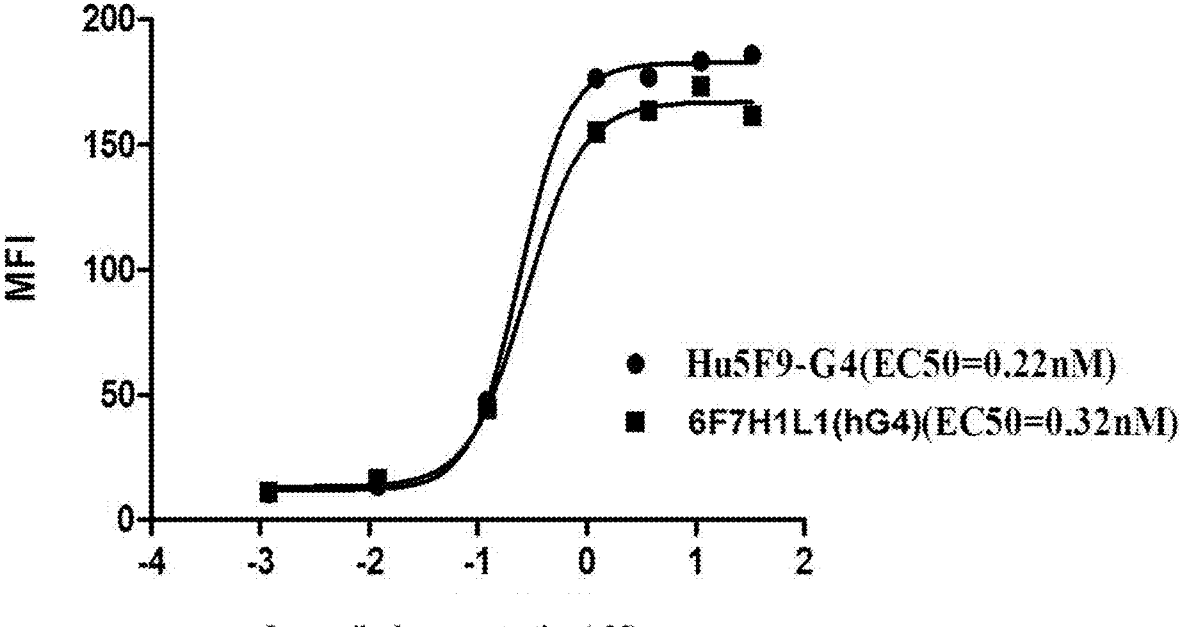
FIG. 13 shows the binding activity of 6F7 H1L1(hG4) to tumor cells Raji (FACS).

The results of the binding activity of 6F7 H1L1(hG4) to Raji are shown in FIG. 13 and Table 8. As shown in the figure and table, the results show that both 6F7 H1L1(hG4) and Hu5F9-G4 can specifically bind to CD47 on the cell membrane surface of Raji cells, with the comparable binding EC50 being 0.32 nM and 0.22 nM, respectively.

TABLE 8

The results of detecting the binding of anti-CD47 antibody to tumor cell Raji by FACS

| Concentration (nM)/MFI | 0.00123 | 0.0123 | 0.123 | 1.23 | 3.7 | 11.1 | 33.3 | EC50 |
|---|---|---|---|---|---|---|---|---|
| Hu5F9-G4 | 10.83 | 13.67 | 47.74 | 176.60 | 177.11 | 183.49 | 185.86 | 0.22 |
| 6F7 H1L1 (hG4) | 11.05 | 16.40 | 44.71 | 155.29 | 163.61 | 173.42 | 161.61 | 0.32 |

3. Assay for Competitive Binding Activity of 6F7 H1L1 (hG4) Against SIRP for Raji by FACS Raji cells in the log phase were routinely collected, centrifuged and washed. The cell pellets were resuspended in 1% PBSA and counted, and the viability was determined. The cell concentration was adjusted with 1% PBSA into a suitable range, and the cells were transferred in groups into 1.5 mL tubes at 500 μL per tube, for a total of 0.3 million cells. The cells were centrifuged at 5600 rpm for 5 min, and the supernatant was discarded. The antibody serially diluted was added (final concentrations in descending order: 1, 0.3, 0.1, 0.01, 0.001, 0.0001 nM), and a blank control (100 μL of 1% PBSA+cells) and an isotype control (human hIgG) were set up, followed by incubation on ice for 30 min. 100 μL SIRPα-ECD-mFc (the sequence of mFc is set forth in SEQ ID NO: 71) was added into each tube, and the mixtures were well mixed at a final concentration of 20 nM, and incubated on ice for 1 h. 1% PBSA was added, followed by centrifugation at 5600 rpm for 5 min, and the supernatant was discarded. 100 μL of FITC goat anti-mouse IgG (1:500 dilution) was added to each tube, followed by incubation on ice for 40 min in the dark. 500 μL of 1% PBSA was added, followed by centrifugation at 5600 rpm for 5 min, and the supernatant was discarded. 200 μL of 1% PBSA was added to resuspend the cell pellets. Fluorescence signals were detected with FITC channel on a flow cytometer.

Figure 14:
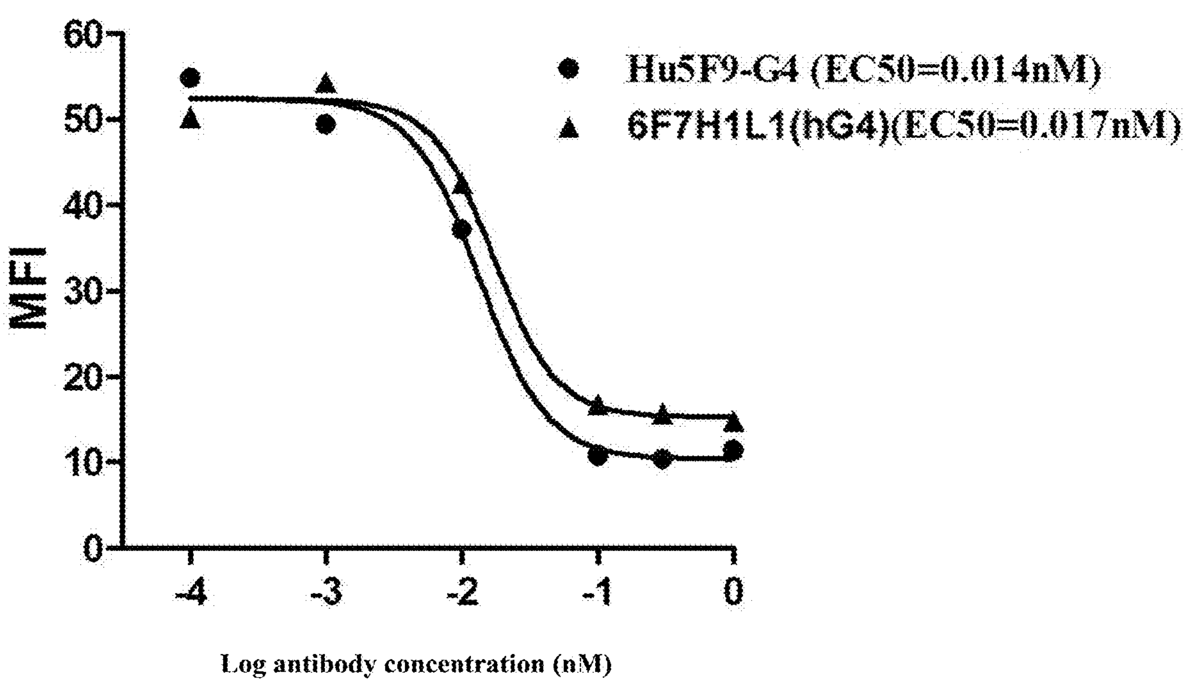
FIG. 14 shows the competitive binding activity of 6F7 H1L1(hG4) against SIRP for tumor cells Raji (FACS).

The results of the competitive binding of 6F7 H1L1(hG4) against SIRP for tumor cell Raji are shown in FIG. 14 and Table 9. As shown in the figure and table, both 6F7 H1L1 (hG4) and Hu5F9-G4 can compete with SIRP for binding to CD47 on the membrane surface of Raji, thereby blocking the binding of SIRP to CD47, with their comparable competitive binding EC50 being 0.017 nM and 0.014 nM, respectively.

TABLE 9

The results of detecting the competitive binding of anti-CD47 antibody against SIRP for Raji cells by FACS

| Concentration (nM)/MFI | 0.0001 | 0.001 | 0.01 | 0.1 | 0.3 | 1 | EC50 |
|---|---|---|---|---|---|---|---|
| Hu5F9-G4 | 54.83 | 49.37 | 37.16 | 10.77 | 10.34 | 11.4 | 0.014 |
| 6F7 H1L1(hG4) | 50.27 | 54.37 | 42.64 | 16.80 | 15.66 | 14.83 | 0.017 |

4. Assay for Binding Activity of 6F7 H1L1(hG4) to LOVO by FACS

LOVO cells in the log phase (Chinese Academy of Sciences Cell Bank, Accession No. bio-73085) were collected, centrifuged, and washed. The cell pellets were resuspended in 500 μL of 1% PBSA and counted, and the viability was determined. The cells were transferred to 1.5 mL tubes according to $3.0\times10^5$ cells/500 μL/tube, and centrifuged at 5600 rpm for 5 min, and the supernatant was discarded. 100 μL of the corresponding antibody serially diluted was added to each tube according to the experimental design, and a blank group (PBSA+cells) and an isotype control group (human hIgG with its heavy chain sequence being SEQ ID NO: 72 and light chain sequence being SEQ ID NO: 73) were designed, followed by incubation on ice for 1 h. Then 500 μL of 1% PBSA was added, followed by centrifugation at 5600 rpm for 5 min, and the supernatant was discarded. 100 μL of FITC goat anti-human IgG (1:500) was added to each tube, and the mixtures were well mixed and incubated on ice for 30 min in the dark. 500 μL of 1% PBSA was added, followed by centrifugation at 5600 rpm for 5 min, and the supernatant was discarded. 200 μL of 1% PBSA was added to each tube to resuspend the cells, and the suspensions were transferred to flow cytometry tubes and detected by a flow cytometer BD FACSCalibur. The results were analyzed using Flowing software, and curve fittings were performed separately using MFI and sample concentration on GraphPad prism 5 to calculate EC50.

Figure 15:
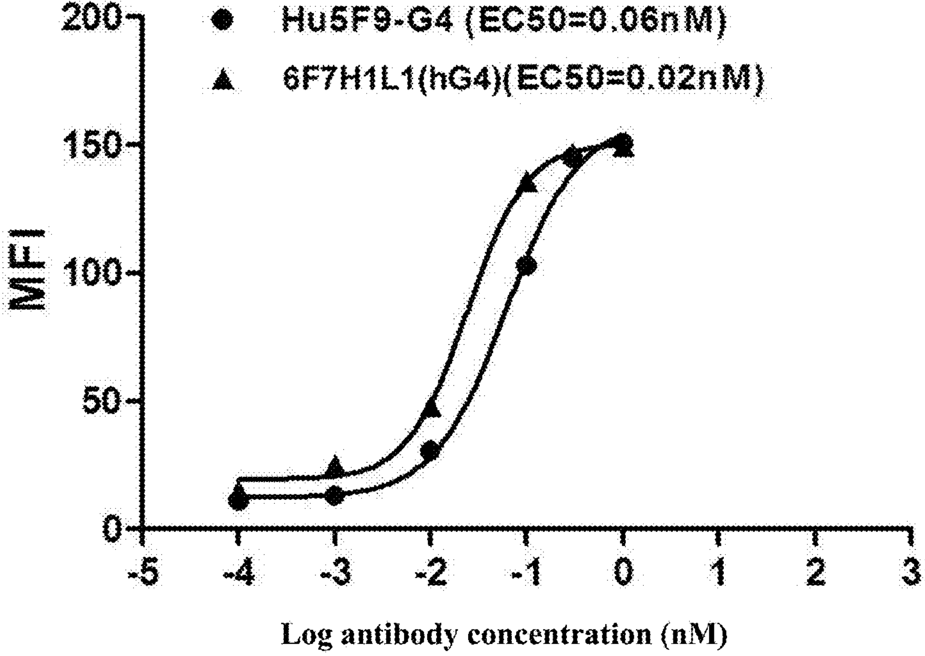
FIG. 15 shows a binding curve of 6F7 H1L1(hG4) to tumor cells LOVO (FACS).

The results of the binding of 6F7 H1L1(hG4) to LOVO are shown in FIG. 15 and Table 10. As shown in the figure and table, both 6F7 H1L1(hG4) and Hu5F9-G4 can specifically bind to CD47 on the cell membrane surface of LOVO cells, with their binding EC50 being 0.02 nM and 0.06 nM, respectively. The binding activity of 6F7 H1L1(hG4) is slightly higher than that of Hu5F9-G4.

TABLE 10

The results of detecting the binding of anti-CD47 antibody to LOVO by FACS

| Concentration (nM)/MFI | 0.0001 | 0.001 | 0.01 | 0.1 | 0.3 | 1 | EC50 |
|---|---|---|---|---|---|---|---|
| Hu5F9-G4 | 11.35 | 13.04 | 30.44 | 102.94 | 145.13 | 150.57 | 0.06 |
| 6F7 H1L1 (hG4) | 15.26 | 25.41 | 48.15 | 135.95 | 146.67 | 149.81 | 0.02 |

5. Assay for Competitive Binding Bioactivity of 6F7 H1L1 (hG4) Against SIRP for LOVO by FACS The experimental procedures are the same as in Example 3 except that Raji cells were changed to LOVO cells.

Figure 16:
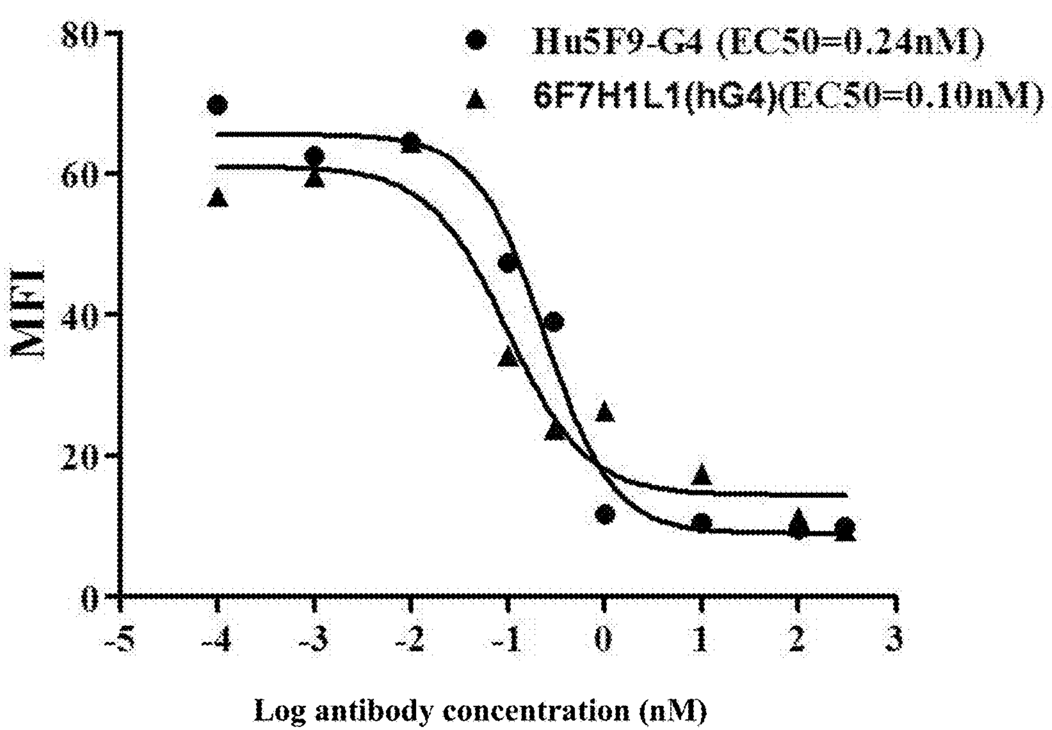
FIG. 16 shows an assay for the competitive binding activity of 6F7 H1L1(hG4) against SIRP for LOVO (FACS).

The results of the assay for the competitive binding activity of 6F7 H1L1(hG4) against SIRP for LOVO are shown in FIG. 16 and Table 11. As shown in the figure and table, both 6F7 H1L1(hG4) and Hu5F9-G4 can compete with SIRP for binding to CD47 on the membrane surface of LOVO, thereby blocking the binding of SIRP to CD47, with their competitive binding EC50 being 0.10 nM and 0.24 nM, respectively. The competitive binding activity of 6F7 H1L1 (hG4) is slightly higher than that of Hu5F9-G4.

TABLE 11

The results of detecting the competitive binding of anti-CD47 antibody against SIRP for LOVO cells by FACS

| Concentration (nM)/MFI | 0.0001 | 0.001 | 0.01 | 0.1 | 0.3 | 1 | 10 | 100 | 300 | EC50 |
|---|---|---|---|---|---|---|---|---|---|---|
| Hu5F9-G4 | 69.81 | 62.47 | 64.45 | 47.30 | 38.98 | 11.63 | 10.51 | 9.59 | 9.93 | 0.24 |
| 6F7 H1L1(hG4) | 56.79 | 59.59 | 64.52 | 34.21 | 23.76 | 26.52 | 17.46 | 11.35 | 9.44 | 0.10 |

6. Effect of Anti-CD47 Antibody on Agglutination of Normal Human RBCs

Preparation of normal human RBCs: human blood PBMCs were isolated according to the manual of Ficoll-Paque Plus reagent (GE, Cat. No. 17-1440-02), and the red blood cells precipitated to the bottom were used for this experiment. The red blood cells were diluted with PBS to a concentration of $1\times10^7$/mL to obtain a red blood cell suspension, which was then added into a round-bottom 96-well plate. The positive antibody with a corresponding concentration was added, 0.1 g/mL Dextran T500 was added into a control, and corresponding human IgG1 (Akeso Biopharma) or PBS was added into a negative control, followed by culture at 37° C. for 4 h. The agglutination of the red blood cells was examined and photographed.

Figure 17:
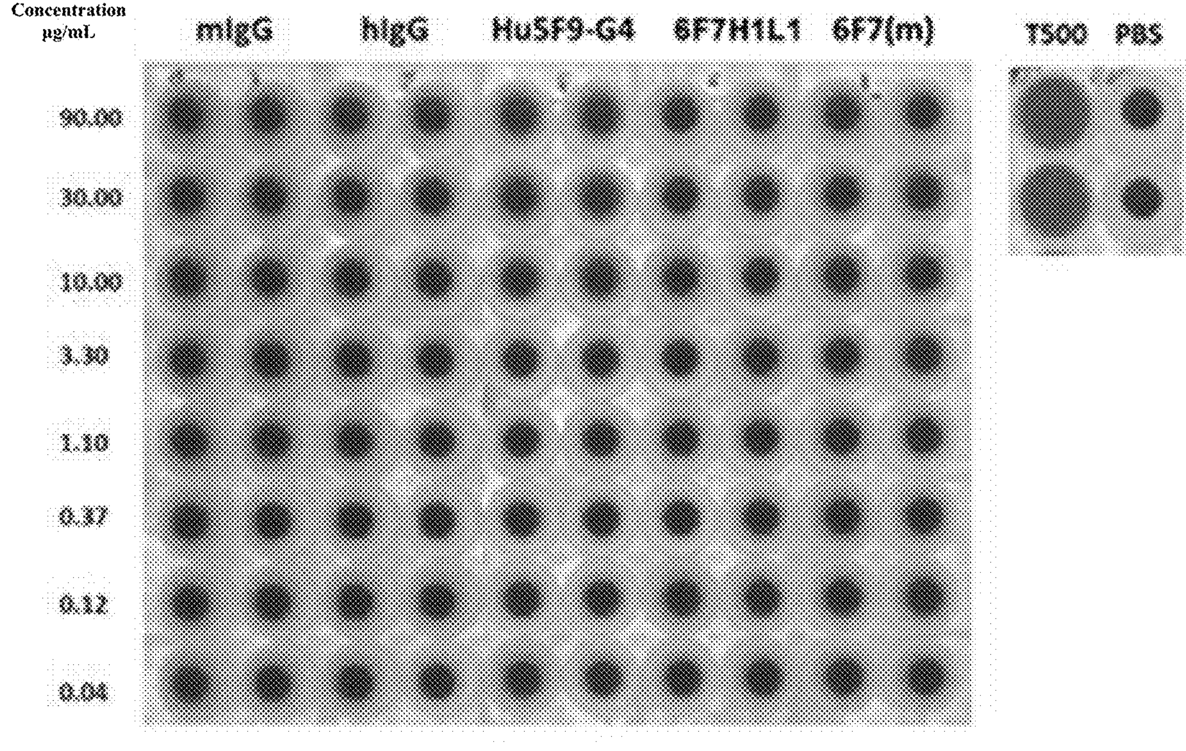
FIG. 17 shows the agglutination of human red blood cells by an anti-CD47 antibody.

The effect of 6F7 H1L1(hG4) on the agglutination of normal human red blood cells is shown in FIG. 17. As shown in the figure, 6F7 H1L1(hG4) did not cause the agglutination of red blood cells at all the concentrations tested, and the control antibody Hu5F9-G4 did not cause the agglutination of red blood cells at concentrations equal to less than 3.3 μg/mL. When the concentration is more than or equal to 10 μg/mL, noticeable facilitated agglutination of red blood cells by Hu5F9-G4 can be observed.

Example 10: Therapeutic Effect of 6F7 H1L1(hG4) on Subcutaneously Grafted MDA-MB-231 Tumors The in vivo activity of 6F7 H1L1(hG4) was studied by measuring the volume of human breast cancer cell MDA-MB-231 tumors subcutaneously grafted on SCID/beige mice after administration of 6F7 H1L1(hG4). The collected MDA-MB-231 (ATCC, Cat. No. HTB-26) cells were subcutaneously grafted into SCID/beige mice, for a total of 40 mice, at $5\times10^6$ cells/mouse at the right flank. When the tumor volume reached about 100-120 $mm^3$, the mice were evenly divided into 5 groups of 7 mice according to the average tumor volume: a model group, an Hu5F9-G4 high dose group, an Hu5F9-G4 low dose group, a 6F7 H1L1 (hG4) high dose group and a 6F7 H1L1(hG4) low dose group, wherein the high dose groups were treated at a dose of 0.2 mg/kg, and the low dose groups were treated at a dose of 0.02 mg/kg. The day of grouping was indicated as D0, and the administration was performed on D0, D3, D7, D10, D14 and D17.

The tumor size was measured twice weekly after grouping using a vernier caliper, and the tumor volume was calculated according to the formula $TV=0.5\times ab^2$, where a is the long diameter of the tumor, b is the short diameter of the tumor, and TV is the volume of the tumor. TGI (%) (tumor growth inhibition rate) was calculated from the tumor volume according to the formula $\% \, TGI=(1-(Ti-T0)/(Ci-C0))\times 100\%$, where Ti and Ci are average tumor volumes on day i of the treatment and model groups, respectively, and T0 and C0 are average tumor volumes on day 0 of the treatment and model groups, respectively. The results were evaluated by one-way analysis of variance after the inter-group comparison processed by GraphPad software.

Figure 18:
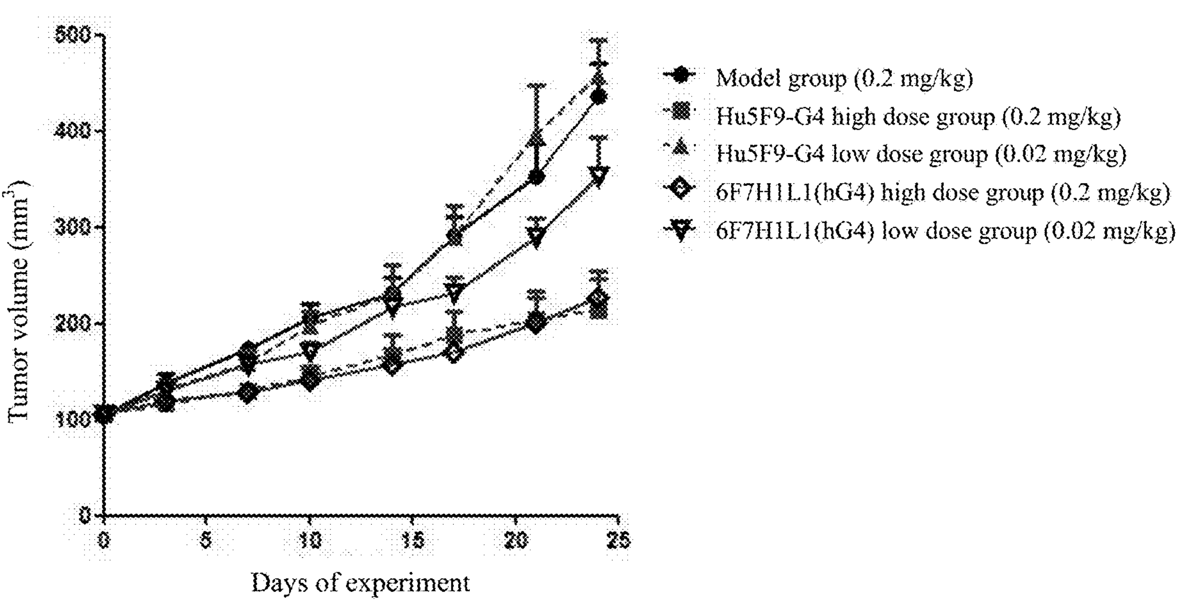
FIG. 18 shows the therapeutic effect of 6F7 H1L1(hG4) on subcutaneously grafted MDA-MB-231 tumors.

The results are shown in FIG. 18. On day 24 after grouping, in both the control antibody Hu5F9-G4 high dose group and 6F7 H1L1(hG4) high dose group, the growth of MDA-MB-231 tumors were effectively inhibited ($P<0.01$), and the inhibition of the growth of MDA-MB-231 tumor by Hu5F9-G4 and 6F7 H1L1(hG4) presented an dose-response relationship. TGI values (%) for the control antibody Hu5F9-G4 high dose group, the 6F7 H1L1(hG4) high dose group, and the 6F7 H1L1(hG4) low dose group were 67%, 63% and 25%, respectively. Compared with the control antibody group, the 6F7 H1L1(hG4) low dose group presents significantly higher efficacy than the Hu5F9-G4 low dose group, and the 6F7 H1L1(hG4) high dose group and the control antibody high dose group presents comparable efficacy ($P>0.05$).

Example 11: Effect of Single Administrations of 6F7 H1L1(hG4) and Hu5F9-G4 to Cynomolgus Monkeys on Hemoglobin and Hematocrit 4 cynomolgus monkeys, randomized into 2 groups of 2 monkeys according to the weight and sex, half male and half female. A 6F7 H1L1(hG4) group and an Hu5F9-G4 group were set up, and intravenously treated at a dose of 10 mg/kg. Hemoglobin and hematocrit were detected using a hematology analyzer.

Figure 19:
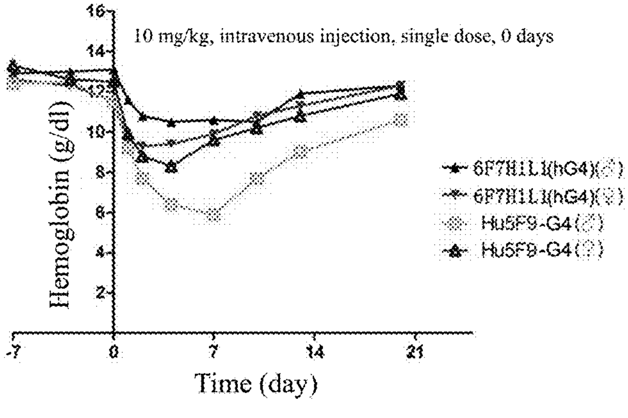
FIG. 19 shows changes in the concentration of hemoglobin after single administrations of 6F7 H1L1(hG4) and Hu5F9-G4 to cynomolgus monkeys.
Figure 20:
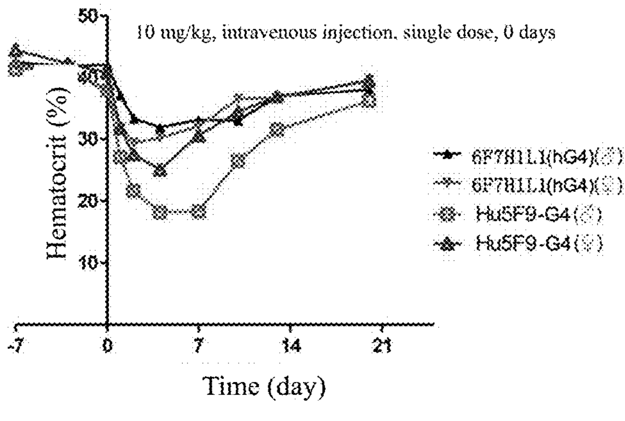
FIG. 20 shows changes in the hematocrit after single administrations of 6F7 H1L1(hG4) and Hu5F9-G4 to cynomolgus monkeys.

The results are shown in FIGS. 19 and 20, and Table 12.

The results show that hemoglobin and hematocrit were reduced to different degrees after single administrations of H1L1(hG4) and Hu5F9-G4 to the cynomolgus monkeys at 10 mg/kg, and the lowest anemia points were reached after 2-7 days, with the anemia level of the Hu5F9-G4 group being higher than that of the 6F7 H1L1(hG4) group; the monkeys could spontaneously recover from the anemia caused by the two antibodies to the baseline level about 20 days after the administration.

TABLE 12

Individual hemoglobin and hematocrit data for cynomolgus monkeys after single administrations of 6F7 H1L1(hG4) and Hu5F9-G4

| | Indexes | | | | | | | |
|---|---|---|---|---|---|---|---|---|
| | HGB g/dL | | | | HCT % | | | |
| | Group | | | | | | | |
| Detection Date | 6F7 H1L1(hG4) male | 6F7 H1L1(hG4) female | Hu5F9-G4 male | Hu5F9-G4 female | 6F7 H1L1(hG4) male | 6F7 H1L1(hG4) female | Hu5F9-G4 male | Hu5F9-G4 female |
| 7 days before administration | 12.9 | 12.6 | 12.4 | 13.3 | 42.5 | 42.1 | 41.4 | 44.5 |
| 3 days before administration | 13 | 12.3 | 12.5 | 12.6 | 41.9 | 41.4 | 41.7 | 42.3 |
| 0 days after administration | 13.1 | 11.6 | 11.5 | 12.5 | 42.1 | 37.7 | 37.9 | 40.8 |

TABLE 12-continued

Individual hemoglobin and hematocrit data for cynomolgus monkeys after single administrations of 6F7 H1L1(hG4) and Hu5F9-G4

| Detection Date | Indexes | | | | | | | |
|---|---|---|---|---|---|---|---|---|
| | HGB g/dL | | | | HCT % | | | |
| | Group | | | | | | | |
| | 6F7 H1L1(hG4) male | 6F7 H1L1(hG4) female | Hu5F9-G4 male | Hu5F9-G4 female | 6F7 H1L1(hG4) male | 6F7 H1L1(hG4) female | Hu5F9-G4 male | Hu5F9-G4 female |
| 1 day after administration | 11.6 | 9.6 | 9.2 | 9.9 | 37.1 | 31.8 | 27.1 | 31.7 |
| 2 days after administration | 10.8 | 9.3 | 7.7 | 8.8 | 33.3 | 29.4 | 21.6 | 27.5 |
| 4 days after administration | 10.5 | 9.4 | 6.4 | 8.3 | 31.9 | 30.2 | 18.2 | 25.1 |
| 7 days after administration | 10.6 | 9.9 | 5.9 | 9.6 | 33.1 | 32.1 | 18.3 | 30.6 |
| 10 days after administration | 10.5 | 10.8 | 7.7 | 10.2 | 33 | 36.5 | 26.5 | 34.4 |
| 13 days after administration | 11.9 | 11.3 | 9 | 10.8 | 36.9 | 36.7 | 31.5 | 36.9 |
| 20 days after administration | 12.3 | 12.3 | 10.6 | 11.9 | 38.1 | 39.7 | 36.2 | 39.5 |

The embodiments of the present invention have been described above in detail, but the present invention is not limited to the embodiments. Those skilled in the art can make various equivalent modifications or replacements without violating the spirit of the present invention. These equivalent modifications or replacements are included in the scope defined by the claims of the present application.

SEQUENCE LISTING

6F7 heavy chain variable region:

(SEQ ID NO: 1)
CAGGTGCAGCTGCAGCAGCCAGGAGCAGAGCTGGTGAGGCCAGGAGCATC

CGTGAAGCTGTCTTGTAAGGCCAGCGGCTACACCTTCACATCCTATTGGA

TGAACTGGGTGAAGCAGAGGCCTGGACAGGGACTGGAGTGGATCGGCATG

ATCGACCCAAGCGATTCCGAGACCCACAACAATCAGATGTTTAAGGACAA

GGCCACCCTGACAGTGGATAAGAGCTCCAATACCGCCTACATGCACCTGT

CTAGCCTGACATCTGAGGACAGCGCCGTGTATCACTGCGCCCGGCTGTAC

AGATGGTATTTTGACGTGTGGGGAGCAGGAACCACAGTGACCGTGTCCTC

T (SEQ ID NO: 2)
QVQLQQPGAELVRPGASVKLSCKASGYTFTSYWMNWVKQRPGQGLEWIGM

IDPSDSETHNNQMFKDKATLTVDKSSNTAYMHLSSLTSEDSAVYHCARLY

RWYFDVWGAGTTVTVSS

6F7 light chain variable region:

(SEQ ID NO: 3)
AACATCGTGATGACCCAGTCCCCCAAGTCTATGAGCATGTCCCTGGGCGA

GAGGGTGACCCTGTCCTGTAAGGCCTCTGAGATCGTGGGCACATACGTGT

CTTGGTTTCAGCAGAAGCCACACCAGAGCCCCAAGCTGCTGATCTACGGC

GCCTCCAATCGGTATACAGGCGTGCCTGACAGATTCACCGGCTCTGGCAG

CGCCACAGACTTCACCCTGACAATCTCTAACGTGCAGGCCGAGGACCTGG

-continued

CCGATTATCACTGCGGCCAGAGCTACAATTTCCCTTATACCTTTGGCGGC

GGCACAAAGCTGGAGATCAAG (SEQ ID NO: 4)
NIVMTQSPKSMSMSLGERVTLSCKASEIVGTYVSWFQQKPHQSPKLLIYG

ASNRYTGVPDRFTGSGSATDFTLTISNVQAEDLADYHCGQSYNFPYTFGG

GTKLEIK

6F7CDR

HCDR1:

(SEQ ID NO: 5)
GYTFTSYW

HCDR2:

(SEQ ID NO: 6)
IDPSDSET

HCDR3:

(SEQ ID NO: 7)
ARLYRWYFDV

LCDR1:

(SEQ ID NO: 8)
EIVGTY

LCDR2:

(SEQ ID NO: 9)
GAS

LCDR3:

(SEQ ID NO: 10)
GQSYNFPYT

6F7H1:

(SEQ ID NO: 11)
CAGGTGCAGCTGGTGCAGAGCGGAGCAGAGGTGGTGAAGCCAGGAGCCTC

TGTGAAGCTGAGCTGTAAGGCCTCCGGCTACACCTTCACAAGCTATTGGA

TGAACTGGGTGCGGCAGAGACCAGGACAGGGACTGGAGTGGATCGGAATG

ATCGACCCTTCCGATTCTGAGACCCACAATGCCCAGAAGTTTCAGGGCAA

GGCCACCCTGACAGTGGACAAGAGCACCTCCACAGCCTACATGCACCTGA

-continued

GCTCCCTGCGGTCCGAGGACACAGCCGTGTACTATTGCGCCAGGCTGTAC

CGCTGGTATTTTGACGTGTGGGGAGCAGGAACCACAGTGACCGTGTCTAG

C (SEQ ID NO: 12)
QVQLVQSGAEVVKPGASVKLSCKASGYTFTSYWMNWVRQRPGQGLEWIGM

IDPSDSETHNAQKFQGKATLTVDKSTSTAYMHLSSLRSEDTAVYYCARLY

RWYFDVWGAGTTVTVSS

6F7L1:
(SEQ ID NO: 13)
AACATCGTGATGACCCAGTCCCCAGCCACAATGTCTATGAGCCCAGGAGA

GAGGGTGACCCTGTCCTGTAGAGCCTCTGAGATCGTGGGCACATACGTGT

CTTGGTTTCAGCAGAAGCCAGGACAGGCACCTAGGCTGCTGATCTACGGA

GCAAGCAACAGGTATACCGGAGTGCCAGCACGCTTCTCCGGCTCTGGCAG

CGGCACAGACTTTACCCTGACAATCAGCTCCGTGCAGCCTGAGGACCTGG

CCGATTATCACTGCGGCCAGTCTTACAATTTCCCATATACCTTTGGCGGC

GGCACAAAGCTGGAGATCAAG (SEQ ID NO: 14)
NIVMTQSPATMSMSPGERVTLSCRASEIVGTYVSWFQQKPGQAPRLLIYG

ASNRYTGVPARFSGSGSGTDFTLTISSVQPEDLADYHCGQSYNFPYTFGG

GTKLEIK

6F7H2:
(SEQ ID NO: 15)
CAGGTGCAGCTGGTGCAGAGCGGAGCAGAGGTGGTGAAGCCAGGAGCCTC

TGTGAAGGTGAGCTGTAAGGCCTCCGGCTACACCTTCACATCCTATTGGA

TGAACTGGGTGCGGCAGAGACCAGGACAGGGACTGGAGTGGATCGGAATC

ATCGACCCTTCCGATTCTGAGACCTCTAATGCCCAGAAGTTTCAGGGCCG

GGTGACCCTGACAGTGGACAAGAGCACCTCCACAGCCTACATGCACCTGA

GCTCCCTGAGGAGCGAGGACACAGCCGTGTACTATTGCGCCAGGCTGTAC

CGCTGGTATTTTGACGTGTGGGGAGCAGGAACCACAGTGACCGTGTCTAG

C (SEQ ID NO: 16)
QVQLVQSGAEVVKPGASVKVSCKASGYTFTSYWMNWVRQRPGQGLEWIGI

IDPSDSETSNAQKFQGRVTLTVDKSTSTAYMHLSSLRSEDTAVYYCARLY

RWYFDVWGAGTTVTVSS

6F7L2:
(SEQ ID NO: 17)
AACATCGTGATGACCCAGTCCCCAGCCACACTGTCTCTGAGCCCAGGAGA

GAGGGTGACCCTGTCCTGTAGAGCCTCTGAGATCGTGGGCACATACGTGT

CTTGGTTTCAGCAGAAGCCAGGACAGGCACCTAGGCTGCTGATCTATGGC

GCCAGCAACAGGGCAACCGGCATCCCCGCACGCTTCTCCGGCTCTGGCAG

CGGCACAGACTTTACCCTGACAATCAGCTCCCTGCAGCCTGAGGACCTGG

CCGATTACTATTGCGGCCAGTCTTACAATTTCCCATATACCTTTGGCGGC

GGCACAAAGCTGGAGATCAAG

-continued (SEQ ID NO: 18)
NIVMTQSPATLSLSPGERVTLSCRASEIVGTYVSWFQQKPGQAPRLLIYG

ASNRATGIPARFSGSGSGTDFTLTISSLQPEDLADYYCGQSYNFPYTFGG

GTKLEIK

6F7H3:
(SEQ ID NO: 19)
CAGGTGCAGCTGGTGCAGAGCGGAGCAGAGGTGGTGAAGCCAGGAGCCTC

TGTGAAGGTGAGCTGTAAGGCCTCCGGCTACACCTTCACATCCTATTGGA

TGAACTGGGTGCGGCAGGCACCAGGACAGGGACTGGAGTGGATCGGCATC

ATCGACCCTTCCGATTCTGAGACCTCTTACGCCCAGAAGTTTCAGGGCAG

GGTGACCCTGACAGTGGACAAGAGCACCTCCACAGCCTATATGGAGCTGA

GCTCCCTGCGCAGCGAGGACACAGCCGTGTACTATTGCGCCCGGCTGTAC

AGATGGTATTTTGACGTGTGGGGAGCAGGAACCACAGTGACCGTGTCTAG

C (SEQ ID NO: 20)
QVQLVQSGAEVVKPGASVKVSCKASGYTFTSYWMNWVRQAPGQGLEWIGI

IDPSDSETSYAQKFQGRVTLTVDKSTSTAYMELSSLRSEDTAVYYCARLY

RWYFDVWGAGTTVTVSS

6F7L3:
(SEQ ID NO: 21)
AACATCGTGATGACCCAGTCCCCAGCCACACTGTCTCTGAGCCCAGGAGA

GAGGGTGACCCTGTCCTGTAGAGCCTCTGAGATCGTGGGCACATACCTGT

CTTGGTATCAGCAGAAGCCAGGACAGGCACCTAGGCTGCTGATCTACGGA

GCCAGCACCAGGGCAACAGGCATCCCCGCACGCTTCTCCGGCTCTGGCAG

CGGCACCGACTTTACCCTGACAATCAGCTCCCTGCAGCCTGAGGATTTTG

CCGTGTACTATTGCGGCCAGTCTTACAATTTCCCATATACCTTTGGCGGC

GGCACAAAGCTGGAGATCAAG (SEQ ID NO: 22)
NIVMTQSPATLSLSPGERVTLSCRASEIVGTYLSWYQQKPGQAPRLLIYG

ASTRATGIPARFSGSGSGTDFTLTISSLQPEDFAVYYCGQSYNFPYTFGG

GTKLEIK

6F7 heavy chain framework region

FR-H1:
(SEQ ID NO: 23)
QVQLQQPGAELVRPGASVKLSCKAS

FR-H2:
(SEQ ID NO: 24)
MNWVKQRPGQGLEWIGM

FR-H3:
(SEQ ID NO: 25)
HNNQMFKDKATLTVDKSSNTAYMHLSSLTSEDSAVYHC

FR-H4:
(SEQ ID NO: 26)
WGAGTTVTVSS

6F7 light chain framework region

FR-L1:
(SEQ ID NO: 27)
NIVMTQSPKSMSMSLGERVTLSCKAS

-continued

FR-L2:

(SEQ ID NO: 28)

VSWFQQKPHQSPKLLIY

FR-L3:

(SEQ ID NO: 29)

NRYTGVPDRFTGSGSATDFTLTISNVQAEDLADYHC

FR-L4:

(SEQ ID NO: 30)

FGGGTKLEIK

6F7H1 framework region

FR-H1:

(SEQ ID NO: 31)

QVQLVQSGAEVVKPGASVKLSCKAS

FR-H2:

(SEQ ID NO: 32)

MNWVRQRPGQGLEWIGM

FR-H3:

(SEQ ID NO: 33)

HNAQKFQGKATLTVDKSTSTAYMHLSSLRSEDTAVYYC

FR-H4:

(SEQ ID NO: 34)

WGAGTTVTVSS

6F7L1 framework region

FR-L1:

(SEQ ID NO: 35)

NIVMTQSPATMSMSPGERVTLSCRAS

FR-L2:

(SEQ ID NO: 36)

VSWFQQKPGQAPRLLIY

FR-L3:

(SEQ ID NO: 37)

NRYTGVPARFSGSGSGTDFTLTISSVQPEDLADYHC

FR-L4:

(SEQ ID NO: 38)

FGGGTKLEIK

6F7H2 framework region

FR-H1:

(SEQ ID NO: 39)

QVQLVQSGAEVVKPGASVKVSCKAS

FR-H2:

(SEQ ID NO: 40)

MNWVRQRPGQGLEWIGI

FR-H3:

(SEQ ID NO: 41)

SNAQKFQGRVTLTVDKSTSTAYMHLSSLRSEDTAVYYC

FR-H4:

(SEQ ID NO: 42)

WGAGTTVTVSS

6F7L2 framework region

FR-L1:

(SEQ ID NO: 43)

NIVMTQSPATLSLSPGERVTLSCRAS

FR-L2:

(SEQ ID NO: 44)

VSWFQQKPGQAPRLLIY

FR-L3:

(SEQ ID NO: 45)

NRATGIPARFSGSGSGTDFTLTISSLQPEDLADYYC

FR-L4:

(SEQ ID NO: 46)

FGGGTKLEIK

-continued

6F7H3 framework region

FR-H1:

(SEQ ID NO: 47)

QVQLVQSGAEVVKPGASVKVSCKAS

FR-H2:

(SEQ ID NO: 48)

MNWVRQAPGQGLEWIGI

FR-H3:

(SEQ ID NO: 49)

SYAQKFQGRVTLTVDKSTSTAYMELSSLRSEDTAVYYC

FR-H4:

(SEQ ID NO: 50)

WGAGTTVTVSS

6F7L3 framework region

FR-L1:

(SEQ ID NO: 51)

NIVMTQSPATLSLSPGERVTLSCRAS

FR-L2:

(SEQ ID NO: 52)

LSWYQQKPGQAPRLLIY

FR-L3:

(SEQ ID NO: 53)

TRATGIPARFSGSGSGTDFTLTISSLQPEDFAVYYC

FR-L4:

(SEQ ID NO: 54)

FGGGTKLEIK

IgGIM heavy chain constant region (SEQ ID NO: 55)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Heavy chain constant region Ig gamma-4 chain C region (SEQ ID NO: 56)

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

Light chain constant region Ig kappa chain C region (SEQ ID NO: 57)

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Heavy chain constant region Ig gamma-1 chain C region
(SEQ ID NO: 58)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Amino acid sequence of 6F7H1L1(G1M) heavy chain
(SEQ ID NO: 59)
QVQLVQSGAEVVKPGASVKLSCKASGYTFTSYWMNWVRQRPGQGLEWIGM
IDPSDSETHNAQKFQGKATLTVDKSTSTAYMHLSSLRSEDTAVYYCARLY
RWYFDVWGAGTTVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK Amino acid sequence of 6F7H1L1(G1M) light chain
(SEQ ID NO: 60)
NIVMTQSPATMSMSPGERVTLSCRASEIVGTYVSWFQQKPGQAPRLLIYG
ASNRYTGVPARFSGSGSGTDFTLTISSVQPEDLADYHCGQSYNFPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Amino acid sequence of 6F7H2L2(G1M) heavy chain
(SEQ ID NO: 61)
QVQLVQSGAEVVKPGASVKVSCKASGYTFTSYWMNWVRQRPGQGLEWIGI
IDPSDSETSNAQKFQGRVTLTVDKSTSTAYMHLSSLRSEDTAVYYCARLY
RWYFDVWGAGTTVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK Amino acid sequence of 6F7H2L2(G1M) light chain
(SEQ ID NO: 62)
NIVMTQSPATLSLSPGERVTLSCRASEIVGTYVSWFQQKPGQAPRLLIYG
ASNRATGIPARFSGSGSGTDFTLTISSLQPEDLADYYCGQSYNFPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Amino acid sequence of 6F7H3L3(G1M) heavy chain
(SEQ ID NO: 63)
QVQLVQSGAEVVKPGASVKVSCKASGYTFTSYWMNWVRQAPGQGLEWIGI
IDPSDSETSYAQKFQGRVTLTVDKSTSTAYMELSSLRSEDTAVYYCARLY
RWYFDVWGAGTTVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK Amino acid sequence of 6F7H3L3(G1M) light chain
(SEQ ID NO: 64)
NIVMTQSPATLSLSPGERVTLSCRASEIVGTYLSWYQQKPGQAPRLLIYG
ASTRATGIPARFSGSGSGTDFTLTISSLQPEDFAVYYCGQSYNFPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Amino acid sequence of 6F7H1L1(hG4) heavy chain
(SEQ ID NO: 65)
QVQLVQSGAEVVKPGASVKLSCKASGYTFTSYWMNWVRQRPGQGLEWIGM
IDPSDSETHNAQKFQGKATLTVDKSTSTAYMHLSSLRSEDTAVYYCARLY
RWYFDVWGAGTTVTVSSASTKGPSVFPLAPCSRSTSESTAALGCLVKDYF
PEPVTVSWNSGALTSGVHTFPAVLQSSGLYSLSSVVTVPSSSLGTKTYTC
NVDHKPSNTKVDKRVESKYGPPCPSCPAPEFLGGPSVFLFPPKPKDTLMI
SRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK Amino acid sequence of 6F7H1L1(hG4) light chain
(SEQ ID NO: 66)
NIVMTQSPATMSMSPGERVTLSCRASEIVGTYVSWFQQKPGQAPRLLIYG
ASNRYTGVPARFSGSGSGTDFTLTISSVQPEDLADYHCGQSYNFPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Amino acid sequence of 6F7H2L2(hG4) heavy chain
(SEQ ID NO: 67)
QVQLVQSGAEVVKPGASVKVSCKASGYTFTSYWMNWVRQRPGQGLEWIGI
IDPSDSETSNAQKFQGRVTLTVDKSTSTAYMHLSSLRSEDTAVYYCARLY
RWYFDVWGAGTTVTVSSASTKGPSVFPLAPCSRSTSESTAALGCLVKDYF -continued

PEPVTVSWNSGALTSGVHTFPAVLQSSGLYSLSSVVTVPSSSLGTKTYTC

NVDHKPSNTKVDKRVESKYGPPCPSCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

Amino acid sequence of 6F7H2L2(hG4) light chain (SEQ ID NO: 68)

NIVMTQSPATLSLSPGERVTLSCRASEIVGTYVSWFQQKPGQAPRLLIYG

ASNRATGIPARFSGSGSGTDFTLTISSLQPEDLADYYCGQSYNFPYTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Amino acid sequence of 6F7H3L3(hG4) heavy chain (SEQ ID NO: 69)

QVQLVQSGAEVVKPGASVKVSCKASGYTFTSYWMNWVRQAPGQGLEWIGI

IDPSDSETSYAQKFQGRVTLTVDKSTSTAYMELSSLRSEDTAVYYCARLY

RWYFDVWGAGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPSCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

Amino acid sequence of 6F7H3L3(hG4) light chain (SEQ ID NO: 70)

NIVMTQSPATLSLSPGERVTLSCRASEIVGTYLSWYQQKPGQAPRLLIYG

ASTRATGIPARFSGSGSGTDFTLTISSLQPEDFAVYYCGQSYNFPYTFGG

-continued

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Sequence of the mFc tag:

(SEQ ID NO: 71)

PRGPTIKPCPPCKCPAPNLLGGPSVFIFPPKIKDVLMISLSPIVTCVVVD

VSEDDPDVQISWFVNNVEVHTAQTQTHREDYNSTLRVVSALPIQHQDWMS

GKEFKCKVNNKDLPAPIERTISKPKGSVRAPQVYVLPPPEEEMTKKQVTL

TCMVTDFMPEDIYVEWTNNGKTELNYKNTEPVLDSDGSYFMYSKLRVEKK

NWVERNSYSCSVVHEGLHNHHTTKSFSRTPGK

Heavy chain sequence of hIgG (SEQ ID NO: 72)

EVQLEQSGAELMKPGASVKISCKATGYTFTTYWIEWIKQRPGHSLEWIGE

ILPGSDSTYYNEKVKGKVTFTADASSNTAYMQLSSLTSEDSAVYYCARGD

GFYVYWGQGTTLTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Light chain sequence of hIgG (SEQ ID NO: 73)

DIELTQSPATLSVTPGDSVSLSCRASQSISNNLHWYQQKSHESPRLLIKY

TSQSMSGIPSRFSGSGSGTDFTLSINSVETEDFGVYFCQQSGSWPRTFGG

GTKLDIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The TEV amino acid sequence is (SEQ ID NO: 74)

ENLYFQG

---

The invention claimed is:

1. An antibody or an antigen-binding fragment thereof that specifically binds to CD47, which, comprises HCDR1-3 and LCDR1-3 as shown below, wherein the amino acid sequences of the 3 CDR regions of the heavy chain variable region are as follows:

HCDR1: (SEQ ID NO: 5)
GYTFTSYW,

HCDR2: (SEQ ID NO: 6)
IDPSDSET,
and

HCDR3: (SEQ ID NO: 7)
ARLYRWYFDV;
and and the amino acid sequences of the 3 CDR regions of the light chain variable region are as follows:

LCDR1: (SEQ ID NO: 8)
EIVGTY,

LCDR2: (SEQ ID NO: 9)
GAS,
and

LCDR3: (SEQ ID NO: 10)
GQSYNFPYT

2. The antibody or the antigen-binding fragment thereof according to claim 1, wherein the antibody further comprises a heavy chain constant region and a light chain constant region, and the constant regions are derived from species other than murine.

3. The antibody or the antigen-binding fragment thereof according to claim 1, wherein the antibody comprises a combination of a heavy chain and a light chain selected from the group consisting of the following:

(a) a heavy chain set forth in SEQ ID NO: 59 and a light chain set forth in SEQ ID NO: 60;
(b) a heavy chain set forth in SEQ ID NO: 61 and a light chain set forth in SEQ ID NO: 62;
(c) a heavy chain set forth in SEQ ID NO: 63 and a light chain set forth in SEQ ID NO: 64;
(d) a heavy chain set forth in SEQ ID NO: 65 and a light chain set forth in SEQ ID NO: 66;
(e) a heavy chain set forth in SEQ ID NO: 67 and a light chain set forth in SEQ ID NO: 68; and
(f) a heavy chain set forth in SEQ ID NO: 69 and a light chain set forth in SEQ ID NO: 70.

4. The antibody or the antigen-binding fragment thereof according to claim 1, wherein the antibody further comprises an amino acid mutation introduced at position 234 and/or 235 in the constant region of the heavy chain according to the EU numbering system.

5. The antibody or the antigen-binding fragment thereof according to claim 4, wherein the antibody comprises a combination of a heavy chain and a light chain selected from the group consisting of the following:
(a) a heavy chain set forth in SEQ ID NO: 59 and a light chain set forth in SEQ ID NO: 60;
(b) a heavy chain set forth in SEQ ID NO: 61 and a light chain set forth in SEQ ID NO: 62; and
(c) a heavy chain set forth in SEQ ID NO: 63 and a light chain set forth in SEQ ID NO: 64.

6. The antibody or the antigen-binding fragment thereof according to claim 1, wherein the antigen-binding fragment is selected from Fab, Fab', $F(ab')_2$, Fd, Fv, Fab/c, single chain antibody, or bivalent antibody.

7. The antibody or the antigen-binding fragment thereof according to claim 1, wherein the antibody is a humanized antibody, a chimeric antibody or a multispecific antibody.

8. The antibody or the antigen-binding fragment thereof according to claim 1, which is encoded by a polynucleotide.

9. The antibody or antigen-binding fragment thereof according to claim 8 wherein the polynucleotide molecule is contained in a vector or a host cell.

10. The antibody conjugate comprising the antibody or the antigen-binding fragment thereof according claim 1, wherein the antibody or the antigen-binding fragment thereof is contained in an antibody conjugate, a pharmaceutical composition, a multiple specific antibody, a fusion protein, a medicament or a kit, wherein the antibody conjugate further comprises a conjugated moiety coupled thereto to the antibody or antigen-binding fragment thereof.

11. A hybridoma cell line and a monoclonal antibody produced by the hybridoma cell line, wherein the hybridoma cell line is hybridoma cell line LT012 under CCTCC NO. 2018135.

12. A method, comprising administering a cell comprising the antibody or the antigen-binding fragment thereof according to claim 1, or administering to a subject in need an effective amount of the antibody or the antigen-binding fragment thereof according to claim 1, wherein the method is selected from:
a method for blocking the binding of CD47 to human SIRPα,
a method for blocking the activity of human CD47 or down-regulating the level of human CD47,
a method for blocking cellular response mediated by the binding of human SIRPα to CD47, and
a method for treating a tumor.

13. The antibody or the antigen-binding fragment thereof according to claim 1, wherein the antibody is secreted by a hybridoma cell line, wherein the hybridoma cell line is hybridoma cell line LT012 under CCTCC NO. 2018135.

14. The antibody or the antigen-binding fragment thereof according to claim 1, wherein the antibody comprises:
(a) a heavy chain variable region comprising or consisting of: an amino acid sequence set forth in SEQ ID NO: 2, and a light chain variable region comprising or consisting of: an amino acid sequence set forth in SEQ ID NO: 4;
(b) a heavy chain variable region comprising or consisting of: an amino acid sequence set forth in SEQ ID NO: 12; and a light chain variable region comprising or consisting of: an amino acid sequence set forth in SEQ ID NO: 14;
(c) a heavy chain variable region comprising or consisting of: an amino acid sequence set forth in SEQ ID NO: 16; and a light chain variable region comprising or consisting of: an amino acid sequence set forth in SEQ ID NO: 18; or
(d) a heavy chain variable region comprising or consisting of: an amino acid sequence set forth in SEQ ID NO: 20; and a light chain variable region comprising or consisting of: an amino acid sequence set forth in SEQ ID NO: 22.

15. The antibody or the antigen-binding fragment thereof according to claim 1, wherein the antibody further comprises a heavy chain constant region and a light chain constant region, and the heavy chain constant region is Ig gamma-1 chain C region, ACCESSION No. P01857 set forth in SEQ ID NO: 58 or Ig gamma-4 chain C region, ACCESSION No. P01861.1 set forth in SEQ ID NO: 56; the light chain constant region is Ig kappa chain C region, ACCESSION No. P01834 set forth in SEQ ID NO: 57.

16. The antibody or the antigen-binding fragment thereof according to claim 1, wherein the antibody comprises mutation L234A and/or L235A in the constant region of the heavy chain according to the EU numbering system.

17. The antibody or the antigen-binding fragment thereof according to claim 10, wherein the conjugated moiety is a purification tag, a cytotoxic agent or a detectable label; or
the multispecific antibody further comprises an antibody or an antigen-binding fragment against another antigen and/or another antigenic epitope, or
the kit further comprises a second antibody that specifically identifies the antibody or the antigen-binding fragment thereof, wherein the second antibody further comprising a detectable label; or
the pharmaceutical composition further comprises a pharmaceutically acceptable carrier and/or excipient, or
the medicament is in a form suitable for injection.

18. The antibody or the antigen-binding fragment thereof according to claim 17,
wherein the purification tag is a His tag, or
the detectable label is a radioisotope, a luminescent substance, a colored substance, an enzyme or polyethylene glycol, or
the medicament is in a form suitable for administration by subcutaneous injection, intradermal injection, intravenous injection, intramuscular injection or intralesional injection.

19. The method according to claim 12, wherein the tumor is a tumor expressing CD47.

20. The method according to claim 12, wherein the tumor is a hematological malignancy or a solid tumor.

21. The method according to claim 12, wherein the tumor is lymphoma, colon cancer or breast cancer.

22. The method according to claim 12, wherein the tumor is non-Hodgkin lymphoma.

23. The method according to claim 12, wherein the tumor is B cell lymphoma cells.

* * * * *

SEQUENCE LISTING

<160> NUMBER OF SEQ ID NOS: 74

<210> SEQ ID NO 1
<211> LENGTH: 351
<212> TYPE: DNA
<213> ORGANISM: Artificial Sequence
<220> FEATURE:
<223> OTHER INFORMATION: Synthetic Artificial Sequence

<400> SEQUENCE: 1
caggtgcagc tgcagcagcc aggagcagag ctggtgaggc caggagcatc cgtgaagctg 60
tcttgtaagg ccagcggcta caccttcaca tcctattgga tgaactgggt gaagcagagg 120
cctggacagg gactggagtg gatcggcatg atcgacccaa gcgattccga gacccacaac 180
aatcagatgt ttaaggacaa ggccaccctg acagtggata agagctccaa taccgcctac 240
atgcacctgt ctagcctgac atctgaggac agcgccgtgt atcactgcgc ccggctgtac 300
agatggtatt ttgacgtgtg gggagcagga accacagtga ccgtgtcctc t 351

<210> SEQ ID NO 2
<211> LENGTH: 117
<212> TYPE: PRT
<213> ORGANISM: Artificial Sequence
<220> FEATURE:
<223> OTHER INFORMATION: Synthetic Artificial Sequence

<400> SEQUENCE: 2

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Asn Asn Gln Met Phe
    50                  55                  60

Lys Asp Lys Ala Thr Leu Thr Val Asp Lys Ser Ser Asn Thr Ala Tyr
65                  70                  75                  80

Met His Leu Ser Ser Leu Thr Ser Glu Asp Ser Ala Val Tyr His Cys
                85                  90                  95

Ala Arg Leu Tyr Arg Trp Tyr Phe Asp Val Trp Gly Ala Gly Thr Thr
            100                 105                 110

Val Thr Val Ser Ser
        115
```

<210> SEQ ID NO 3
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 3

```
aacatcgtga tgacccagtc ccccaagtct atgagcatgt ccctgggcga gagggtgacc     60

ctgtcctgta aggcctctga gatcgtgggc acatacgtgt cttggtttca gcagaagcca    120

caccagagcc ccaagctgct gatctacggc gcctccaatc ggtatacagg cgtgcctgac    180

agattcaccg gctctggcag cgccacagac ttcaccctga caatctctaa cgtgcaggcc    240

gaggacctgg ccgattatca ctgcggccag agctacaatt tcccttatac ctttggcggc    300

ggcacaaagc tggagatcaa g                                               321
```

<210> SEQ ID NO 4
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 4

```
Asn Ile Val Met Thr Gln Ser Pro Lys Ser Met Ser Met Ser Leu Gly
1               5                   10                  15

Glu Arg Val Thr Leu Ser Cys Lys Ala Ser Glu Ile Val Gly Thr Tyr
            20                  25                  30

Val Ser Trp Phe Gln Gln Lys Pro His Gln Ser Pro Lys Leu Leu Ile
        35                  40                  45

Tyr Gly Ala Ser Asn Arg Tyr Thr Gly Val Pro Asp Arg Phe Thr Gly
```

```
    50                  55                  60

Ser Gly Ser Ala Thr Asp Phe Thr Leu Thr Ile Ser Asn Val Gln Ala
65                  70                  75                  80

Glu Asp Leu Ala Asp Tyr His Cys Gly Gln Ser Tyr Asn Phe Pro Tyr
                85                  90                  95

Thr Phe Gly Gly Gly Thr Lys Leu Glu Ile Lys
            100                 105


<210> SEQ ID NO 5
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 5

Gly Tyr Thr Phe Thr Ser Tyr Trp
1               5


<210> SEQ ID NO 6
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 6

Ile Asp Pro Ser Asp Ser Glu Thr
1               5


<210> SEQ ID NO 7
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 7

Ala Arg Leu Tyr Arg Trp Tyr Phe Asp Val
1               5                   10


<210> SEQ ID NO 8
<211> LENGTH: 6
<212> TYPE: PRT
<213> ORGANISM: Artificial Sequence
<220> FEATURE:
<223> OTHER INFORMATION: Synthetic Artificial Sequence

<400> SEQUENCE: 8

Glu Ile Val Gly Thr Tyr
1               5


<210> SEQ ID NO 9
<211> LENGTH: 3
<212> TYPE: PRT
<213> ORGANISM: Artificial Sequence
<220> FEATURE:
<223> OTHER INFORMATION: Synthetic Artificial Sequence

<400> SEQUENCE: 9

Gly Ala Ser
1


<210> SEQ ID NO 10
<211> LENGTH: 9
```

<212> TYPE: PRT
<213> ORGANISM: Artificial Sequence
<220> FEATURE:
<223> OTHER INFORMATION: Synthetic Artificial Sequence

<400> SEQUENCE: 10

Gly Gln Ser Tyr Asn Phe Pro Tyr Thr
1               5

<210> SEQ ID NO 11
<211> LENGTH: 351
<212> TYPE: DNA
<213> ORGANISM: Artificial Sequence
<220> FEATURE:
<223> OTHER INFORMATION: Synthetic Artificial Sequence

<400> SEQUENCE: 11
caggtgcagc tggtgcagag cggagcagag gtggtgaagc caggagcctc tgtgaagctg 60
agctgtaagg cctccggcta caccttcaca agctattgga tgaactgggt gcggcagaga 120
ccaggacagg gactggagtg gatcggaatg atcgaccctt ccgattctga gacccacaat 180
gcccagaagt ttcagggcaa ggccaccctg acagtggaca agagcacctc cacagcctac 240
atgcacctga gctccctgcg gtccgaggac acagccgtgt actattgcgc caggctgtac 300
cgctggtatt ttgacgtgtg gggagcagga accacagtga ccgtgtctag c 351

<210> SEQ ID NO 12
<211> LENGTH: 117
<212> TYPE: PRT
<213> ORGANISM: Artificial Sequence
<220> FEATURE:
<223> OTHER INFORMATION: Synthetic Artificial Sequence

<400> SEQUENCE: 12

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Met Ile Asp Pro Ser Asp Ser Glu Thr His Asn Ala Gln Lys Phe
    50                  55                  60

Gln Gly Lys Ala Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser
        115

<210> SEQ ID NO 13
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 13
aacatcgtga tgacccagtc cccagccaca atgtctatga gcccaggaga gagggtgacc 60
ctgtcctgta gagcctctga gatcgtgggc acatacgtgt cttggtttca gcagaagcca 120

```
ggacaggcac ctaggctgct gatctacgga gcaagcaaca ggtataccgg agtgccagca    180

cgcttctccg gctctggcag cggcacagac tttaccctga caatcagctc cgtgcagcct    240

gaggacctgg ccgattatca ctgcggccag tcttacaatt tcccatatac ctttggcggc    300

ggcacaaagc tggagatcaa g                                              321


<210> SEQ ID NO 14
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 14

Asn Ile Val Met Thr Gln Ser Pro Ala Thr Met Ser Met Ser Pro Gly
1               5                   10                  15

Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Tyr Thr Gly Val Pro Ala Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Asp Tyr His Cys Gly Gln Ser Tyr Asn Phe Pro Tyr
                85                  90                  95

Thr Phe Gly Gly Gly Thr Lys Leu Glu Ile Lys
            100                 105


<210> SEQ ID NO 15
<211> LENGTH: 351
<212> TYPE: DNA
<213> ORGANISM: Artificial Sequence
<220> FEATURE:
<223> OTHER INFORMATION: Synthetic Artificial Sequence

<400> SEQUENCE: 15

caggtgcagc tggtgcagag cggagcagag gtggtgaagc caggagcctc tgtgaaggtg     60

agctgtaagg cctccggcta caccttcaca tcctattgga tgaactgggt gcggcagaga    120

ccaggacagg gactggagtg gatcggaatc atcgaccctt ccgattctga gacctctaat    180

gcccagaagt ttcagggccg ggtgaccctg acagtggaca agagcacctc cacagcctac    240

atgcacctga gctccctgag gagcgaggac acagccgtgt actattgcgc caggctgtac    300

cgctggtatt ttgacgtgtg gggagcagga accacagtga ccgtgtctag c             351


<210> SEQ ID NO 16
<211> LENGTH: 117
<212> TYPE: PRT
<213> ORGANISM: Artificial Sequence
<220> FEATURE:
<223> OTHER INFORMATION: Synthetic Artificial Sequence

<400> SEQUENCE: 16

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
```

```
        35                  40                  45

Gly Ile Ile Asp Pro Ser Asp Ser Glu Thr Ser Asn Ala Gln Lys Phe
    50                  55                  60

Gln Gly Arg Val Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser
        115


<210> SEQ ID NO 17
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 17

aacatcgtga tgacccagtc cccagccaca ctgtctctga gcccaggaga gagggtgacc      60

ctgtcctgta gagcctctga gatcgtgggc acatacgtgt cttggtttca gcagaagcca     120

ggacaggcac ctaggctgct gatctatggc gccagcaaca gggcaaccgg catccccgca     180

cgcttctccg gctctggcag cggcacagac tttaccctga caatcagctc cctgcagcct     240

gaggacctgg ccgattacta ttgcggccag tcttacaatt tcccatatac ctttggcggc     300

ggcacaaagc tggagatcaa g                                               321


<210> SEQ ID NO 18
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 18

Asn Ile Val Met Thr Gln Ser Pro Ala Thr Leu Ser Leu Ser Pro Gly
1               5                   10                  15

Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys Gly Gln Ser Tyr Asn Phe Pro Tyr
                85                  90                  95

Thr Phe Gly Gly Gly Thr Lys Leu Glu Ile Lys
            100                 105


<210> SEQ ID NO 19
<211> LENGTH: 351
<212> TYPE: DNA
<213> ORGANISM: Artificial Sequence
<220> FEATURE:
<223> OTHER INFORMATION: Synthetic Artificial Sequence

<400> SEQUENCE: 19
```

```
caggtgcagc tggtgcagag cggagcagag gtggtgaagc caggagcctc tgtgaaggtg      60

agctgtaagg cctccggcta caccttcaca tcctattgga tgaactgggt gcggcaggca     120

ccaggacagg gactggagtg gatcggcatc atcgaccctt ccgattctga gacctcttac     180

gcccagaagt ttcagggcag ggtgaccctg acagtggaca agagcacctc cacagcctat     240

atggagctga gctccctgcg cagcgaggac acagccgtgt actattgcgc ccggctgtac     300

agatggtatt ttgacgtgtg gggagcagga accacagtga ccgtgtctag c              351
```

<210> SEQ ID NO 20
<211> LENGTH: 117
<212> TYPE: PRT
<213> ORGANISM: Artificial Sequence
<220> FEATURE:
<223> OTHER INFORMATION: Synthetic Artificial Sequence

<400> SEQUENCE: 20

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Ile
        35                  40                  45

Gly Ile Ile Asp Pro Ser Asp Ser Glu Thr Ser Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser
        115
```

<210> SEQ ID NO 21
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 21

```
aacatcgtga tgacccagtc cccagccaca ctgtctctga gcccaggaga gagggtgacc      60

ctgtcctgta gagcctctga gatcgtgggc acatacctgt cttggtatca gcagaagcca     120

ggacaggcac ctaggctgct gatctacgga gccagcacca gggcaacagg catccccgca     180

cgcttctccg gctctggcag cggcaccgac tttaccctga caatcagctc cctgcagcct     240

gaggattttg ccgtgtacta ttgcggccag tcttacaatt tcccatatac ctttggcggc     300

ggcacaaagc tggagatcaa g                                               321
```

<210> SEQ ID NO 22
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 22

```
Asn Ile Val Met Thr Gln Ser Pro Ala Thr Leu Ser Leu Ser Pro Gly
1               5                   10                  15

Glu Arg Val Thr Leu Ser Cys Arg Ala Ser Glu Ile Val Gly Thr Tyr
            20                  25                  30

Leu Ser Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gly Gln Ser Tyr Asn Phe Pro Tyr
                85                  90                  95

Thr Phe Gly Gly Gly Thr Lys Leu Glu Ile Lys
            100                 105


<210> SEQ ID NO 23
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 23

Gln Val Gln Leu Gln Gln Pro Gly Ala Glu Leu Val Arg Pro Gly Ala
1               5                   10                  15

Ser Val Lys Leu Ser Cys Lys Ala Ser
            20                  25


<210> SEQ ID NO 24
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 24

Met Asn Trp Val Lys Gln Arg Pro Gly Gln Gly Leu Glu Trp Ile Gly
1               5                   10                  15

Met


<210> SEQ ID NO 25
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 25

His Asn Asn Gln Met Phe Lys Asp Lys Ala Thr Leu Thr Val Asp Lys
1               5                   10                  15

Ser Ser Asn Thr Ala Tyr Met His Leu Ser Ser Leu Thr Ser Glu Asp
            20                  25                  30

Ser Ala Val Tyr His Cys
        35


<210> SEQ ID NO 26
<211> LENGTH: 11
<212> TYPE: PRT
<213> ORGANISM: Artificial Sequence
<220> FEATURE:
<223> OTHER INFORMATION: Synthetic Artificial Sequence
```

<400> SEQUENCE: 26

Trp Gly Ala Gly Thr Thr Val Thr Val Ser Ser
1 5 10

<210> SEQ ID NO 27
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 27

Asn Ile Val Met Thr Gln Ser Pro Lys Ser Met Ser Met Ser Leu Gly
1 5 10 15

Glu Arg Val Thr Leu Ser Cys Lys Ala Ser
20 25

<210> SEQ ID NO 28
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 28

Val Ser Trp Phe Gln Gln Lys Pro His Gln Ser Pro Lys Leu Leu Ile
1 5 10 15

Tyr

<210> SEQ ID NO 29
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 29

Asn Arg Tyr Thr Gly Val Pro Asp Arg Phe Thr Gly Ser Gly Ser Ala
1 5 10 15

Thr Asp Phe Thr Leu Thr Ile Ser Asn Val Gln Ala Glu Asp Leu Ala
20 25 30

Asp Tyr His Cys
35

<210> SEQ ID NO 30
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 30

Phe Gly Gly Gly Thr Lys Leu Glu Ile Lys
1 5 10

<210> SEQ ID NO 31
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 31

Gln Val Gln Leu Val Gln Ser Gly Ala Glu Val Val Lys Pro Gly Ala 1 5 10 15

Ser Val Lys Leu Ser Cys Lys Ala Ser
20 25

<210> SEQ ID NO 32
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 32

Met Asn Trp Val Arg Gln Arg Pro Gly Gln Gly Leu Glu Trp Ile Gly
1 5 10 15

Met

<210> SEQ ID NO 33
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 33

His Asn Ala Gln Lys Phe Gln Gly Lys Ala Thr Leu Thr Val Asp Lys
1 5 10 15

Ser Thr Ser Thr Ala Tyr Met His Leu Ser Ser Leu Arg Ser Glu Asp
20 25 30

Thr Ala Val Tyr Tyr Cys
35

<210> SEQ ID NO 34
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 34

Trp Gly Ala Gly Thr Thr Val Thr Val Ser Ser
1 5 10

<210> SEQ ID NO 35
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 35

Asn Ile Val Met Thr Gln Ser Pro Ala Thr Met Ser Met Ser Pro Gly
1 5 10 15

Glu Arg Val Thr Leu Ser Cys Arg Ala Ser
20 25

<210> SEQ ID NO 36
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 36

Val Ser Trp Phe Gln Gln Lys Pro Gly Gln Ala Pro Arg Leu Leu Ile

```
1               5                   10                  15

Tyr


<210> SEQ ID NO 37
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 37

Asn Arg Tyr Thr Gly Val Pro Ala Arg Phe Ser Gly Ser Gly Ser Gly
1               5                   10                  15

Thr Asp Phe Thr Leu Thr Ile Ser Ser Val Gln Pro Glu Asp Leu Ala
            20                  25                  30

Asp Tyr His Cys
        35


<210> SEQ ID NO 38
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 38

Phe Gly Gly Gly Thr Lys Leu Glu Ile Lys
1               5                   10


<210> SEQ ID NO 39
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 39

Gln Val Gln Leu Val Gln Ser Gly Ala Glu Val Val Lys Pro Gly Ala
1               5                   10                  15

Ser Val Lys Val Ser Cys Lys Ala Ser
            20                  25


<210> SEQ ID NO 40
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 40

Met Asn Trp Val Arg Gln Arg Pro Gly Gln Gly Leu Glu Trp Ile Gly
1               5                   10                  15

Ile


<210> SEQ ID NO 41
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 41

Ser Asn Ala Gln Lys Phe Gln Gly Arg Val Thr Leu Thr Val Asp Lys
1               5                   10                  15
```

```
Ser Thr Ser Thr Ala Tyr Met His Leu Ser Ser Leu Arg Ser Glu Asp
            20                  25                  30

Thr Ala Val Tyr Tyr Cys
        35


<210> SEQ ID NO 42
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 42

Trp Gly Ala Gly Thr Thr Val Thr Val Ser Ser
1               5                   10


<210> SEQ ID NO 43
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 43

Asn Ile Val Met Thr Gln Ser Pro Ala Thr Leu Ser Leu Ser Pro Gly
1               5                   10                  15

Glu Arg Val Thr Leu Ser Cys Arg Ala Ser
            20                  25


<210> SEQ ID NO 44
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 44

Val Ser Trp Phe Gln Gln Lys Pro Gly Gln Ala Pro Arg Leu Leu Ile
1               5                   10                  15

Tyr


<210> SEQ ID NO 45
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 45

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Gln Pro Glu Asp Leu Ala
            20                  25                  30

Asp Tyr Tyr Cys
        35


<210> SEQ ID NO 46
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 46
```

Phe Gly Gly Gly Thr Lys Leu Glu Ile Lys
1 5 10

<210> SEQ ID NO 47
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 47

Gln Val Gln Leu Val Gln Ser Gly Ala Glu Val Val Lys Pro Gly Ala
1 5 10 15

Ser Val Lys Val Ser Cys Lys Ala Ser
20 25

<210> SEQ ID NO 48
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 48

Met Asn Trp Val Arg Gln Ala Pro Gly Gln Gly Leu Glu Trp Ile Gly
1 5 10 15

Ile

<210> SEQ ID NO 49
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 49

Ser Tyr Ala Gln Lys Phe Gln Gly Arg Val Thr Leu Thr Val Asp Lys
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 50
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 50

Trp Gly Ala Gly Thr Thr Val Thr Val Ser Ser
1 5 10

<210> SEQ ID NO 51
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 51

Asn Ile Val Met Thr Gln Ser Pro Ala Thr Leu Ser Leu Ser Pro Gly
1 5 10 15

```
Glu Arg Val Thr Leu Ser Cys Arg Ala Ser
            20                  25


<210> SEQ ID NO 52
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 52

Leu Ser Trp Tyr Gln Gln Lys Pro Gly Gln Ala Pro Arg Leu Leu Ile
1               5                   10                  15

Tyr


<210> SEQ ID NO 53
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 53

Thr Arg Ala Thr Gly Ile Pro Ala Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Val Tyr Tyr Cys
        35


<210> SEQ ID NO 54
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 54

Phe Gly Gly Gly Thr Lys Leu Glu Ile Lys
1               5                   10


<210> SEQ ID NO 55
<211> LENGTH: 330
<212> TYPE: PRT
<213> ORGANISM: Artificial Sequence
<220> FEATURE:
<223> OTHER INFORMATION: Synthetic Artificial Sequence

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 56
<211> LENGTH: 327
<212> TYPE: PRT
<213> ORGANISM: Artificial Sequence
<220> FEATURE:
<223> OTHER INFORMATION: Synthetic Artificial Sequence

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125
```

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 57
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 330
<212> TYPE: PRT
<213> ORGANISM: Artificial Sequence
<220> FEATURE:
<223> OTHER INFORMATION: Synthetic Artificial Sequence

<400> SEQUENCE: 58

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 59
<211> LENGTH: 447
<212> TYPE: PRT
<213> ORGANISM: Artificial Sequence
<220> FEATURE:
<223> OTHER INFORMATION: Synthetic Artificial Sequence

<400> SEQUENCE: 59

Gln Val Gln Leu Val Gln Ser Gly Ala Glu Val Val Lys Pro Gly Ala
1 5 10 15

Ser Val Lys Leu Ser Cys Lys Ala Ser Gly Tyr Thr Phe Thr Ser Tyr
20 25 30

```
Trp Met Asn Trp Val Arg Gln Arg Pro Gly Gln Gly Leu Glu Trp Ile
        35                  40                  45

Gly Met Ile Asp Pro Ser Asp Ser Glu Thr His Asn Ala Gln Lys Phe
    50                  55                  60

Gln Gly Lys Ala Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 60
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 60

```
Asn Ile Val Met Thr Gln Ser Pro Ala Thr Met Ser Met Ser Pro Gly
1               5                   10                  15

Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Tyr Thr Gly Val Pro Ala Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Asp Tyr His Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 61
<211> LENGTH: 447
<212> TYPE: PRT
<213> ORGANISM: Artificial Sequence
<220> FEATURE:
<223> OTHER INFORMATION: Synthetic Artificial Sequence

<400> SEQUENCE: 61

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Ile Ile Asp Pro Ser Asp Ser Glu Thr Ser Asn Ala Gln Lys Phe
    50                  55                  60

Gln Gly Arg Val Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95
```

```
Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 62
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 62

Asn Ile Val Met Thr Gln Ser Pro Ala Thr Leu Ser Leu Ser Pro Gly
1               5                   10                  15
```

```
Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 63
<211> LENGTH: 447
<212> TYPE: PRT
<213> ORGANISM: Artificial Sequence
<220> FEATURE:
<223> OTHER INFORMATION: Synthetic Artificial Sequence

<400> SEQUENCE: 63

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Ile
        35                  40                  45

Gly Ile Ile Asp Pro Ser Asp Ser Glu Thr Ser Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 64
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 64

Asn Ile Val Met Thr Gln Ser Pro Ala Thr Leu Ser Leu Ser Pro Gly
1               5                   10                  15

Glu Arg Val Thr Leu Ser Cys Arg Ala Ser Glu Ile Val Gly Thr Tyr
            20                  25                  30

Leu Ser Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Val Tyr Tyr Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 65
<211> LENGTH: 444
<212> TYPE: PRT
<213> ORGANISM: Artificial Sequence
<220> FEATURE:
<223> OTHER INFORMATION: Synthetic Artificial Sequence

<400> SEQUENCE: 65

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Met Ile Asp Pro Ser Asp Ser Glu Thr His Asn Ala Gln Lys Phe
    50                  55                  60

Gln Gly Lys Ala Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220
```

```
Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 66
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 66

Asn Ile Val Met Thr Gln Ser Pro Ala Thr Met Ser Met Ser Pro Gly
1               5                   10                  15

Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Tyr Thr Gly Val Pro Ala Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Asp Tyr His Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 67
<211> LENGTH: 444
<212> TYPE: PRT
<213> ORGANISM: Artificial Sequence
<220> FEATURE:
<223> OTHER INFORMATION: Synthetic Artificial Sequence

<400> SEQUENCE: 67

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Ile Ile Asp Pro Ser Asp Ser Glu Thr Ser Asn Ala Gln Lys Phe
    50                  55                  60

Gln Gly Arg Val Thr Leu Thr Val Asp Lys Ser Thr Ser Thr Ala Tyr
65                  70                  75                  80

Met His Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285
```

```
Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 68
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 68

Asn Ile Val Met Thr Gln Ser Pro Ala Thr Leu Ser Leu Ser Pro Gly
1               5                   10                  15

Glu Arg Val Thr Leu Ser Cys Arg Ala Ser Glu Ile Val Gly Thr Tyr
            20                  25                  30

Val Ser Trp Phe Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 69
<211> LENGTH: 444
<212> TYPE: PRT
<213> ORGANISM: Artificial Sequence
<220> FEATURE:
<223> OTHER INFORMATION: Synthetic Artificial Sequence

<400> SEQUENCE: 69

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Ile
        35                  40                  45

Gly Ile Ile Asp Pro Ser Asp Ser Glu Thr Ser Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Arg Trp Tyr Phe Asp Val Trp Gly Ala Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 70
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 70

Asn Ile Val Met Thr Gln Ser Pro Ala Thr Leu Ser Leu Ser Pro Gly
1               5                   10                  15

Glu Arg Val Thr Leu Ser Cys Arg Ala Ser Glu Ile Val Gly Thr Tyr
            20                  25                  30

Leu Ser Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gly Gln Ser Tyr Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 71
<211> LENGTH: 232
<212> TYPE: PRT
<213> ORGANISM: Artificial Sequence
<220> FEATURE:
<223> OTHER INFORMATION: Synthetic Artificial Sequence
```

<400> SEQUENCE: 71

```
Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Pro Glu Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His His Thr Thr Lys
    210                 215                 220

Ser Phe Ser Arg Thr Pro Gly Lys
225                 230
```

<210> SEQ ID NO 72
<211> LENGTH: 443
<212> TYPE: PRT
<213> ORGANISM: Artificial Sequence
<220> FEATURE:
<223> OTHER INFORMATION: Synthetic Artificial Sequence

<400> SEQUENCE: 72

```
Glu Val Gln Leu Glu Gln Ser Gly Ala Glu Leu Met Lys Pro Gly Ala
1               5                   10                  15

Ser Val Lys Ile Ser Cys Lys Ala Thr Gly Tyr Thr Phe Thr Thr Tyr
            20                  25                  30

Trp Ile Glu Trp Ile Lys Gln Arg Pro Gly His Ser Leu Glu Trp Ile
        35                  40                  45

Gly Glu Ile Leu Pro Gly Ser Asp Ser Thr Tyr Tyr Asn Glu Lys Val
    50                  55                  60

Lys Gly Lys Val Thr Phe Thr Ala Asp Ala Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asp Gly Phe Tyr Val Tyr Trp Gly Gln Gly Thr Thr Leu
            100                 105                 110

Thr Val Ser Ser Ala Ser Thr Lys Gly Pro Ser Val Phe Pro Leu Ala
```

```
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```

<210> SEQ ID NO 73
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 73

```
Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
```

-continued

```
        35                  40                  45

Lys Tyr Thr Ser Gln Ser Met Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Gly Ser Trp Pro Arg
                85                  90                  95

Thr Phe Gly Gly Gly Thr Lys Leu Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 74
<211> LENGTH: 7
<212> TYPE: PRT
<213> ORGANISM: Artificial Sequence
<220> FEATURE:
<223> OTHER INFORMATION: Synthetic Artificial Sequence

<400> SEQUENCE: 74

Glu Asn Leu Tyr Phe Gln Gly
1               5
```